(12) United States Patent
Kikuchi et al.

(10) Patent No.: US 8,759,025 B2
(45) Date of Patent: Jun. 24, 2014

(54) HUMANIZED ANTI-CD47 ANTIBODY

(75) Inventors: Yasufumi Kikuchi, Gotenba (JP); Shinsuke Uno, Gotenba (JP); Yasuko Kinoshita, Gotenba (JP); Shigeyuki Iijima, Gotenba (JP); Naoshi Fukushima, Gotenba (JP); Masayuki Tsuchiya, Gotenba (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 248 days.

(21) Appl. No.: 13/329,658

(22) Filed: Dec. 19, 2011

(65) Prior Publication Data

US 2012/0156724 A1    Jun. 21, 2012

Related U.S. Application Data

(62) Division of application No. 10/578,840, filed as application No. PCT/JP2004/016744 on Nov. 11, 2004, now Pat. No. 8,101,719.

(30) Foreign Application Priority Data

Nov. 11, 2003 (JP) ................................ 2003-381406

(51) Int. Cl.
  *C12P 21/06* (2006.01)
  *C12N 15/87* (2006.01)
  *C12N 5/02* (2006.01)
  *C12N 5/20* (2006.01)
  *C12N 1/20* (2006.01)
  *C12N 15/00* (2006.01)
  *C07H 21/04* (2006.01)

(52) U.S. Cl.
  USPC .......... 435/69.1; 435/455; 435/325; 435/326; 435/252.3; 435/320.1; 536/23.53

(58) Field of Classification Search
  None
  See application file for complete search history.

(56) References Cited

U.S. PATENT DOCUMENTS

| | | | |
|---|---|---|---|
| 5,048,972 A | 9/1991 | Wiese | |
| 5,693,761 A | 12/1997 | Queen et al. | |
| 5,859,205 A | 1/1999 | Adair et al. | |
| 5,994,524 A | 11/1999 | Matsushima et al. | |
| 6,024,956 A | 2/2000 | Matsushima et al. | |
| 6,068,840 A | 5/2000 | Matsushima et al. | |
| 6,245,894 B1 | 6/2001 | Matsushima et al. | |
| 7,531,643 B2 | 5/2009 | Fukushima et al. | |
| 7,696,325 B2 | 4/2010 | Fukushima et al. | |
| 2002/0082396 A1 | 6/2002 | Matsushima et al. | |
| 2003/0108546 A1 | 6/2003 | Fukushima et al. | |
| 2003/0157100 A1 | 8/2003 | Fukushima et al. | |
| 2003/0211108 A1 | 11/2003 | Fukushima et al. | |
| 2004/0242847 A1 | 12/2004 | Fukushima et al. | |

FOREIGN PATENT DOCUMENTS

| | | |
|---|---|---|
| EP | 1167388 A1 | 1/2002 |
| JP | 4-502408 A | 5/1992 |
| JP | 8-217799 A | 8/1996 |
| JP | 11-92500 A | 4/1999 |
| WO | WO 99/12973 A1 | 3/1999 |
| WO | WO 02/33073 A1 | 4/2002 |

OTHER PUBLICATIONS

Kikuchi et al., "CD47 Kogen to Tokuiteki ni Ketsugo shi Hakketsubyo Saibo ni Apoptis o Yudo suru Diabody no Kochiku," Dai 26 Kai The Molecular Biology Society of Japan Nenkai Program, Koen Yoshishu, Nov. 25, 2003, p. 660, 1PC-166.

Mateo et al., "CD47 ligation induces caspase-independent cell death in chronic lymphocytic leukemia," Nature Medicine, Nov. 1999, 5(11):1277-1284.

Padlan, Eduardo A., "Anatomy of the Antibody Molecule," Molecular Immunology, 1994, 31(3):169-217.

Protolano et al., "Lack of Promiscuity in Autoantigen-Specific H and L Chain Combinations as Revealed by Human H and L Chain 'Routelle'," J. Immunol., Feb. 1, 1993, 150(3):880-887.

Sato et al., "Reshaping a Human Antibody to Inhibit the Interleukin 6-dependent Tumor Cell Growth," Cancer Research, Feb. 15, 1993, 53:851-856.

Supplementary European Search Report dated Oct. 6, 2009, in corresponding EP 04818256.2, 4 pages.

*Primary Examiner* — Maher Haddad
(74) *Attorney, Agent, or Firm* — Foley & Lardner LLP

(57) ABSTRACT

The present invention relates to humanized antibodies binding to CD47; diabodies binding to human CD47, characterized in that a disulfide bond exists between diabody-forming fragments; genes encoding any one of said antibodies; vectors containing said genes; host cells containing said vectors; processes for preparing antibodies comprising the step of culturing said host cells; and therapeutic agents for hematological disorders comprising said antibodies.

10 Claims, 19 Drawing Sheets

SEQUENCE LISTING

```
<160> NUMBER OF SEQ ID NOS: 121

<210> SEQ ID NO 1
<211> LENGTH: 133
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cccaagcttc caccatggaa tggagctgga tatttctctt cctcctgtca ggaactgcag      60
gtgtccactc ccaggtgcag ctggtgcagt ctggggctga ggtgaagaag cctggggcct    120
cagtgaaggt ttc                                                       133

<210> SEQ ID NO 2
<211> LENGTH: 133
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcttgagtg gatgggatat atttatcctt acaatgatgg tactaagtat aatgagaagt      60
tcaaggacag agtcacgatg acccgggaca cgtccacgag cacagtctac atggagttga    120
gcagtctcag atc                                                       133

<210> SEQ ID NO 3
<211> LENGTH: 133
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgtaaggata aatatatccc atccactcaa gcccttgtcc aggggcctgt cgcacccagt      60
gaataacatg gttggcgaag gtgtatccag atgccttaca ggaaaccttc actgaggccc    120
caggcttctt cac                                                       133

<210> SEQ ID NO 4
<211> LENGTH: 133
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgcggatcca ctcacctgag gagacggtga ccagggttcc ttggcccag tcgtcgtaag       60
```
tatagtaacc ccctctagca caataataga cggccgtgtc ctcagatctg agactgctca    120
actccatgta gac                                                       133

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccaagcttc caccatggaa tgg                                             23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgcggatcca ctcacctgag gag                                             23

<210> SEQ ID NO 7
<211> LENGTH: 424
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(408)

<400> SEQUENCE: 7 atg gaa tgg agc tgg ata ttt ctc ttc ctc ctg tca gga act gca ggt     48
Met Glu Trp Ser Trp Ile Phe Leu Phe Leu Leu Ser Gly Thr Ala Gly
 1               5                  10                  15 gtc cac tcc cag gtg cag ctg gtg cag tct ggg gct gag gtg aag aag     96
Val His Ser Gln Val Gln Leu Val Gln Ser Gly Ala Glu Val Lys Lys
             20                  25                  30 cct ggg gcc tca gtg aag gtt tcc tgt aag gca tct gga tac acc ttc    144
Pro Gly Ala Ser Val Lys Val Ser Cys Lys Ala Ser Gly Tyr Thr Phe
         35                  40                  45 gcc aac cat gtt att cac tgg gtg cga cag gcc cct gga caa ggg ctt    192
Ala Asn His Val Ile His Trp Val Arg Gln Ala Pro Gly Gln Gly Leu
     50                  55                  60 gag tgg atg gga tat att tat cct tac aat gat ggt act aag tat aat    240
Glu Trp Met Gly Tyr Ile Tyr Pro Tyr Asn Asp Gly Thr Lys Tyr Asn
 65                  70                  75                  80 gag aag ttc aag gac aga gtc acg atg acc cgg gac acg tcc acg agc    288
Glu Lys Phe Lys Asp Arg Val Thr Met Thr Arg Asp Thr Ser Thr Ser
                 85                  90                  95 aca gtc tac atg gag ttg agc agt ctc aga tct gag gac acg gcc gtc    336
Thr Val Tyr Met Glu Leu Ser Ser Leu Arg Ser Glu Asp Thr Ala Val
            100                 105                 110 tat tat tgt gct aga ggg ggt tac tat act tac gac gac tgg ggc caa    384
Tyr Tyr Cys Ala Arg Gly Gly Tyr Tyr Thr Tyr Asp Asp Trp Gly Gln
        115                 120                 125 gga acc ctg gtc acc gtc tcc tca ggtgagtgga tccgcg                  424
Gly Thr Leu Val Thr Val Ser Ser
    130                 135

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
gacagagtca cgatgacctc agacacgtcc acgagcacag         40

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
ggtcatcgtg actctgtc         18

<210> SEQ ID NO 10
<211> LENGTH: 424
<212> TYPE: DNA
<213> ORGANISM: Artificial Sequence
<220> FEATURE:
<223> OTHER INFORMATION: Description of Artificial Sequence: Synthetic plasmid
<220> FEATURE:
<221> NAME/KEY: CDS
<222> LOCATION: (1)..(408)

<400> SEQUENCE: 10

```
atg gaa tgg agc tgg ata ttt ctc ttc ctc ctg tca gga act gca ggt      48
Met Glu Trp Ser Trp Ile Phe Leu Phe Leu Leu Ser Gly Thr Ala Gly
 1               5                  10                  15 gtc cac tcc cag gtg cag ctg gtg cag tct ggg gct gag gtg aag aag      96
Val His Ser Gln Val Gln Leu Val Gln Ser Gly Ala Glu Val Lys Lys
             20                  25                  30 cct ggg gcc tca gtg aag gtt tcc tgt aag gca tct gga tac acc ttc     144
Pro Gly Ala Ser Val Lys Val Ser Cys Lys Ala Ser Gly Tyr Thr Phe
         35                  40                  45 gcc aac cat gtt att cac tgg gtg cga cag gcc cct gga caa ggg ctt     192
Ala Asn His Val Ile His Trp Val Arg Gln Ala Pro Gly Gln Gly Leu
     50                  55                  60 gag tgg atg gga tat att tat cct tac aat gat ggt act aag tat aat     240
Glu Trp Met Gly Tyr Ile Tyr Pro Tyr Asn Asp Gly Thr Lys Tyr Asn
 65                  70                  75                  80 gag aag ttc aag gac aga gtc acg atg acc tca gac acg tcc acg agc     288
Glu Lys Phe Lys Asp Arg Val Thr Met Thr Ser Asp Thr Ser Thr Ser
                 85                  90                  95 aca gtc tac atg gag ttg agc agt ctc aga tct gag gac acg gcc gtc     336
Thr Val Tyr Met Glu Leu Ser Ser Leu Arg Ser Glu Asp Thr Ala Val
            100                 105                 110 tat tat tgt gct aga ggg ggt tac tat act tac gac gac tgg ggc caa     384
Tyr Tyr Cys Ala Arg Gly Gly Tyr Tyr Thr Tyr Asp Asp Trp Gly Gln
        115                 120                 125 gga acc ctg gtc acc gtc tcc tca ggtgagtgga tccgcg                   424
Gly Thr Leu Val Thr Val Ser Ser
    130                 135
```

<210> SEQ ID NO 11

<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
gcatctggat acaccttcac caaccatgtt attcactggg     40

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
gaaggtgtat ccagatgc     18

<210> SEQ ID NO 13
<211> LENGTH: 424
<212> TYPE: DNA
<213> ORGANISM: Artificial Sequence
<220> FEATURE:
<223> OTHER INFORMATION: Description of Artificial Sequence: Synthetic plasmid
<220> FEATURE:
<221> NAME/KEY: CDS
<222> LOCATION: (1)..(408)

<400> SEQUENCE: 13

```
atg gaa tgg agc tgg ata ttt ctc ttc ctc ctg tca gga act gca ggt      48
Met Glu Trp Ser Trp Ile Phe Leu Phe Leu Leu Ser Gly Thr Ala Gly
 1               5                  10                  15 gtc cac tcc cag gtg cag ctg gtg cag tct ggg gct gag gtg aag aag      96
Val His Ser Gln Val Gln Leu Val Gln Ser Gly Ala Glu Val Lys Lys
             20                  25                  30 cct ggg gcc tca gtg aag gtt tcc tgt aag gca tct gga tac acc ttc     144
Pro Gly Ala Ser Val Lys Val Ser Cys Lys Ala Ser Gly Tyr Thr Phe
         35                  40                  45 acc aac cat gtt att cac tgg gtg cga cag gcc cct gga caa ggg ctt     192
Thr Asn His Val Ile His Trp Val Arg Gln Ala Pro Gly Gln Gly Leu
     50                  55                  60 gag tgg atg gga tat att tat cct tac aat gat ggt act aag tat aat     240
Glu Trp Met Gly Tyr Ile Tyr Pro Tyr Asn Asp Gly Thr Lys Tyr Asn
 65                  70                  75                  80 gag aag ttc aag gac aga gtc acg atg acc tca gac acg tcc acg agc     288
Glu Lys Phe Lys Asp Arg Val Thr Met Thr Ser Asp Thr Ser Thr Ser
                 85                  90                  95 aca gtc tac atg gag ttg agc agt ctc aga tct gag gac acg gcc gtc     336
Thr Val Tyr Met Glu Leu Ser Ser Leu Arg Ser Glu Asp Thr Ala Val
            100                 105                 110 tat tat tgt gct aga ggg ggt tac tat act tac gac gac tgg ggc caa     384
Tyr Tyr Cys Ala Arg Gly Gly Tyr Tyr Thr Tyr Asp Asp Trp Gly Gln
        115                 120                 125 gga acc ctg gtc acc gtc tcc tca ggtgagtgga tccgcg                   424
Gly Thr Leu Val Thr Val Ser Ser
    130                 135
```

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 14
aatgagaagt tcaaggacaa agtcacgatg acctcagac                     39

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 15
gtccttgaac ttctcatt                                            18

<210> SEQ ID NO 16
<211> LENGTH: 424
<212> TYPE: DNA
<213> ORGANISM: Artificial Sequence
<220> FEATURE:
<223> OTHER INFORMATION: Description of Artificial Sequence: Synthetic
    plasmid
<220> FEATURE:
<221> NAME/KEY: CDS
<222> LOCATION: (1)..(408)

<400> SEQUENCE: 16

```
atg gaa tgg agc tgg ata ttt ctc ttc ctc ctg tca gga act gca ggt    48
Met Glu Trp Ser Trp Ile Phe Leu Phe Leu Leu Ser Gly Thr Ala Gly
 1               5                  10                  15 gtc cac tcc cag gtg cag ctg gtg cag tct ggg gct gag gtg aag aag    96
Val His Ser Gln Val Gln Leu Val Gln Ser Gly Ala Glu Val Lys Lys
            20                  25                  30 cct ggg gcc tca gtg aag gtt tcc tgt aag gca tct gga tac acc ttc   144
Pro Gly Ala Ser Val Lys Val Ser Cys Lys Ala Ser Gly Tyr Thr Phe
        35                  40                  45 gcc aac cat gtt att cac tgg gtg cga cag gcc cct gga caa ggg ctt   192
Ala Asn His Val Ile His Trp Val Arg Gln Ala Pro Gly Gln Gly Leu
    50                  55                  60 gag tgg atg gga tat att tat cct tac aat gat ggt act aag tat aat   240
Glu Trp Met Gly Tyr Ile Tyr Pro Tyr Asn Asp Gly Thr Lys Tyr Asn
65                  70                  75                  80 gag aag ttc aag gac aaa gtc acg atg acc tca gac acg tcc acg agc   288
Glu Lys Phe Lys Asp Lys Val Thr Met Thr Ser Asp Thr Ser Thr Ser
                85                  90                  95 aca gtc tac atg gag ttg agc agt ctc aga tct gag gac acg gcc gtc   336
Thr Val Tyr Met Glu Leu Ser Ser Leu Arg Ser Glu Asp Thr Ala Val
            100                 105                 110 tat tat tgt gct aga ggg ggt tac tat act tac gac gac tgg ggc caa   384
Tyr Tyr Cys Ala Arg Gly Gly Tyr Tyr Thr Tyr Asp Asp Trp Gly Gln
        115                 120                 125 gga acc ctg gtc acc gtc tcc tca ggtgagtgga tccgcg                 424
Gly Thr Leu Val Thr Val Ser Ser
    130                 135
```

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
    oligonucleotide

<210> SEQ ID NO 17

<400> SEQUENCE: 17
ttcaaggaca gagtcacgct gacctcagac acgtccacg            39

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgtgactctg tccttgaa            18

<210> SEQ ID NO 19
<211> LENGTH: 424
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(408)

<400> SEQUENCE: 19

```
atg gaa tgg agc tgg ata ttt ctc ttc ctc ctg tca gga act gca ggt        48
Met Glu Trp Ser Trp Ile Phe Leu Phe Leu Leu Ser Gly Thr Ala Gly
 1               5                  10                  15 gtc cac tcc cag gtg cag ctg gtg cag tct ggg gct gag gtg aag aag        96
Val His Ser Gln Val Gln Leu Val Gln Ser Gly Ala Glu Val Lys Lys
             20                  25                  30 cct ggg gcc tca gtg aag gtt tcc tgt aag gca tct gga tac acc ttc       144
Pro Gly Ala Ser Val Lys Val Ser Cys Lys Ala Ser Gly Tyr Thr Phe
         35                  40                  45 gcc aac cat gtt att cac tgg gtg cga cag gcc cct gga caa ggg ctt       192
Ala Asn His Val Ile His Trp Val Arg Gln Ala Pro Gly Gln Gly Leu
     50                  55                  60 gag tgg atg gga tat att tat cct tac aat gat ggt act aag tat aat       240
Glu Trp Met Gly Tyr Ile Tyr Pro Tyr Asn Asp Gly Thr Lys Tyr Asn
 65                  70                  75                  80 gag aag ttc aag gac aga gtc acg ctg acc tca gac acg tcc acg agc       288
Glu Lys Phe Lys Asp Arg Val Thr Leu Thr Ser Asp Thr Ser Thr Ser
                 85                  90                  95 aca gtc tac atg gag ttg agc agt ctc aga tct gag gac acg gcc gtc       336
Thr Val Tyr Met Glu Leu Ser Ser Leu Arg Ser Glu Asp Thr Ala Val
            100                 105                 110 tat tat tgt gct aga ggg ggt tac tat act tac gac gac tgg ggc caa       384
Tyr Tyr Cys Ala Arg Gly Gly Tyr Tyr Thr Tyr Asp Asp Trp Gly Gln
        115                 120                 125 gga acc ctg gtc acc gtc tcc tca ggtgagtgga tccgcg                     424
Gly Thr Leu Val Thr Val Ser Ser
    130                 135
```

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gagcagtctc agatctgacg acacggccgt ctattattg                                39

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cgtcagatct gagactgctc                                                     20

<210> SEQ ID NO 22
<211> LENGTH: 424
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(408)

<400> SEQUENCE: 22

```
atg gaa tgg agc tgg ata ttt ctc ttc ctc ctg tca gga act gca ggt     48
Met Glu Trp Ser Trp Ile Phe Leu Phe Leu Leu Ser Gly Thr Ala Gly
 1               5                  10                  15 gtc cac tcc cag gtg cag ctg gtg cag tct ggg gct gag gtg aag aag     96
Val His Ser Gln Val Gln Leu Val Gln Ser Gly Ala Glu Val Lys Lys
             20                  25                  30 cct ggg gcc tca gtg aag gtt tcc tgt aag gca tct gga tac acc ttc    144
Pro Gly Ala Ser Val Lys Val Ser Cys Lys Ala Ser Gly Tyr Thr Phe
         35                  40                  45 acc aac cat gtt att cac tgg gtg cga cag gcc cct gga caa ggg ctt    192
Thr Asn His Val Ile His Trp Val Arg Gln Ala Pro Gly Gln Gly Leu
     50                  55                  60 gag tgg atg gga tat att tat cct tac aat gat ggt act aag tat aat    240
Glu Trp Met Gly Tyr Ile Tyr Pro Tyr Asn Asp Gly Thr Lys Tyr Asn
 65                  70                  75                  80 gag aag ttc aag gac aga gtc acg atg acc tca gac acg tcc acg agc    288
Glu Lys Phe Lys Asp Arg Val Thr Met Thr Ser Asp Thr Ser Thr Ser
                 85                  90                  95 aca gtc tac atg gag ttg agc agt ctc aga tct gac gac acg gcc gtc    336
Thr Val Tyr Met Glu Leu Ser Ser Leu Arg Ser Asp Asp Thr Ala Val
            100                 105                 110 tat tat tgt gct aga ggg ggt tac tat act tac gac gac tgg ggc caa    384
Tyr Tyr Cys Ala Arg Gly Gly Tyr Tyr Thr Tyr Asp Asp Trp Gly Gln
        115                 120                 125 gga acc ctg gtc acc gtc tcc tca ggtgagtgga tccgcg                  424
Gly Thr Leu Val Thr Val Ser Ser
    130                 135
```

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gaagcctggg gcctcagtgc aggtttcctg taagg                                    35

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaccatgtta ttcactggct gcgacaggcc cctggacaa                           39

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gatgacctca gacacgtcca tcagcacagc ctacatggag ttg                      43

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cactgaggcc ccaggcttc                                                 19

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ccagtgaata acatggtt                                                  18

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cgcggatcca ctcacctgag gagacggtga ccagggttgc ttggcccca               49

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggacgtgtct gaggtcatcg                                                20

<210> SEQ ID NO 30

<211> LENGTH: 424
<212> TYPE: DNA
<213> ORGANISM: Artificial Sequence
<220> FEATURE:
<223> OTHER INFORMATION: Description of Artificial Sequence: Synthetic plasmid
<220> FEATURE:
<221> NAME/KEY: CDS
<222> LOCATION: (1)..(408)

<400> SEQUENCE: 30

```
atg gaa tgg agc tgg ata ttt ctc ttc ctc ctg tca gga act gca ggt        48
Met Glu Trp Ser Trp Ile Phe Leu Phe Leu Leu Ser Gly Thr Ala Gly
  1               5                  10                  15 gtc cac tcc cag gtg cag ctg gtg cag tct ggg gct gag gtg aag aag        96
Val His Ser Gln Val Gln Leu Val Gln Ser Gly Ala Glu Val Lys Lys
             20                  25                  30 cct ggg gcc tca gtg cag gtt tcc tgt aag gca tct gga tac acc ttc       144
Pro Gly Ala Ser Val Gln Val Ser Cys Lys Ala Ser Gly Tyr Thr Phe
         35                  40                  45 acc aac cat gtt att cac tgg ctg cga cag gcc cct gga caa ggg ctt       192
Thr Asn His Val Ile His Trp Leu Arg Gln Ala Pro Gly Gln Gly Leu
     50                  55                  60 gag tgg atg gga tat att tat cct tac aat gat ggt act aag tat aat       240
Glu Trp Met Gly Tyr Ile Tyr Pro Tyr Asn Asp Gly Thr Lys Tyr Asn
 65                  70                  75                  80 gag aag ttc aag gac aga gtc acg atg acc tca gac acg tcc atc agc       288
Glu Lys Phe Lys Asp Arg Val Thr Met Thr Ser Asp Thr Ser Ile Ser
                 85                  90                  95 aca gcc tac atg gag ttg agc agt ctc aga tct gac gac acg gcc gtc       336
Thr Ala Tyr Met Glu Leu Ser Ser Leu Arg Ser Asp Asp Thr Ala Val
            100                 105                 110 tat tat tgt gct aga ggg ggt tac tat act tac gac gac tgg ggc caa       384
Tyr Tyr Cys Ala Arg Gly Gly Tyr Tyr Thr Tyr Asp Asp Trp Gly Gln
        115                 120                 125 gca acc ctg gtc acc gtc tcc tca ggtgagtgga tccgcg                     424
Ala Thr Leu Val Thr Val Ser Ser
    130                 135
```

<210> SEQ ID NO 31
<211> LENGTH: 130
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31

```
cccaagcttc caccatgagg ctccctgctc agctcctggg gctgctaatg ctctgggtcc      60
caggctccag tggggatgtt gtgatgactc agtctccact ctcctgcccc gtcacccttg     120
gacagccggc                                                            130
```

<210> SEQ ID NO 32
<211> LENGTH: 130
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32

```
cagcagaggc caggccaatc tccaaggcgc ctaatttata aagtttccaa ccgattttct      60
ggtgtcccag acagattcag cggcagtggg tcaggcactg atttcacact gaaaatcagc     120
```

-continued

```
agggtggagg                                                           130

<210> SEQ ID NO 33
<211> LENGTH: 130
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggcgccttgg agattggcct ggcctctgct gaaaccaatg taaataggtc tttccattac    60
tgtgcacaag gctctgactt gatctgcagg agatggaggc cggctgtcca agggtgacgg   120
gcagggagag                                                          130

<210> SEQ ID NO 34
<211> LENGTH: 130
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgcggatcca ctcacgtttg atctccagct tggtcccctg gccaaacgtg tacggaacat    60
gtgtactttg agagcagtaa taaactccaa catcctcagc ctccaccctg ctgattttca   120
gtgtgaaatc                                                          130

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cccaagcttc caccatgagg ctc                                            23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgcggatcca ctcacgtttg atc                                            23

<210> SEQ ID NO 37
<211> LENGTH: 412
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(396)

<400> SEQUENCE: 37 atg agg ctc cct gct cag ctc ctg ggg ctg cta atg ctc tgg gtc cca     48
Met Arg Leu Pro Ala Gln Leu Leu Gly Leu Leu Met Leu Trp Val Pro
```

```
ggc tcc agt ggg gat gtt gtg atg act cag tct cca ctc tcc ctg ccc      96
Gly Ser Ser Gly Asp Val Val Met Thr Gln Ser Pro Leu Ser Leu Pro
             20                  25                  30 gtc acc ctt gga cag ccg gcc tcc atc tcc tgc aga tca agt cag agc     144
Val Thr Leu Gly Gln Pro Ala Ser Ile Ser Cys Arg Ser Ser Gln Ser
     35                  40                  45 ctt gtg cac agt aat gga aag acc tat tta cat tgg ttt cag cag agg     192
Leu Val His Ser Asn Gly Lys Thr Tyr Leu His Trp Phe Gln Gln Arg
 50                  55                  60 cca ggc caa tct cca agg cgc cta att tat aaa gtt tcc aac cga ttt     240
Pro Gly Gln Ser Pro Arg Arg Leu Ile Tyr Lys Val Ser Asn Arg Phe
65                  70                  75                  80 tct ggt gtc cca gac aga ttc agc ggc agt ggg tca ggc act gat ttc     288
Ser Gly Val Pro Asp Arg Phe Ser Gly Ser Gly Ser Gly Thr Asp Phe
                 85                  90                  95 aca ctg aaa atc agc agg gtg gag gct gag gat gtt gga gtt tat tac     336
Thr Leu Lys Ile Ser Arg Val Glu Ala Glu Asp Val Gly Val Tyr Tyr
             100                 105                 110 tgc tct caa agt aca cat gtt ccg tac acg ttt ggc cag ggg acc aag     384
Cys Ser Gln Ser Thr His Val Pro Tyr Thr Phe Gly Gln Gly Thr Lys
         115                 120                 125 ctg gag atc aaa cgtgagtgga tccgcg                                   412
Leu Glu Ile Lys
    130

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ccaggccaat ctccaaggct cctaatttat aaagtttcc                           39

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccttggagat tggcctgg                                                  18

<210> SEQ ID NO 40
<211> LENGTH: 412
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(396)

<400> SEQUENCE: 40 atg agg ctc cct gct cag ctc ctg ggg ctg cta atg ctc tgg gtc cca      48
Met Arg Leu Pro Ala Gln Leu Leu Gly Leu Leu Met Leu Trp Val Pro
 1               5                  10                  15 ggc tcc agt ggg gat gtt gtg atg act cag tct cca ctc tcc ctg ccc      96
```

```
Gly Ser Ser Gly Asp Val Val Met Thr Gln Ser Pro Leu Ser Leu Pro
                20                  25                  30 gtc acc ctt gga cag ccg gcc tcc atc tcc tgc aga tca agt cag agc    144
Val Thr Leu Gly Gln Pro Ala Ser Ile Ser Cys Arg Ser Ser Gln Ser
            35                  40                  45 ctt gtg cac agt aat gga aag acc tat tta cat tgg ttt cag cag agg    192
Leu Val His Ser Asn Gly Lys Thr Tyr Leu His Trp Phe Gln Gln Arg
    50                  55                  60 cca ggc caa tct cca agg ctc cta att tat aaa gtt tcc aac cga ttt    240
Pro Gly Gln Ser Pro Arg Leu Leu Ile Tyr Lys Val Ser Asn Arg Phe
65                  70                  75                  80 tct ggt gtc cca gac aga ttc agc ggc agt ggg tca ggc act gat ttc    288
Ser Gly Val Pro Asp Arg Phe Ser Gly Ser Gly Ser Gly Thr Asp Phe
                85                  90                  95 aca ctg aaa atc agc agg gtg gag gct gag gat gtt gga gtt tat tac    336
Thr Leu Lys Ile Ser Arg Val Glu Ala Glu Asp Val Gly Val Tyr Tyr
            100                 105                 110 tgc tct caa agt aca cat gtt ccg tac acg ttt ggc cag ggg acc aag    384
Cys Ser Gln Ser Thr His Val Pro Tyr Thr Phe Gly Gln Gly Thr Lys
    115                 120                 125 ctg gag atc aaa cgtgagtgga tccgcg                                  412
Leu Glu Ile Lys
        130
```

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gaggatgttg gagtttattt ctgctctcaa agtacacat                         39

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ataaactcca acatcctc                                                18

<210> SEQ ID NO 43
<211> LENGTH: 412
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(396)

<400> SEQUENCE: 43

```
atg agg ctc cct gct cag ctc ctg ggg ctg cta atg ctc tgg gtc cca    48
Met Arg Leu Pro Ala Gln Leu Leu Gly Leu Leu Met Leu Trp Val Pro
1               5                   10                  15 ggc tcc agt ggg gat gtt gtg atg act cag tct cca ctc tcc ctg ccc    96
Gly Ser Ser Gly Asp Val Val Met Thr Gln Ser Pro Leu Ser Leu Pro
                20                  25                  30
```

```
gtc acc ctt gga cag ccg gcc tcc atc tcc tgc aga tca agt cag agc      144
Val Thr Leu Gly Gln Pro Ala Ser Ile Ser Cys Arg Ser Ser Gln Ser
        35                  40                  45 ctt gtg cac agt aat gga aag acc tat tta cat tgg ttt cag cag agg      192
Leu Val His Ser Asn Gly Lys Thr Tyr Leu His Trp Phe Gln Gln Arg
    50                  55                  60 cca ggc caa tct cca agg cgc cta att tat aaa gtt tcc aac cga ttt      240
Pro Gly Gln Ser Pro Arg Arg Leu Ile Tyr Lys Val Ser Asn Arg Phe
65                  70                  75                  80 tct ggt gtc cca gac aga ttc agc ggc agt ggg tca ggc act gat ttc      288
Ser Gly Val Pro Asp Arg Phe Ser Gly Ser Gly Ser Gly Thr Asp Phe
                85                  90                  95 aca ctg aaa atc agc agg gtg gag gct gag gat gtt gga gtt tat ttc      336
Thr Leu Lys Ile Ser Arg Val Glu Ala Glu Asp Val Gly Val Tyr Phe
            100                 105                 110 tgc tct caa agt aca cat gtt ccg tac acg ttt ggc cag ggg acc aag      384
Cys Ser Gln Ser Thr His Val Pro Tyr Thr Phe Gly Gln Gly Thr Lys
        115                 120                 125 ctg gag atc aaa cgtgagtgga tccgcg                                    412
Leu Glu Ile Lys
    130

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aagacctatt tacattggta ccagcagagg ccaggccaa                            39

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccaatgtaaa taggtctttc                                                 20

<210> SEQ ID NO 46
<211> LENGTH: 412
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(396)

<400> SEQUENCE: 46 atg agg ctc cct gct cag ctc ctg ggg ctg cta atg ctc tgg gtc cca       48
Met Arg Leu Pro Ala Gln Leu Leu Gly Leu Leu Met Leu Trp Val Pro
1               5                   10                  15 ggc tcc agt ggg gat gtt gtg atg act cag tct cca ctc tcc ctg ccc       96
Gly Ser Ser Gly Asp Val Val Met Thr Gln Ser Pro Leu Ser Leu Pro
                20                  25                  30 gtc acc ctt gga cag ccg gcc tcc atc tcc tgc aga tca agt cag agc      144
Val Thr Leu Gly Gln Pro Ala Ser Ile Ser Cys Arg Ser Ser Gln Ser
        35                  40                  45
```

```
ctt gtg cac agt aat gga aag acc tat tta cat tgg tac cag cag agg      192
Leu Val His Ser Asn Gly Lys Thr Tyr Leu His Trp Tyr Gln Gln Arg
        50                  55                  60 cca ggc caa tct cca agg cgc cta att tat aaa gtt tcc aac cga ttt      240
Pro Gly Gln Ser Pro Arg Arg Leu Ile Tyr Lys Val Ser Asn Arg Phe
 65                  70                  75                  80 tct ggt gtc cca gac aga ttc agc ggc agt ggg tca ggc act gat ttc      288
Ser Gly Val Pro Asp Arg Phe Ser Gly Ser Gly Ser Gly Thr Asp Phe
                 85                  90                  95 aca ctg aaa atc agc agg gtg gag gct gag gat gtt gga gtt tat tac      336
Thr Leu Lys Ile Ser Arg Val Glu Ala Glu Asp Val Gly Val Tyr Tyr
            100                 105                 110 tgc tct caa agt aca cat gtt ccg tac acg ttt ggc cag ggg acc aag      384
Cys Ser Gln Ser Thr His Val Pro Tyr Thr Phe Gly Gln Gly Thr Lys
        115                 120                 125 ctg gag atc aaa cgtgagtgga tccgcg                                    412
Leu Glu Ile Lys
    130
```

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cctatttaca ttggtttctg cagaggccag gccaatctc                            39

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gaaaccaatg taaataggtc                                                 20

<210> SEQ ID NO 49
<211> LENGTH: 412
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(396)

<400> SEQUENCE: 49

```
atg agg ctc cct gct cag ctc ctg ggg ctg cta atg ctc tgg gtc cca       48
Met Arg Leu Pro Ala Gln Leu Leu Gly Leu Leu Met Leu Trp Val Pro
 1               5                  10                  15 ggc tcc agt ggg gat gtt gtg atg act cag tct cca ctc tcc ctg ccc       96
Gly Ser Ser Gly Asp Val Val Met Thr Gln Ser Pro Leu Ser Leu Pro
                 20                  25                  30 gtc acc ctt gga cag ccg gcc tcc atc tcc tgc aga tca agt cag agc      144
Val Thr Leu Gly Gln Pro Ala Ser Ile Ser Cys Arg Ser Ser Gln Ser
            35                  40                  45 ctt gtg cac agt aat gga aag acc tat tta cat tgg ttt ctg cag agg      192
Leu Val His Ser Asn Gly Lys Thr Tyr Leu His Trp Phe Leu Gln Arg
        50                  55                  60
```

```
cca ggc caa tct cca agg cgc cta att tat aaa gtt tcc aac cga ttt      240
Pro Gly Gln Ser Pro Arg Arg Leu Ile Tyr Lys Val Ser Asn Arg Phe
 65                  70                  75                  80 tct ggt gtc cca gac aga ttc agc ggc agt ggg tca ggc act gat ttc      288
Ser Gly Val Pro Asp Arg Phe Ser Gly Ser Gly Ser Gly Thr Asp Phe
                 85                  90                  95 aca ctg aaa atc agc agg gtg gag gct gag gat gtt gga gtt tat tac      336
Thr Leu Lys Ile Ser Arg Val Glu Ala Glu Asp Val Gly Val Tyr Tyr
            100                 105                 110 tgc tct caa agt aca cat gtt ccg tac acg ttt ggc cag ggg acc aag      384
Cys Ser Gln Ser Thr His Val Pro Tyr Thr Phe Gly Gln Gly Thr Lys
        115                 120                 125 ctg gag atc aaa cgtgagtgga tccgcg                                    412
Leu Glu Ile Lys
    130

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cagaagccag gccagtctcc aagactcctg atctacaaag                           40

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggagactggc ctggcttctg cagataccaa tgtaaatagg                           40

<210> SEQ ID NO 52
<211> LENGTH: 412
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(396)

<400> SEQUENCE: 52 atg agg ctc cct gct cag ctc ctg ggg ctg cta atg ctc tgg gtc cca       48
Met Arg Leu Pro Ala Gln Leu Leu Gly Leu Leu Met Leu Trp Val Pro
  1               5                  10                  15 ggc tcc agt ggg gat gtt gtg atg act cag tct cca ctc tcc ctg ccc       96
Gly Ser Ser Gly Asp Val Val Met Thr Gln Ser Pro Leu Ser Leu Pro
             20                  25                  30 gtc acc ctt gga cag ccg gcc tcc atc tcc tgc aga tca agt cag agc      144
Val Thr Leu Gly Gln Pro Ala Ser Ile Ser Cys Arg Ser Ser Gln Ser
         35                  40                  45 ctt gtg cac agt aat gga aag acc tat tta cat tgg tat ctg cag aag      192
Leu Val His Ser Asn Gly Lys Thr Tyr Leu His Trp Tyr Leu Gln Lys
     50                  55                  60 cca ggc cag tct cca aga ctc ctg atc tac aaa gtt tcc aac cga ttt      240
```

```
                Pro Gly Gln Ser Pro Arg Leu Leu Ile Tyr Lys Val Ser Asn Arg Phe
                 65                  70                  75                  80 tct ggt gtc cca gac aga ttc agc ggc agt ggg tca ggc act gat ttc           288
Ser Gly Val Pro Asp Arg Phe Ser Gly Ser Gly Ser Gly Thr Asp Phe
                     85                  90                  95 aca ctg aaa atc agc agg gtg gag gct gag gat gtt gga gtt tat tac           336
Thr Leu Lys Ile Ser Arg Val Glu Ala Glu Asp Val Gly Val Tyr Tyr
            100                 105                 110 tgc tct caa agt aca cat gtt ccg tac acg ttt ggc cag ggg acc aag           384
Cys Ser Gln Ser Thr His Val Pro Tyr Thr Phe Gly Gln Gly Thr Lys
        115                 120                 125 ctg gag atc aaa cgtgagtgga tccgcg                                         412
Leu Glu Ile Lys
    130

<210> SEQ ID NO 53
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cagtctccac tctccctgcc cgtcacccct ggagagccgg cctccatctc ctgc             54

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gggtggaggc tgatgatgtt ggaatttatt actgctctc                              39

<210> SEQ ID NO 55
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cagggagagt ggagactgag tcatcacaat atccccactg agcctgg                     48

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ccaacatcat cagcctccac cc                                                22

<210> SEQ ID NO 57
<211> LENGTH: 412
<212> TYPE: DNA
<213> ORGANISM: Artificial Sequence
<220> FEATURE:
<223> OTHER INFORMATION: Description of Artificial Sequence: Synthetic
      plasmid
```

```
<220> FEATURE:
<221> NAME/KEY: CDS
<222> LOCATION: (1)..(396)

<400> SEQUENCE: 57 atg agg ctc cct gct cag ctc ctg ggg ctg cta atg ctc tgg gtc cca      48
Met Arg Leu Pro Ala Gln Leu Leu Gly Leu Leu Met Leu Trp Val Pro
 1               5                  10                  15 ggc tcc agt ggg gat att gtg atg act cag tct cca ctc tcc ctg ccc      96
Gly Ser Ser Gly Asp Ile Val Met Thr Gln Ser Pro Leu Ser Leu Pro
            20                  25                  30 gtc acc cct gga gag ccg gcc tcc atc tcc tgc aga tca agt cag agc     144
Val Thr Pro Gly Glu Pro Ala Ser Ile Ser Cys Arg Ser Ser Gln Ser
        35                  40                  45 ctt gtg cac agt aat gga aag acc tat tta cat tgg tat ctg cag aag     192
Leu Val His Ser Asn Gly Lys Thr Tyr Leu His Trp Tyr Leu Gln Lys
    50                  55                  60 cca ggc cag tct cca aga ctc ctg atc tac aaa gtt tcc aac cga ttt     240
Pro Gly Gln Ser Pro Arg Leu Leu Ile Tyr Lys Val Ser Asn Arg Phe
65                  70                  75                  80 tct ggt gtc cca gac aga ttc agc ggc agt ggg tca ggc act gat ttc     288
Ser Gly Val Pro Asp Arg Phe Ser Gly Ser Gly Ser Gly Thr Asp Phe
                85                  90                  95 aca ctg aaa atc agc agg gtg gag gct gat gat gtt gga att tat tac     336
Thr Leu Lys Ile Ser Arg Val Glu Ala Asp Asp Val Gly Ile Tyr Tyr
            100                 105                 110 tgc tct caa agt aca cat gtt ccg tac acg ttt ggc cag ggg acc aag     384
Cys Ser Gln Ser Thr His Val Pro Tyr Thr Phe Gly Gln Gly Thr Lys
        115                 120                 125 ctg gag atc aaa cgtgagtgga tccgcg                                   412
Leu Glu Ile Lys
    130

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ccttcaccaa ccatgttatg cactggctgc gacaggcc                            38

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ataatgagaa gttcaagggc agagtcacga tgacctca                            38

<210> SEQ ID NO 60
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
```

```
tgctagaggg ggttactatt cttacgacga ctgggggcc                            38
```

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
ataacatggt tggtgaaggt                                                  20
```

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
ccttgaactt ctcattatac                                                  20
```

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
atagtaaccc cctctagca                                                   19
```

<210> SEQ ID NO 64
<211> LENGTH: 424
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(408)

<400> SEQUENCE: 64

```
atg gaa tgg agc tgg ata ttt ctc ttc ctc ctg tca gga act gca ggt        48
Met Glu Trp Ser Trp Ile Phe Leu Phe Leu Leu Ser Gly Thr Ala Gly
 1               5                  10                  15 gtc cac tcc cag gtg cag ctg gtg cag tct ggg gct gag gtg aag aag        96
Val His Ser Gln Val Gln Leu Val Gln Ser Gly Ala Glu Val Lys Lys
             20                  25                  30 cct ggg gcc tca gtg cag gtt tcc tgt aag gca tct gga tac acc ttc       144
Pro Gly Ala Ser Val Gln Val Ser Cys Lys Ala Ser Gly Tyr Thr Phe
         35                  40                  45 acc aac cat gtt atg cac tgg ctg cga cag gcc cct gga caa ggg ctt       192
Thr Asn His Val Met His Trp Leu Arg Gln Ala Pro Gly Gln Gly Leu
     50                  55                  60 gag tgg atg gga tat att tat cct tac aat gat ggt act aag tat aat       240
Glu Trp Met Gly Tyr Ile Tyr Pro Tyr Asn Asp Gly Thr Lys Tyr Asn
 65                  70                  75                  80 gag aag ttc aag ggc aga gtc acg atg acc tca gac acg tcc atc agc       288
Glu Lys Phe Lys Gly Arg Val Thr Met Thr Ser Asp Thr Ser Ile Ser
                 85                  90                  95
```

```
aca gcc tac atg gag ttg agc agt ctc aga tct gac gac acg gcc gtc      336
Thr Ala Tyr Met Glu Leu Ser Ser Leu Arg Ser Asp Asp Thr Ala Val
            100                 105                 110 tat tat tgt gct aga ggg ggt tac tat tct tac gac gac tgg ggc caa      384
Tyr Tyr Cys Ala Arg Gly Gly Tyr Tyr Ser Tyr Asp Asp Trp Gly Gln
        115                 120                 125 gca acc ctg gtc acc gtc tcc tca ggtgagtgga tccgcg                     424
Ala Thr Leu Val Thr Val Ser Ser
    130                 135

<210> SEQ ID NO 65
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
acagtaaggg aaacacctat ttacagtggt atctgcaga                             39

<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ataggtgttt cccttactgt gcagaaggct ctgacttga                             39

<210> SEQ ID NO 67
<211> LENGTH: 412
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(396)

<400> SEQUENCE: 67 atg agg ctc cct gct cag ctc ctg ggg ctg cta atg ctc tgg gtc cca       48
Met Arg Leu Pro Ala Gln Leu Leu Gly Leu Leu Met Leu Trp Val Pro
1               5                   10                  15 ggc tcc agt ggg gat att gtg atg act cag tct cca ctc tcc ctg ccc       96
Gly Ser Ser Gly Asp Ile Val Met Thr Gln Ser Pro Leu Ser Leu Pro
            20                  25                  30 gtc acc cct gga gag ccg gcc tcc atc tcc tgc aga tca agt cag agc      144
Val Thr Pro Gly Glu Pro Ala Ser Ile Ser Cys Arg Ser Ser Gln Ser
        35                  40                  45 ctt ctg cac agt aag gga aac acc tat tta cag tgg tat ctg cag aag      192
Leu Leu His Ser Lys Gly Asn Thr Tyr Leu Gln Trp Tyr Leu Gln Lys
    50                  55                  60 cca ggc cag tct cca aga ctc ctg atc tac aaa gtt tcc aac cga ttt      240
Pro Gly Gln Ser Pro Arg Leu Leu Ile Tyr Lys Val Ser Asn Arg Phe
65                  70                  75                  80 tct ggt gtc cca gac aga ttc agc ggc agt ggg tca ggc act gat ttc      288
Ser Gly Val Pro Asp Arg Phe Ser Gly Ser Gly Ser Gly Thr Asp Phe
                85                  90                  95 aca ctg aaa atc agc agg gtg gag gct gat gat gtt gga att tat tac      336
Thr Leu Lys Ile Ser Arg Val Glu Ala Asp Asp Val Gly Ile Tyr Tyr
            100                 105                 110
```

```
tgc tct caa agt aca cat gtt ccg tac acg ttt ggc cag ggg acc aag      384
Cys Ser Gln Ser Thr His Val Pro Tyr Thr Phe Gly Gln Gly Thr Lys
        115                 120                 125 ctg gag atc aaa cgtgagtgga tccgcg                                    412
Leu Glu Ile Lys
    130
```

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aggtgtcgac tcccaggtgc agctg                                           25

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ccaccactcg agactgtgac cagggttgct tggcc                                35

<210> SEQ ID NO 70
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cagtctcgag tggtggcgga ggttccgata ttgtgatgac tcag                      44

<210> SEQ ID NO 71
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aaaaggaaaa gcggccgctc attatttgat ctccagcttg gtcccc                    46

<210> SEQ ID NO 72
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 72

```
ggt ggc gga ggt tcc                                                   15
Gly Gly Gly Gly Ser
 1               5
```

<210> SEQ ID NO 73
<211> LENGTH: 768
<212> TYPE: DNA
<213> ORGANISM: Artificial Sequence
<220> FEATURE:
<223> OTHER INFORMATION: Description of Artificial Sequence: Synthetic plasmid
<220> FEATURE:
<221> NAME/KEY: CDS
<222> LOCATION: (1)..(759)

<400> SEQUENCE: 73

```
atg gga tgg agc tgt atc atc ctc ttc ttg gta gca aca gct aca ggt      48
Met Gly Trp Ser Cys Ile Ile Leu Phe Leu Val Ala Thr Ala Thr Gly
 1               5                  10                  15 gtc gac tcc cag gtg cag ctg gtg cag tct ggg gct gag gtg aag aag      96
Val Asp Ser Gln Val Gln Leu Val Gln Ser Gly Ala Glu Val Lys Lys
             20                  25                  30 cct ggg gcc tca gtg cag gtt tcc tgt aag gca tct gga tac acc ttc     144
Pro Gly Ala Ser Val Gln Val Ser Cys Lys Ala Ser Gly Tyr Thr Phe
         35                  40                  45 acc aac cat gtt att cac tgg ctg cga cag gcc cct gga caa ggg ctt     192
Thr Asn His Val Ile His Trp Leu Arg Gln Ala Pro Gly Gln Gly Leu
     50                  55                  60 gag tgg atg gga tat att tat cct tac aat gat ggt act aag tat aat     240
Glu Trp Met Gly Tyr Ile Tyr Pro Tyr Asn Asp Gly Thr Lys Tyr Asn
 65                  70                  75                  80 gag aag ttc aag gac aga gtc acg atg acc tca gac acg tcc atc agc     288
Glu Lys Phe Lys Asp Arg Val Thr Met Thr Ser Asp Thr Ser Ile Ser
                 85                  90                  95 aca gcc tac atg gag ttg agc agt ctc aga tct gac gac acg gcc gtc     336
Thr Ala Tyr Met Glu Leu Ser Ser Leu Arg Ser Asp Asp Thr Ala Val
            100                 105                 110 tat tat tgt gct aga ggg ggt tac tat act tac gac gac tgg ggc caa     384
Tyr Tyr Cys Ala Arg Gly Gly Tyr Tyr Thr Tyr Asp Asp Trp Gly Gln
        115                 120                 125 gca acc ctg gtc aca gtc tcg agt ggt ggc gga ggt tcc gat att gtg     432
Ala Thr Leu Val Thr Val Ser Ser Gly Gly Gly Gly Ser Asp Ile Val
    130                 135                 140 atg act cag tct cca ctc tcc ctg ccc gtc acc cct gga gag ccg gcc     480
Met Thr Gln Ser Pro Leu Ser Leu Pro Val Thr Pro Gly Glu Pro Ala
145                 150                 155                 160 tcc atc tcc tgc aga tca agt cag agc ctt gta cac agt aat gga aag     528
Ser Ile Ser Cys Arg Ser Ser Gln Ser Leu Val His Ser Asn Gly Lys
                165                 170                 175 acc tat tta cat tgg tat ctg cag aag cca ggc cag tct cca aga ctc     576
Thr Tyr Leu His Trp Tyr Leu Gln Lys Pro Gly Gln Ser Pro Arg Leu
            180                 185                 190 ctg atc tac aaa gtt tcc aac cga ttt tct ggt gtc cca gac aga ttc     624
Leu Ile Tyr Lys Val Ser Asn Arg Phe Ser Gly Val Pro Asp Arg Phe
        195                 200                 205 agc ggc agt ggg tca ggc act gat ttc aca ctg aaa atc agc agg gtg     672
Ser Gly Ser Gly Ser Gly Thr Asp Phe Thr Leu Lys Ile Ser Arg Val
    210                 215                 220 gag gct gat gat gtt gga att tat tac tgc tct caa agt aca cat gtt     720
Glu Ala Asp Asp Val Gly Ile Tyr Tyr Cys Ser Gln Ser Thr His Val
225                 230                 235                 240 ccg tac acg ttt ggc cag ggg acc aag ctg gag atc aaa taatgagcg       768
Pro Tyr Thr Phe Gly Gln Gly Thr Lys Leu Glu Ile Lys
                245                 250
```

<210> SEQ ID NO 74
<211> LENGTH: 768
<212> TYPE: DNA
<213> ORGANISM: Artificial Sequence
<220> FEATURE:
<223> OTHER INFORMATION: Description of Artificial Sequence: Synthetic plasmid
<220> FEATURE:
<221> NAME/KEY: CDS
<222> LOCATION: (1)..(759)

<400> SEQUENCE: 74

```
atg gga tgg agc tgt atc atc ctc ttc ttg gta gca aca gct aca ggt     48
Met Gly Trp Ser Cys Ile Ile Leu Phe Leu Val Ala Thr Ala Thr Gly
 1               5                  10                  15 gtc gac tcc cag gtg cag ctg gtg cag tct ggg gct gag gtg aag aag     96
Val Asp Ser Gln Val Gln Leu Val Gln Ser Gly Ala Glu Val Lys Lys
             20                  25                  30 cct ggg gcc tca gtg cag gtt tcc tgt aag gca tct gga tac acc ttc    144
Pro Gly Ala Ser Val Gln Val Ser Cys Lys Ala Ser Gly Tyr Thr Phe
         35                  40                  45 acc aac cat gtt atg cac tgg ctg cga cag gcc cct gga caa ggg ctt    192
Thr Asn His Val Met His Trp Leu Arg Gln Ala Pro Gly Gln Gly Leu
     50                  55                  60 gag tgg atg gga tat att tat cct tac aat gat ggt act aag tat aat    240
Glu Trp Met Gly Tyr Ile Tyr Pro Tyr Asn Asp Gly Thr Lys Tyr Asn
 65                  70                  75                  80 gag aag ttc aag ggc aga gtc acg atg acc tca gac acg tcc atc agc    288
Glu Lys Phe Lys Gly Arg Val Thr Met Thr Ser Asp Thr Ser Ile Ser
                 85                  90                  95 aca gcc tac atg gag ttg agc agt ctc aga tct gac gac acg gcc gtc    336
Thr Ala Tyr Met Glu Leu Ser Ser Leu Arg Ser Asp Asp Thr Ala Val
            100                 105                 110 tat tat tgt gct aga ggg ggt tac tat tct tac gac gac tgg ggc caa    384
Tyr Tyr Cys Ala Arg Gly Gly Tyr Tyr Ser Tyr Asp Asp Trp Gly Gln
        115                 120                 125 gca acc ctg gtc aca gtc tcg agt ggt ggc gga ggt tcc gat att gtg    432
Ala Thr Leu Val Thr Val Ser Ser Gly Gly Gly Gly Ser Asp Ile Val
    130                 135                 140 atg act cag tct cca ctc tcc ctg ccc gtc acc cct gga gag ccg gcc    480
Met Thr Gln Ser Pro Leu Ser Leu Pro Val Thr Pro Gly Glu Pro Ala
145                 150                 155                 160 tcc atc tcc tgc aga tca agt cag agc ctt ctg cac agt aag gga aac    528
Ser Ile Ser Cys Arg Ser Ser Gln Ser Leu Leu His Ser Lys Gly Asn
                165                 170                 175 acc tat tta cag tgg tat ctg cag aag cca ggc cag tct cca aga ctc    576
Thr Tyr Leu Gln Trp Tyr Leu Gln Lys Pro Gly Gln Ser Pro Arg Leu
            180                 185                 190 ctg atc tac aaa gtt tcc aac cga ttt tct ggt gtc cca gac aga ttc    624
Leu Ile Tyr Lys Val Ser Asn Arg Phe Ser Gly Val Pro Asp Arg Phe
        195                 200                 205 agc ggc agt ggg tca ggc act gat ttc aca ctg aaa atc agc agg gtg    672
Ser Gly Ser Gly Ser Gly Thr Asp Phe Thr Leu Lys Ile Ser Arg Val
    210                 215                 220 gag gct gat gat gtt gga att tat tac tgc tct caa agt aca cat gtt    720
Glu Ala Asp Asp Val Gly Ile Tyr Tyr Cys Ser Gln Ser Thr His Val
225                 230                 235                 240 ccg tac acg ttt ggc cag ggg acc aag ctg gag atc aaa taatgagcg      768
Pro Tyr Thr Phe Gly Gln Gly Thr Lys Leu Glu Ile Lys
                245                 250
```

<210> SEQ ID NO 75

```
<210> SEQ ID NO 75
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cgcggatccg gtggtggcgg atcgcaggtg cagctggtgc agtc                44

<210> SEQ ID NO 76
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cgcggatcca ccaccacccg aaccaccacc acctttgatc tccagcttgg tccc      54

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 77 ggt ggt ggt ggt tcg ggt ggt ggt gga tcc ggt ggt ggc gga tcg      45
Gly Gly Gly Gly Ser Gly Gly Gly Gly Ser Gly Gly Gly Gly Ser
1               5                   10                  15

<210> SEQ ID NO 78
<211> LENGTH: 1515
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(1506)

<400> SEQUENCE: 78 atg gga tgg agc tgt atc atc ctc ttc ttg gta gca aca gct aca ggt    48
Met Gly Trp Ser Cys Ile Ile Leu Phe Leu Val Ala Thr Ala Thr Gly
1               5                   10                  15 gtc gac tcc cag gtg cag ctg gtg cag tct ggg gct gag gtg aag aag    96
Val Asp Ser Gln Val Gln Leu Val Gln Ser Gly Ala Glu Val Lys Lys
                20                  25                  30 cct ggg gcc tca gtg cag gtt tcc tgt aag gca tct gga tac acc ttc   144
Pro Gly Ala Ser Val Gln Val Ser Cys Lys Ala Ser Gly Tyr Thr Phe
            35                  40                  45 acc aac cat gtt att cac tgg ctg cga cag gcc cct gga caa ggg ctt   192
Thr Asn His Val Ile His Trp Leu Arg Gln Ala Pro Gly Gln Gly Leu
        50                  55                  60 gag tgg atg gga tat att tat cct tac aat gat ggt act aag tat aat   240
Glu Trp Met Gly Tyr Ile Tyr Pro Tyr Asn Asp Gly Thr Lys Tyr Asn
65                  70                  75                  80 gag aag ttc aag gac aga gtc acg atg acc tca gac acg tcc atc agc   288
Glu Lys Phe Lys Asp Arg Val Thr Met Thr Ser Asp Thr Ser Ile Ser
                85                  90                  95
```

| | | |
|---|---|---|
| aca gcc tac atg gag ttg agc agt ctc aga tct gac gac acg gcc gtc | 336 | |
| Thr Ala Tyr Met Glu Leu Ser Ser Leu Arg Ser Asp Asp Thr Ala Val | | |
| 100 105 110 | | |
| tat tat tgt gct aga ggg ggt tac tat act tac gac gac tgg ggc caa | 384 | |
| Tyr Tyr Cys Ala Arg Gly Gly Tyr Tyr Thr Tyr Asp Asp Trp Gly Gln | | |
| 115 120 125 | | |
| gca acc ctg gtc aca gtc tcg agt ggt ggc gga ggt tcc gat att gtg | 432 | |
| Ala Thr Leu Val Thr Val Ser Ser Gly Gly Gly Gly Ser Asp Ile Val | | |
| 130 135 140 | | |
| atg act cag tct cca ctc tcc ctg ccc gtc acc cct gga gag ccg gcc | 480 | |
| Met Thr Gln Ser Pro Leu Ser Leu Pro Val Thr Pro Gly Glu Pro Ala | | |
| 145 150 155 160 | | |
| tcc atc tcc tgc aga tca agt cag agc ctt gtg cac agt aat gga aag | 528 | |
| Ser Ile Ser Cys Arg Ser Ser Gln Ser Leu Val His Ser Asn Gly Lys | | |
| 165 170 175 | | |
| acc tat tta cat tgg tat ctg cag aag cca ggc cag tct cca aga ctc | 576 | |
| Thr Tyr Leu His Trp Tyr Leu Gln Lys Pro Gly Gln Ser Pro Arg Leu | | |
| 180 185 190 | | |
| ctg atc tac aaa gtt tcc aac cga ttt tct ggt gtc cca gac aga ttc | 624 | |
| Leu Ile Tyr Lys Val Ser Asn Arg Phe Ser Gly Val Pro Asp Arg Phe | | |
| 195 200 205 | | |
| agc ggc agt ggg tca ggc act gat ttc aca ctg aaa atc agc agg gtg | 672 | |
| Ser Gly Ser Gly Ser Gly Thr Asp Phe Thr Leu Lys Ile Ser Arg Val | | |
| 210 215 220 | | |
| gag gct gat gat gtt gga att tat tac tgc tct caa agt aca cat gtt | 720 | |
| Glu Ala Asp Asp Val Gly Ile Tyr Tyr Cys Ser Gln Ser Thr His Val | | |
| 225 230 235 240 | | |
| ccg tac acg ttt ggc cag ggg acc aag ctg gag atc aaa ggt ggt ggt | 768 | |
| Pro Tyr Thr Phe Gly Gln Gly Thr Lys Leu Glu Ile Lys Gly Gly Gly | | |
| 245 250 255 | | |
| ggt tcg ggt ggt ggt gga tcc ggt ggt ggc gga tcg cag gtg cag ctg | 816 | |
| Gly Ser Gly Gly Gly Gly Ser Gly Gly Gly Gly Ser Gln Val Gln Leu | | |
| 260 265 270 | | |
| gtg cag tct ggg gct gag gtg aag aag cct ggg gcc tca gtg cag gtt | 864 | |
| Val Gln Ser Gly Ala Glu Val Lys Lys Pro Gly Ala Ser Val Gln Val | | |
| 275 280 285 | | |
| tcc tgt aag gca tct gga tac acc ttc acc aac cat gtt att cac tgg | 912 | |
| Ser Cys Lys Ala Ser Gly Tyr Thr Phe Thr Asn His Val Ile His Trp | | |
| 290 295 300 | | |
| ctg cga cag gcc cct gga caa ggg ctt gag tgg atg gga tat att tat | 960 | |
| Leu Arg Gln Ala Pro Gly Gln Gly Leu Glu Trp Met Gly Tyr Ile Tyr | | |
| 305 310 315 320 | | |
| cct tac aat gat ggt act aag tat aat gag aag ttc aag gac aga gtc | 1008 | |
| Pro Tyr Asn Asp Gly Thr Lys Tyr Asn Glu Lys Phe Lys Asp Arg Val | | |
| 325 330 335 | | |
| acg atg acc tca gac acg tcc atc agc aca gcc tac atg gag ttg agc | 1056 | |
| Thr Met Thr Ser Asp Thr Ser Ile Ser Thr Ala Tyr Met Glu Leu Ser | | |
| 340 345 350 | | |
| agt ctc aga tct gac gac acg gcc gtc tat tat tgt gct aga ggg ggt | 1104 | |
| Ser Leu Arg Ser Asp Asp Thr Ala Val Tyr Tyr Cys Ala Arg Gly Gly | | |
| 355 360 365 | | |
| tac tat act tac gac gac tgg ggc caa gca acc ctg gtc aca gtc tcg | 1152 | |
| Tyr Tyr Thr Tyr Asp Asp Trp Gly Gln Ala Thr Leu Val Thr Val Ser | | |
| 370 375 380 | | |
| agt ggt ggc gga ggt tcc gat att gtg atg act cag tct cca ctc tcc | 1200 | |
| Ser Gly Gly Gly Gly Ser Asp Ile Val Met Thr Gln Ser Pro Leu Ser | | |
| 385 390 395 400 | | |
| ctg ccc gtc acc cct gga gag ccg gcc tcc atc tcc tgc aga tca agt | 1248 | |
| Leu Pro Val Thr Pro Gly Glu Pro Ala Ser Ile Ser Cys Arg Ser Ser | | |

```
                        405                 410                 415
cag agc ctt gtg cac agt aat gga aag acc tat tta cat tgg tat ctg        1296
Gln Ser Leu Val His Ser Asn Gly Lys Thr Tyr Leu His Trp Tyr Leu
            420                 425                 430 cag aag cca ggc cag tct cca aga ctc ctg atc tac aaa gtt tcc aac        1344
Gln Lys Pro Gly Gln Ser Pro Arg Leu Leu Ile Tyr Lys Val Ser Asn
        435                 440                 445 cga ttt tct ggt gtc cca gac aga ttc agc ggc agt ggg tca ggc act        1392
Arg Phe Ser Gly Val Pro Asp Arg Phe Ser Gly Ser Gly Ser Gly Thr
450                 455                 460 gat ttc aca ctg aaa atc agc agg gtg gag gct gat gat gtt gga att        1440
Asp Phe Thr Leu Lys Ile Ser Arg Val Glu Ala Asp Asp Val Gly Ile
465                 470                 475                 480 tat tac tgc tct caa agt aca cat gtt ccg tac acg ttt ggc cag ggg        1488
Tyr Tyr Cys Ser Gln Ser Thr His Val Pro Tyr Thr Phe Gly Gln Gly
                485                 490                 495 acc aag ctg gag atc aaa taatgagcg                                      1515
Thr Lys Leu Glu Ile Lys
            500

<210> SEQ ID NO 79
<211> LENGTH: 1515
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: CDS
<222> LOCATION: (1)..(1506)

<400> SEQUENCE: 79 atg gga tgg agc tgt atc atc ctc ttc ttg gta gca aca gct aca ggt         48
Met Gly Trp Ser Cys Ile Ile Leu Phe Leu Val Ala Thr Ala Thr Gly
1               5                   10                  15 gtc gac tcc cag gtg cag ctg gtg cag tct ggg gct gag gtg aag aag         96
Val Asp Ser Gln Val Gln Leu Val Gln Ser Gly Ala Glu Val Lys Lys
            20                  25                  30 cct ggg gcc tca gtg cag gtt tcc tgt aag gca tct gga tac acc ttc        144
Pro Gly Ala Ser Val Gln Val Ser Cys Lys Ala Ser Gly Tyr Thr Phe
        35                  40                  45 acc aac cat gtt atg cac tgg ctg cga cag gcc cct gga caa ggg ctt        192
Thr Asn His Val Met His Trp Leu Arg Gln Ala Pro Gly Gln Gly Leu
    50                  55                  60 gag tgg atg gga tat att tat cct tac aat gat ggt act aag tat aat        240
Glu Trp Met Gly Tyr Ile Tyr Pro Tyr Asn Asp Gly Thr Lys Tyr Asn
65                  70                  75                  80 gag aag ttc aag ggc aga gtc acg atg acc tca gac acg tcc atc agc        288
Glu Lys Phe Lys Gly Arg Val Thr Met Thr Ser Asp Thr Ser Ile Ser
                85                  90                  95 aca gcc tac atg gag ttg agc agt ctc aga tct gac gac acg gcc gtc        336
Thr Ala Tyr Met Glu Leu Ser Ser Leu Arg Ser Asp Asp Thr Ala Val
            100                 105                 110 tat tat tgt gct aga ggg ggt tac tat tct tac gac gac tgg ggc caa        384
Tyr Tyr Cys Ala Arg Gly Gly Tyr Tyr Ser Tyr Asp Asp Trp Gly Gln
        115                 120                 125 gca acc ctg gtc aca gtc tcg agt ggt ggc gga ggt tcc gat att gtg        432
Ala Thr Leu Val Thr Val Ser Ser Gly Gly Gly Gly Ser Asp Ile Val
    130                 135                 140 atg act cag tct cca ctc tcc ctg ccc gtc acc cct gga gag ccg gcc        480
Met Thr Gln Ser Pro Leu Ser Leu Pro Val Thr Pro Gly Glu Pro Ala
145                 150                 155                 160
```

| | | |
|---|---|---|
| tcc atc tcc tgc aga tca agt cag agc ctt ctg cac agt aag gga aac<br>Ser Ile Ser Cys Arg Ser Ser Gln Ser Leu Leu His Ser Lys Gly Asn<br>                            165                            170                        175 | | 528 |
| acc tat tta cag tgg tat ctg cag aag cca ggc cag tct cca aga ctc<br>Thr Tyr Leu Gln Trp Tyr Leu Gln Lys Pro Gly Gln Ser Pro Arg Leu<br>         180                             185                            190 | | 576 |
| ctg atc tac aaa gtt tcc aac cga ttt tct ggt gtc cca gac aga ttc<br>Leu Ile Tyr Lys Val Ser Asn Arg Phe Ser Gly Val Pro Asp Arg Phe<br>        195                           200                          205 | | 624 |
| agc ggc agt ggg tca ggc act gat ttc aca ctg aaa atc agc agg gtg<br>Ser Gly Ser Gly Ser Gly Thr Asp Phe Thr Leu Lys Ile Ser Arg Val<br>210                         215                          220 | | 672 |
| gag gct gat gat gtt gga att tat tac tgc tct caa agt aca cat gtt<br>Glu Ala Asp Asp Val Gly Ile Tyr Tyr Cys Ser Gln Ser Thr His Val<br>225                       230                        235                        240 | | 720 |
| ccg tac acg ttt ggc cag ggg acc aag ctg gag atc aaa ggt ggt ggt<br>Pro Tyr Thr Phe Gly Gln Gly Thr Lys Leu Glu Ile Lys Gly Gly Gly<br>                    245                          250                          255 | | 768 |
| ggt tcg ggt ggt ggt gga tcc ggt ggt ggc gga tcg cag gtg cag ctg<br>Gly Ser Gly Gly Gly Gly Ser Gly Gly Gly Gly Ser Gln Val Gln Leu<br>                    260                          265                          270 | | 816 |
| gtg cag tct ggg gct gag gtg aag aag cct ggg gcc tca gtg cag gtt<br>Val Gln Ser Gly Ala Glu Val Lys Lys Pro Gly Ala Ser Val Gln Val<br>        275                           280                          285 | | 864 |
| tcc tgt aag gca tct gga tac acc ttc acc aac cat gtt atg cac tgg<br>Ser Cys Lys Ala Ser Gly Tyr Thr Phe Thr Asn His Val Met His Trp<br>                    290                          295                          300 | | 912 |
| ctg cga cag gcc cct gga caa ggg ctt gag tgg atg gga tat att tat<br>Leu Arg Gln Ala Pro Gly Gln Gly Leu Glu Trp Met Gly Tyr Ile Tyr<br>305                       310                        315                        320 | | 960 |
| cct tac aat gat ggt act aag tat aat gag aag ttc aag ggc aga gtc<br>Pro Tyr Asn Asp Gly Thr Lys Tyr Asn Glu Lys Phe Lys Gly Arg Val<br>                    325                          330                          335 | | 1008 |
| acg atg acc tca gac acg tcc atc agc aca gcc tac atg gag ttg agc<br>Thr Met Thr Ser Asp Thr Ser Ile Ser Thr Ala Tyr Met Glu Leu Ser<br>                          340                          345                        350 | | 1056 |
| agt ctc aga tct gac gac acg gcc gtc tat tat tgt gct aga ggg ggt<br>Ser Leu Arg Ser Asp Asp Thr Ala Val Tyr Tyr Cys Ala Arg Gly Gly<br>        355                           360                          365 | | 1104 |
| tac tat tct tac gac gac tgg ggc caa gca acc ctg gtc aca gtc tcg<br>Tyr Tyr Ser Tyr Asp Asp Trp Gly Gln Ala Thr Leu Val Thr Val Ser<br>        370                           375                          380 | | 1152 |
| agt ggt ggc gga ggt tcc gat att gtg atg act cag tct cca ctc tcc<br>Ser Gly Gly Gly Gly Ser Asp Ile Val Met Thr Gln Ser Pro Leu Ser<br>385                       390                        395                        400 | | 1200 |
| ctg ccc gtc acc cct gga gag ccg gcc tcc atc tcc tgc aga tca agt<br>Leu Pro Val Thr Pro Gly Glu Pro Ala Ser Ile Ser Cys Arg Ser Ser<br>                    405                          410                          415 | | 1248 |
| cag agc ctt ctg cac agt aag gga aac acc tat tta cag tgg tat ctg<br>Gln Ser Leu Leu His Ser Lys Gly Asn Thr Tyr Leu Gln Trp Tyr Leu<br>                    420                          425                          430 | | 1296 |
| cag aag cca ggc cag tct cca aga ctc ctg atc tac aaa gtt tcc aac<br>Gln Lys Pro Gly Gln Ser Pro Arg Leu Leu Ile Tyr Lys Val Ser Asn<br>        435                           440                          445 | | 1344 |
| cga ttt tct ggt gtc cca gac aga ttc agc ggc agt ggg tca ggc act<br>Arg Phe Ser Gly Val Pro Asp Arg Phe Ser Gly Ser Gly Ser Gly Thr<br>450                       455                        460 | | 1392 |
| gat ttc aca ctg aaa atc agc agg gtg gag gct gat gat gtt gga att<br>Asp Phe Thr Leu Lys Ile Ser Arg Val Glu Ala Asp Asp Val Gly Ile | | 1440 |

```
                465                 470                 475                 480
tat tac tgc tct caa agt aca cat gtt ccg tac acg ttt ggc cag ggg      1488
Tyr Tyr Cys Ser Gln Ser Thr His Val Pro Tyr Thr Phe Gly Gln Gly
                485                 490                 495 acc aag ctg gag atc aaa taatgagcg                                    1515
Thr Lys Leu Glu Ile Lys
        500
```

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ctcgaggaat tcccaccatg ggatggagct gtatcatcc                           39

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gggggcctgt cgcagccagt gaataac                                        27

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gggcagtcag tgtatacggc cgtgtcgtca gatctgagac tgctc                    45

<210> SEQ ID NO 83
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gggcaatgcc ttgagtggat gggatatatt tatcc                               35

<210> SEQ ID NO 84
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tcattatttg atctcaagct tggtcccgca gccaaacgtg tacggaacat gtgt           54

<210> SEQ ID NO 85
<211> LENGTH: 68
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 85

```
tactattgtg ctagagggggg ttactatact tacgacgact ggggctgcgc aaccctggtc    60
acagtctc                                                              68
```

<210> SEQ ID NO 86
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 86

```
gggcttctgc agataccaat gtaaataggt ctttc                                35
```

<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87

```
gggcagtgcc caagactcct gatctacaaa gtttcc                               36
```

<210> SEQ ID NO 88
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88

```
tcattatttg atctcaagct tggtcccctg gccaaac                              37
```

<210> SEQ ID NO 89
<211> LENGTH: 708
<212> TYPE: DNA
<213> ORGANISM: Artificial Sequence
<220> FEATURE:
<223> OTHER INFORMATION: Description of Artificial Sequence: Synthetic
polynucleotide sequence

<400> SEQUENCE: 89

```
caggtgcagc tggtgcagtc tggggctgag gtgaagaagc ctggggcctc agtgcaggtt     60
tcctgtaagg catctggata caccttcacc aaccatgtta ttcactggct gcgacaggcc    120
cccgggcaat gccttgagtg gatgggatat atttatcctt acaatgatgg tactaagtat    180
aatgagaagt tcaaggacag agtcacgatg acctcagaca cgtccatcag cacagcctac    240
atggagttga gcagtctcag atctgacgac acggccgtct attattgtgc tagagggggt    300
tactatactt acgacgactg gggccaagca acctggtca cagtctcgag tggtggcgga    360
ggttccgata ttgtgatgac tcagtctcca ctctccctgc ccgtcacccc tggagagccg    420
gcctccatct cctgcagatc aagtcagagc cttgtgcaca gtaatggaaa gacctattta    480
cattggtatc tgcagaagcc aggccagtct ccaagactcc tgatctacaa agtttccaac    540
```

```
cgattttctg gtgtcccaga cagattcagc ggcagtgggt caggcactga tttcacactg      600
aaaatcagca gggtggaggc tgatgatgtt ggaatttatt actgctctca aagtacacat      660
gttccgtaca cgtttggctg cgggaccaag cttgagatca ataatga                    708
```

<210> SEQ ID NO 90
<211> LENGTH: 234
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 90

```
Gln Val Gln Leu Val Gln Ser Gly Ala Glu Val Lys Lys Pro Gly Ala
 1               5                  10                  15

Ser Val Gln Val Ser Cys Lys Ala Ser Gly Tyr Thr Phe Thr Asn His
            20                  25                  30

Val Ile His Trp Leu Arg Gln Ala Pro Gly Gln Cys Leu Glu Trp Met
        35                  40                  45

Gly Tyr Ile Tyr Pro Tyr Asn Asp Gly Thr Lys Tyr Asn Glu Lys Phe
    50                  55                  60

Lys Asp Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Tyr Tyr Thr Tyr Asp Asp Trp Gly Gln Ala Thr Leu
            100                 105                 110

Val Thr Val Ser Ser Gly Gly Gly Ser Asp Ile Val Met Thr Gln
        115                 120                 125

Ser Pro Leu Ser Leu Pro Val Thr Pro Gly Glu Pro Ala Ser Ile Ser
    130                 135                 140

Cys Arg Ser Ser Gln Ser Leu Val His Ser Asn Gly Lys Thr Tyr Leu
145                 150                 155                 160

His Trp Tyr Leu Gln Lys Pro Gly Gln Ser Pro Arg Leu Leu Ile Tyr
                165                 170                 175

Lys Val Ser Asn Arg Phe Ser Gly Val Pro Asp Arg Phe Ser Gly Ser
            180                 185                 190

Gly Ser Gly Thr Asp Phe Thr Leu Lys Ile Ser Arg Val Glu Ala Asp
        195                 200                 205

Asp Val Gly Ile Tyr Tyr Cys Ser Gln Ser Thr His Val Pro Tyr Thr
    210                 215                 220

Phe Gly Cys Gly Thr Lys Leu Glu Ile Lys
225                 230
```

<210> SEQ ID NO 91
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 91

```
caggtgcagc tggtgcagtc tggggctgag gtgaagaagc ctggggcctc agtgcaggtt       60
tcctgtaagg catctggata caccttcacc aaccatgtta ttcactggct gcgacaggcc      120
cctgggcaag gcttgagtg gatgggatat atttatcctt acaatgatgg tactaagtat      180
```

```
aatgagaagt tcaaggacag agtcacgatg acctcagaca cgtccatcag cacagcctac    240
atggagttga gcagtctcag atctgacgac acggccgtat actattgtgc tagaggggt     300 tactatactt acgacgactg gggctgcgca accctggtca cagtctcgag tggtggcgga    360
ggttccgata ttgtgatgac tcagtctcca ctctccctgc ccgtcacccc tggagagccg    420
gcctccatct cctgcagatc aagtcagagc cttgtgcaca gtaatggaaa gacctattta    480
cattggtatc tgcagaagcc cgggcagtgc ccaagactcc tgatctacaa agtttccaac    540
cgattttctg gtgtcccaga cagattcagc ggcagtgggt caggcactga tttcacactg    600
aaaatcagca gggtggaggc tgatgatgtt ggaatttatt actgctctca aagtacacat    660
gttccgtaca cgtttggcca ggggaccaag cttgagatca ataatga              708
```

<210> SEQ ID NO 92
<211> LENGTH: 234
<212> TYPE: PRT
<213> ORGANISM: Artificial Sequence
<220> FEATURE:
<223> OTHER INFORMATION: Description of Artificial Sequence: Synthetic
    protein

<400> SEQUENCE: 92

```
Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn His
            20                  25                  30

Val Ile His Trp Leu Arg Gln Ala Pro Gly Gln Gly Leu Glu Trp Met
        35                  40                  45

Gly Tyr Ile Tyr Pro Tyr Asn Asp Gly Thr Lys Tyr Asn Glu Lys Phe
    50                  55                  60

Lys Asp Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Tyr Tyr Thr Tyr Asp Asp Trp Gly Cys Ala Thr Leu
            100                 105                 110

Val Thr Val Ser Ser Gly Gly Gly Gly Ser Asp Ile Val Met Thr Gln
        115                 120                 125

Ser Pro Leu Ser Leu Pro Val Thr Pro Gly Glu Pro Ala Ser Ile Ser
    130                 135                 140

Cys Arg Ser Ser Gln Ser Leu Val His Ser Asn Gly Lys Thr Tyr Leu
145                 150                 155                 160

His Trp Tyr Leu Gln Lys Pro Gly Gln Cys Pro Arg Leu Leu Ile Tyr
                165                 170                 175

Lys Val Ser Asn Arg Phe Ser Gly Val Pro Asp Arg Phe Ser Gly Ser
            180                 185                 190

Gly Ser Gly Thr Asp Phe Thr Leu Lys Ile Ser Arg Val Glu Ala Asp
        195                 200                 205

Asp Val Gly Ile Tyr Tyr Cys Ser Gln Ser Thr His Val Pro Tyr Thr
    210                 215                 220

Phe Gly Gln Gly Thr Lys Leu Glu Ile Lys
225                 230
```

<210> SEQ ID NO 93
<211> LENGTH: 136
<212> TYPE: PRT
<213> ORGANISM: Artificial Sequence
<220> FEATURE:
<223> OTHER INFORMATION: Description of Artificial Sequence: Synthetic
     plasmid

<400> SEQUENCE: 93

Met Glu Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ala Asn His Val Ile His Trp Val Arg Gln Ala Pro Gly Gln Gly Leu
    50                  55                  60

Glu Trp Met Gly Tyr Ile Tyr Pro Tyr Asn Asp Gly Thr Lys Tyr Asn
65                  70                  75                  80

Glu Lys Phe Lys Asp Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Gly Tyr Tyr Thr Tyr Asp Asp Trp Gly Gln
        115                 120                 125

Gly Thr Leu Val Thr Val Ser Ser
130                 135

<210> SEQ ID NO 94
<211> LENGTH: 136
<212> TYPE: PRT
<213> ORGANISM: Artificial Sequence
<220> FEATURE:
<223> OTHER INFORMATION: Description of Artificial Sequence: Synthetic
     plasmid

<400> SEQUENCE: 94

Met Glu Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ala Asn His Val Ile His Trp Val Arg Gln Ala Pro Gly Gln Gly Leu
    50                  55                  60

Glu Trp Met Gly Tyr Ile Tyr Pro Tyr Asn Asp Gly Thr Lys Tyr Asn
65                  70                  75                  80

Glu Lys Phe Lys Asp Arg Val Thr Met Thr Ser Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Gly Tyr Tyr Thr Tyr Asp Asp Trp Gly Gln
        115                 120                 125

Gly Thr Leu Val Thr Val Ser Ser
130                 135

<210> SEQ ID NO 95
<211> LENGTH: 136
<212> TYPE: PRT
<213> ORGANISM: Artificial Sequence
<220> FEATURE:
<223> OTHER INFORMATION: Description of Artificial Sequence: Synthetic
     plasmid

<400> SEQUENCE: 95

Met Glu Trp Ser Trp Ile Phe Leu Phe Leu Leu Ser Gly Thr Ala Gly
 1               5                  10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn His Val Ile His Trp Val Arg Gln Ala Pro Gly Gln Gly Leu
    50                  55                  60

Glu Trp Met Gly Tyr Ile Tyr Pro Tyr Asn Asp Gly Thr Lys Tyr Asn
65                  70                  75                  80

Glu Lys Phe Lys Asp Arg Val Thr Met Thr Ser Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Gly Tyr Tyr Thr Tyr Asp Asp Trp Gly Gln
        115                 120                 125

Gly Thr Leu Val Thr Val Ser Ser
    130                 135

<210> SEQ ID NO 96
<211> LENGTH: 136
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 96

Met Glu Trp Ser Trp Ile Phe Leu Phe Leu Leu Ser Gly Thr Ala Gly
 1               5                  10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ala Asn His Val Ile His Trp Val Arg Gln Ala Pro Gly Gln Gly Leu
    50                  55                  60

Glu Trp Met Gly Tyr Ile Tyr Pro Tyr Asn Asp Gly Thr Lys Tyr Asn
65                  70                  75                  80

Glu Lys Phe Lys Asp Lys Val Thr Met Thr Ser Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Gly Tyr Tyr Thr Tyr Asp Asp Trp Gly Gln
        115                 120                 125

Gly Thr Leu Val Thr Val Ser Ser
    130                 135

<210> SEQ ID NO 97
<211> LENGTH: 136
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 97

Met Glu Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ala Asn His Val Ile His Trp Val Arg Gln Ala Pro Gly Gln Gly Leu
    50                  55                  60

Glu Trp Met Gly Tyr Ile Tyr Pro Tyr Asn Gly Thr Lys Tyr Asn
65              70                  75                  80

Glu Lys Phe Lys Asp Arg Val Thr Leu Thr Ser Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Gly Tyr Tyr Thr Tyr Asp Asp Trp Gly Gln
        115                 120                 125

Gly Thr Leu Val Thr Val Ser Ser
    130                 135

<210> SEQ ID NO 98
<211> LENGTH: 136
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 98

Met Glu Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn His Val Ile His Trp Val Arg Gln Ala Pro Gly Gln Gly Leu
    50                  55                  60

Glu Trp Met Gly Tyr Ile Tyr Pro Tyr Asn Asp Gly Thr Lys Tyr Asn
65              70                  75                  80

Glu Lys Phe Lys Asp Arg Val Thr Met Thr Ser Asp Thr Ser Thr Ser
                85                  90                  95

Thr Val Tyr Met Glu Leu Ser Ser Leu Arg Ser Asp Asp Thr Ala Val
            100                 105                 110

Tyr Tyr Cys Ala Arg Gly Gly Tyr Tyr Thr Tyr Asp Asp Trp Gly Gln
        115                 120                 125

Gly Thr Leu Val Thr Val Ser Ser
    130                 135

<210> SEQ ID NO 99
<211> LENGTH: 136
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 99

Met Glu Trp Ser Trp Ile Phe Leu Phe Leu Leu Ser Gly Thr Ala Gly
1               5                   10                  15

```
Val His Ser Gln Val Gln Leu Val Gln Ser Gly Ala Glu Val Lys Lys
            20                  25                  30

Pro Gly Ala Ser Val Gln Val Ser Cys Lys Ala Ser Gly Tyr Thr Phe
        35                  40                  45

Thr Asn His Val Ile His Trp Leu Arg Gln Ala Pro Gly Gln Gly Leu
 50                  55                  60

Glu Trp Met Gly Tyr Ile Tyr Pro Tyr Asn Asp Gly Thr Lys Tyr Asn
 65                  70                  75                  80

Glu Lys Phe Lys Asp Arg Val Thr Met Thr Ser Asp Thr Ser Ile Ser
                85                  90                  95

Thr Ala Tyr Met Glu Leu Ser Ser Leu Arg Ser Asp Asp Thr Ala Val
            100                 105                 110

Tyr Tyr Cys Ala Arg Gly Gly Tyr Tyr Thr Tyr Asp Asp Trp Gly Gln
        115                 120                 125

Ala Thr Leu Val Thr Val Ser Ser
        130                 135

<210> SEQ ID NO 100
<211> LENGTH: 132
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 100

Met Arg Leu Pro Ala Gln Leu Leu Gly Leu Leu Met Leu Trp Val Pro
 1               5                  10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val His Ser Asn Gly Lys Thr Tyr Leu His Trp Phe Gln Gln Arg
 50                  55                  60

Pro Gly Gln Ser Pro Arg Arg Leu Ile Tyr Lys Val Ser Asn Arg Phe
 65                  70                  75                  80

Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Val Gly Val Tyr Tyr
            100                 105                 110

Cys Ser Gln Ser Thr His Val Pro Tyr Thr Phe Gly Gln Gly Thr Lys
        115                 120                 125

Leu Glu Ile Lys
        130

<210> SEQ ID NO 101
<211> LENGTH: 132
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 101

Met Arg Leu Pro Ala Gln Leu Leu Gly Leu Leu Met Leu Trp Val Pro
 1               5                  10                  15

Gly Ser Ser Gly Asp Val Val Met Thr Gln Ser Pro Leu Ser Leu Pro
            20                  25                  30
```

```
Val Thr Leu Gly Gln Pro Ala Ser Ile Ser Cys Arg Ser Gln Ser
        35                  40                  45

Leu Val His Ser Asn Gly Lys Thr Tyr Leu His Trp Phe Gln Gln Arg
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
                100                 105                 110

Cys Ser Gln Ser Thr His Val Pro Tyr Thr Phe Gly Gln Gly Thr Lys
                115                 120                 125

Leu Glu Ile Lys
        130

<210> SEQ ID NO 102
<211> LENGTH: 132
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 102

Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
                20                  25                  30

Val Thr Leu Gly Gln Pro Ala Ser Ile Ser Cys Arg Ser Ser Gln Ser
        35                  40                  45

Leu Val His Ser Asn Gly Lys Thr Tyr Leu His Trp Phe Gln Gln Arg
    50                  55                  60

Pro Gly Gln Ser Pro Arg Arg Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Phe
                100                 105                 110

Cys Ser Gln Ser Thr His Val Pro Tyr Thr Phe Gly Gln Gly Thr Lys
                115                 120                 125

Leu Glu Ile Lys
        130

<210> SEQ ID NO 103
<211> LENGTH: 132
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 103

Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
                20                  25                  30

Val Thr Leu Gly Gln Pro Ala Ser Ile Ser Cys Arg Ser Ser Gln Ser
        35                  40                  45
```

Leu Val His Ser Asn Gly Lys Thr Tyr Leu His Trp Tyr Gln Gln Arg
    50                  55                  60

Pro Gly Gln Ser Pro Arg Arg Leu Ile Tyr Lys Val Ser Asn Arg Phe
 65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
                100                 105                 110

Cys Ser Gln Ser Thr His Val Pro Tyr Thr Phe Gly Gln Gly Thr Lys
            115                 120                 125

Leu Glu Ile Lys
    130

<210> SEQ ID NO 104
<211> LENGTH: 132
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 104

Met Arg Leu Pro Ala Gln Leu Leu Gly Leu Leu Met Leu Trp Val Pro
 1               5                  10                  15

Gly Ser Ser Gly Asp Val Val Met Thr Gln Ser Pro Leu Ser Leu Pro
                20                  25                  30

Val Thr Leu Gly Gln Pro Ala Ser Ile Ser Cys Arg Ser Ser Gln Ser
            35                  40                  45

Leu Val His Ser Asn Gly Lys Thr Tyr Leu His Trp Phe Leu Gln Arg
    50                  55                  60

Pro Gly Gln Ser Pro Arg Arg Leu Ile Tyr Lys Val Ser Asn Arg Phe
 65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
                100                 105                 110

Cys Ser Gln Ser Thr His Val Pro Tyr Thr Phe Gly Gln Gly Thr Lys
            115                 120                 125

Leu Glu Ile Lys
    130

<210> SEQ ID NO 105
<211> LENGTH: 132
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 105

Met Arg Leu Pro Ala Gln Leu Leu Gly Leu Leu Met Leu Trp Val Pro
 1               5                  10                  15

Gly Ser Ser Gly Asp Val Val Met Thr Gln Ser Pro Leu Ser Leu Pro
                20                  25                  30

Val Thr Leu Gly Gln Pro Ala Ser Ile Ser Cys Arg Ser Ser Gln Ser
            35                  40                  45

Leu Val His Ser Asn Gly Lys Thr Tyr Leu His Trp Tyr Leu Gln Lys
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Tyr Thr Phe Gly Gln Gly Thr Lys
        115                 120                 125

Leu Glu Ile Lys
    130

<210> SEQ ID NO 106
<211> LENGTH: 132
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 106

Met Arg Leu Pro Ala Gln Leu Leu Gly Leu Leu Met Leu Trp Val Pro
1               5                   10                  15

Gly Ser Ser Gly Asp Ile Val Met Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Leu Val His Ser Asn Gly Lys Thr Tyr Leu His Trp Tyr Leu Gln Lys
        50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Asp Asp Val Gly Ile Tyr Tyr
            100                 105                 110

Cys Ser Gln Ser Thr His Val Pro Tyr Thr Phe Gly Gln Gly Thr Lys
        115                 120                 125

Leu Glu Ile Lys
    130

<210> SEQ ID NO 107
<211> LENGTH: 136
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 107

Met Glu Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
                20                  25                  30

Pro Gly Ala Ser Val Gln Val Ser Cys Lys Ala Ser Gly Tyr Thr Phe
            35                  40                  45

Thr Asn His Val Met His Trp Leu Arg Gln Ala Pro Gly Gln Gly Leu
        50                  55                  60

Glu Trp Met Gly Tyr Ile Tyr Pro Tyr Asn Asp Gly Thr Lys Tyr Asn
65                  70                  75                  80

Glu Lys Phe Lys Gly Arg Val Thr Met Thr Ser Asp Thr Ser Ile Ser
                85                  90                  95

Thr Ala Tyr Met Glu Leu Ser Ser Leu Arg Ser Asp Asp Thr Ala Val
            100                 105                 110

Tyr Tyr Cys Ala Arg Gly Gly Tyr Tyr Ser Tyr Asp Asp Trp Gly Gln
        115                 120                 125

Ala Thr Leu Val Thr Val Ser Ser
    130                 135

<210> SEQ ID NO 108
<211> LENGTH: 132
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 108

Met Arg Leu Pro Ala Gln Leu Leu Gly Leu Leu Met Leu Trp Val Pro
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Leu His Ser Lys Gly Asn Thr Tyr Leu Gln Trp Tyr Leu Gln Lys
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Asp Asp Val Gly Ile Tyr Tyr
            100                 105                 110

Cys Ser Gln Ser Thr His Val Pro Tyr Thr Phe Gly Gln Gly Thr Lys
        115                 120                 125

Leu Glu Ile Lys
    130

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      oligonucleotide

<400> SEQUENCE: 109

Gly Gly Gly Gly Ser
1               5

<210> SEQ ID NO 110
<211> LENGTH: 253
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 110

Met Gly Trp Ser Cys Ile Ile Leu Phe Leu Val Ala Thr Ala Thr Gly
1               5                   10                  15

Val Asp Ser Gln Val Gln Leu Val Gln Ser Gly Ala Glu Val Lys Lys

```
                    20                  25                  30
Pro Gly Ala Ser Val Gln Val Ser Cys Lys Ala Ser Gly Tyr Thr Phe
                35                  40                  45
Thr Asn His Val Ile His Trp Leu Arg Gln Ala Pro Gly Gln Gly Leu
            50                  55                  60
Glu Trp Met Gly Tyr Ile Tyr Pro Tyr Asn Asp Gly Thr Lys Tyr Asn
65                  70                  75                  80
Glu Lys Phe Lys Asp Arg Val Thr Met Thr Ser Asp Thr Ser Ile Ser
                85                  90                  95
Thr Ala Tyr Met Glu Leu Ser Ser Leu Arg Ser Asp Asp Thr Ala Val
            100                 105                 110
Tyr Tyr Cys Ala Arg Gly Gly Tyr Tyr Thr Tyr Asp Asp Trp Gly Gln
            115                 120                 125
Ala Thr Leu Val Thr Val Ser Ser Gly Gly Gly Ser Asp Ile Val
            130                 135                 140
Met Thr Gln Ser Pro Leu Ser Leu Pro Val Thr Pro Gly Glu Pro Ala
145                 150                 155                 160
Ser Ile Ser Cys Arg Ser Ser Gln Ser Leu Val His Ser Asn Gly Lys
                165                 170                 175
Thr Tyr Leu His Trp Tyr Leu Gln Lys Pro Gly Gln Ser Pro Arg Leu
            180                 185                 190
Leu Ile Tyr Lys Val Ser Asn Arg Phe Ser Gly Val Pro Asp Arg Phe
            195                 200                 205
Ser Gly Ser Gly Ser Gly Thr Asp Phe Thr Leu Lys Ile Ser Arg Val
            210                 215                 220
Glu Ala Asp Asp Val Gly Ile Tyr Tyr Cys Ser Gln Ser Thr His Val
225                 230                 235                 240
Pro Tyr Thr Phe Gly Gln Gly Thr Lys Leu Glu Ile Lys
                245                 250

<210> SEQ ID NO 111
<211> LENGTH: 253
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 111

Met Gly Trp Ser Cys Ile Ile Leu Phe Leu Val Ala Thr Ala Thr Gly
1               5                   10                  15
Val Asp Ser Gln Val Gln Leu Val Gln Ser Gly Ala Glu Val Lys Lys
                20                  25                  30
Pro Gly Ala Ser Val Gln Val Ser Cys Lys Ala Ser Gly Tyr Thr Phe
            35                  40                  45
Thr Asn His Val Met His Trp Leu Arg Gln Ala Pro Gly Gln Gly Leu
            50                  55                  60
Glu Trp Met Gly Tyr Ile Tyr Pro Tyr Asn Asp Gly Thr Lys Tyr Asn
65                  70                  75                  80
Glu Lys Phe Lys Gly Arg Val Thr Met Thr Ser Asp Thr Ser Ile Ser
                85                  90                  95
Thr Ala Tyr Met Glu Leu Ser Ser Leu Arg Ser Asp Asp Thr Ala Val
            100                 105                 110
Tyr Tyr Cys Ala Arg Gly Gly Tyr Ser Tyr Asp Asp Trp Gly Gln
            115                 120                 125
```

```
Ala Thr Leu Val Thr Val Ser Ser Gly Gly Gly Ser Asp Ile Val
    130                 135                 140

Met Thr Gln Ser Pro Leu Ser Leu Pro Val Thr Pro Gly Glu Pro Ala
145                 150                 155                 160

Ser Ile Ser Cys Arg Ser Ser Gln Ser Leu Leu His Ser Lys Gly Asn
                165                 170                 175

Thr Tyr Leu Gln Trp Tyr Leu Gln Lys Pro Gly Gln Ser Pro Arg Leu
            180                 185                 190

Leu Ile Tyr Lys Val Ser Asn Arg Phe Ser Gly Val Pro Asp Arg Phe
        195                 200                 205

Ser Gly Ser Gly Ser Gly Thr Asp Phe Thr Leu Lys Ile Ser Arg Val
210                 215                 220

Glu Ala Asp Asp Val Gly Ile Tyr Tyr Cys Ser Gln Ser Thr His Val
225                 230                 235                 240

Pro Tyr Thr Phe Gly Gln Gly Thr Lys Leu Glu Ile Lys
                245                 250

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      oligonucleotide

<400> SEQUENCE: 112

Gly Gly Gly Gly Ser Gly Gly Gly Gly Ser Gly Gly Gly Gly Ser
1               5                   10                  15

<210> SEQ ID NO 113
<211> LENGTH: 502
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 113

Met Gly Trp Ser Cys Ile Ile Leu Phe Leu Val Ala Thr Ala Thr Gly
1               5                   10                  15

Val Asp Ser Gln Val Gln Leu Val Gln Ser Gly Ala Glu Val Lys Lys
            20                  25                  30

Pro Gly Ala Ser Val Gln Val Ser Cys Lys Ala Ser Gly Tyr Thr Phe
        35                  40                  45

Thr Asn His Val Ile His Trp Leu Arg Gln Ala Pro Gly Gln Gly Leu
    50                  55                  60

Glu Trp Met Gly Tyr Ile Tyr Pro Tyr Asn Asp Gly Thr Lys Tyr Asn
65                  70                  75                  80

Glu Lys Phe Lys Asp Arg Val Thr Met Thr Ser Asp Thr Ser Ile Ser
                85                  90                  95

Thr Ala Tyr Met Glu Leu Ser Ser Leu Arg Ser Asp Asp Thr Ala Val
            100                 105                 110

Tyr Tyr Cys Ala Arg Gly Gly Tyr Tyr Thr Tyr Asp Asp Trp Gly Gln
        115                 120                 125

Ala Thr Leu Val Thr Val Ser Ser Gly Gly Gly Ser Asp Ile Val
    130                 135                 140

Met Thr Gln Ser Pro Leu Ser Leu Pro Val Thr Pro Gly Glu Pro Ala
145                 150                 155                 160
```

Ser Ile Ser Cys Arg Ser Ser Gln Ser Leu Val His Ser Asn Gly Lys
                165                 170                 175

Thr Tyr Leu His Trp Tyr Leu Gln Lys Pro Gly Gln Ser Pro Arg Leu
            180                 185                 190

Leu Ile Tyr Lys Val Ser Asn Arg Phe Ser Gly Val Pro Asp Arg Phe
        195                 200                 205

Ser Gly Ser Gly Ser Gly Thr Asp Phe Thr Leu Lys Ile Ser Arg Val
    210                 215                 220

Glu Ala Asp Asp Val Gly Ile Tyr Tyr Cys Ser Gln Ser Thr His Val
225                 230                 235                 240

Pro Tyr Thr Phe Gly Gln Gly Thr Lys Leu Glu Ile Lys Gly Gly Gly
                245                 250                 255

Gly Ser Gly Gly Gly Gly Ser Gly Gly Gly Ser Gln Val Gln Leu
                260                 265                 270

Val Gln Ser Gly Ala Glu Val Lys Lys Pro Gly Ala Ser Val Gln Val
        275                 280                 285

Ser Cys Lys Ala Ser Gly Tyr Thr Phe Thr Asn His Val Ile His Trp
    290                 295                 300

Leu Arg Gln Ala Pro Gly Gln Gly Leu Glu Trp Met Gly Tyr Ile Tyr
305                 310                 315                 320

Pro Tyr Asn Asp Gly Thr Lys Tyr Asn Glu Lys Phe Lys Asp Arg Val
                325                 330                 335

Thr Met Thr Ser Asp Thr Ser Ile Ser Thr Ala Tyr Met Glu Leu Ser
            340                 345                 350

Ser Leu Arg Ser Asp Asp Thr Ala Val Tyr Tyr Cys Ala Arg Gly Gly
        355                 360                 365

Tyr Tyr Thr Tyr Asp Asp Trp Gly Gln Ala Thr Leu Val Thr Val Ser
    370                 375                 380

Ser Gly Gly Gly Gly Ser Asp Ile Val Met Thr Gln Ser Pro Leu Ser
385                 390                 395                 400

Leu Pro Val Thr Pro Gly Glu Pro Ala Ser Ile Ser Cys Arg Ser Ser
                405                 410                 415

Gln Ser Leu Val His Ser Asn Gly Lys Thr Tyr Leu His Trp Tyr Leu
            420                 425                 430

Gln Lys Pro Gly Gln Ser Pro Arg Leu Leu Ile Tyr Lys Val Ser Asn
        435                 440                 445

Arg Phe Ser Gly Val Pro Asp Arg Phe Ser Gly Ser Gly Ser Gly Thr
    450                 455                 460

Asp Phe Thr Leu Lys Ile Ser Arg Val Glu Ala Asp Asp Val Gly Ile
465                 470                 475                 480

Tyr Tyr Cys Ser Gln Ser Thr His Val Pro Tyr Thr Phe Gly Gln Gly
                485                 490                 495

Thr Lys Leu Glu Ile Lys
            500

<210> SEQ ID NO 114
<211> LENGTH: 502
<212> TYPE: PRT
<213> ORGANISM: Artificial Sequence
<220> FEATURE:
<223> OTHER INFORMATION: Description of Artificial Sequence: Synthetic
      plasmid

<400> SEQUENCE: 114

Met Gly Trp Ser Cys Ile Ile Leu Phe Leu Val Ala Thr Ala Thr Gly
1               5                   10                  15

```
Val Asp Ser Gln Val Gln Leu Val Gln Ser Gly Ala Glu Val Lys Lys
             20                  25                  30

Pro Gly Ala Ser Val Gln Val Ser Cys Lys Ala Ser Gly Tyr Thr Phe
         35                  40                  45

Thr Asn His Val Met His Trp Leu Arg Gln Ala Pro Gly Gln Gly Leu
 50                  55                  60

Glu Trp Met Gly Tyr Ile Tyr Pro Tyr Asn Asp Gly Thr Lys Tyr Asn
65                  70                  75                  80

Glu Lys Phe Lys Gly Arg Val Thr Met Thr Ser Asp Thr Ser Ile Ser
                 85                  90                  95

Thr Ala Tyr Met Glu Leu Ser Ser Leu Arg Ser Asp Asp Thr Ala Val
            100                 105                 110

Tyr Tyr Cys Ala Arg Gly Gly Tyr Tyr Ser Tyr Asp Asp Trp Gly Gln
        115                 120                 125

Ala Thr Leu Val Thr Val Ser Ser Gly Gly Gly Gly Ser Asp Ile Val
    130                 135                 140

Met Thr Gln Ser Pro Leu Ser Leu Pro Val Thr Pro Gly Glu Pro Ala
145                 150                 155                 160

Ser Ile Ser Cys Arg Ser Ser Gln Ser Leu Leu His Ser Lys Gly Asn
                165                 170                 175

Thr Tyr Leu Gln Trp Tyr Leu Gln Lys Pro Gly Gln Ser Pro Arg Leu
            180                 185                 190

Leu Ile Tyr Lys Val Ser Asn Arg Phe Ser Gly Val Pro Asp Arg Phe
        195                 200                 205

Ser Gly Ser Gly Ser Gly Thr Asp Phe Thr Leu Lys Ile Ser Arg Val
    210                 215                 220

Glu Ala Asp Asp Val Gly Ile Tyr Tyr Cys Ser Gln Ser Thr His Val
225                 230                 235                 240

Pro Tyr Thr Phe Gly Gln Gly Thr Lys Leu Glu Ile Lys Gly Gly Gly
                245                 250                 255

Gly Ser Gly Gly Gly Gly Ser Gly Gly Gly Gly Ser Gln Val Gln Leu
            260                 265                 270

Val Gln Ser Gly Ala Glu Val Lys Lys Pro Gly Ala Ser Val Gln Val
        275                 280                 285

Ser Cys Lys Ala Ser Gly Tyr Thr Phe Thr Asn His Val Met His Trp
    290                 295                 300

Leu Arg Gln Ala Pro Gly Gln Gly Leu Glu Trp Met Gly Tyr Ile Tyr
305                 310                 315                 320

Pro Tyr Asn Asp Gly Thr Lys Tyr Asn Glu Lys Phe Lys Gly Arg Val
                325                 330                 335

Thr Met Thr Ser Asp Thr Ser Ile Ser Thr Ala Tyr Met Glu Leu Ser
            340                 345                 350

Ser Leu Arg Ser Asp Asp Thr Ala Val Tyr Tyr Cys Ala Arg Gly Gly
        355                 360                 365

Tyr Tyr Ser Tyr Asp Asp Trp Gly Gln Ala Thr Leu Val Thr Val Ser
    370                 375                 380

Ser Gly Gly Gly Gly Ser Asp Ile Val Met Thr Gln Ser Pro Leu Ser
385                 390                 395                 400

Leu Pro Val Thr Pro Gly Glu Pro Ala Ser Ile Ser Cys Arg Ser Ser
                405                 410                 415

Gln Ser Leu Leu His Ser Lys Gly Asn Thr Tyr Leu Gln Trp Tyr Leu
            420                 425                 430
```

```
Gln Lys Pro Gly Gln Ser Pro Arg Leu Leu Ile Tyr Lys Val Ser Asn
            435                 440                 445

Arg Phe Ser Gly Val Pro Asp Arg Phe Ser Gly Ser Gly Ser Gly Thr
        450                 455                 460

Asp Phe Thr Leu Lys Ile Ser Arg Val Glu Ala Asp Val Gly Ile
465                 470                 475                 480

Tyr Tyr Cys Ser Gln Ser Thr His Val Pro Tyr Thr Phe Gly Gln Gly
                485                 490                 495

Thr Lys Leu Glu Ile Lys
            500

<210> SEQ ID NO 115
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 115

Gly Gly Gly Ser
1

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 116

Ser Gly Gly Gly
1

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 117

Ser Gly Gly Gly Gly
1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 118

Gly Gly Gly Gly Gly Ser
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide linker
```

```
<400> SEQUENCE: 119

Ser Gly Gly Gly Gly Gly
  1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 120

Gly Gly Gly Gly Gly Gly Ser
  1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 121

Ser Gly Gly Gly Gly Gly Gly
  1               5
```

HUMANIZED ANTI-CD47 ANTIBODY

CROSS-REFERENCE TO RELATED APPLICATIONS

This application is a Divisional of U.S. application Ser. No. 10/578,840, which is the U.S. National Stage application of PCT/JP2004/016744, filed Nov. 11, 2004, which claims priority from Japanese patent application JP 2003-381406, filed Nov. 11, 2003. The entire contents of each of the aforementioned applications are incorporated herein by reference.

The instant application contains a Sequence Listing which has been submitted in ASCII format via EFS-WEB and is hereby incorporated by reference in its entirety. Said ASCII copy, created on Dec. 16, 2011, is named sequence.txt and is 113 KB.

TECHNICAL FIELD

The present invention relates to humanized antibodies binding to CD47. Said humanized anti-CD47 antibodies are useful as therapeutic agents for hematological disorders such as leukemias.

BACKGROUND ART

CD47 is a membrane-associated protein also called Integrin Associated Protein (IAP). Integrins are one of adherent cells playing a role in the adhesion of a cell to the extracellular matrix and of a cell to another cell, and form heterodimers consisting of two different subunits, i.e., an α-chain and a β-chain. Recently, attention has been focused on an integrin-associated molecule CD47 (IAP) forming a complex with the αvβ3 integrin, and medical uses of antibodies against it have also been studied.

WO97/32601 attempts to raise a monoclonal antibody against a splenic interstitial cell strain with the purpose of developing a specific antibody capable of identifying splenic interstitial cells and describes the acquisition of a novel monoclonal antibody recognizing mouse CD47 as an antigen. On the other hand, WO97/32601 discloses that said monoclonal antibody has the property of inducing apoptosis in myeloid cells.

WO99/12973 describes monoclonal antibodies raised against CD47 of humans (hereinafter referred to as human CD47; the amino acid sequence and nucleotide sequence described in J. Cell Biol., 123, 485-496, 1993; Journal of Cell Science, 108, 3419-3425, 1995) and having the property of inducing apoptosis in nucleated blood cells having the human CD47 (myeloid cells and lymphocytes), i.e., monoclonal MABL-1 and MABL-2 antibodies, and hybridomas producing them, i.e., MABL-1 (FERM BP-6100) and MABL-2 (FERM BP-6101).

WO02/33072 and WO02/33073 disclose a single chain Fv having a single chain Fv region having the property of inducing apoptosis in nucleated blood cells having the human CD47 from a monoclonal antibody raised against the human CD47.

However, when monoclonal antibodies raised against human CD47 are to be used as therapeutic agents, it is necessary to lower the antigenicity while retaining the CD47-binding activity and apoptosis-inducing activity.

References:
  Patent document 1: WO97/32601.
  Patent document 2: WO99/12973.
  Patent document 3: WO02/33072, WO02/33073.
  Non-patent document 1: J. Cell Biol., 123, 485-496, 1993.

Non-patent document 2: Journal of Cell Science, 108, 3419-3425, 1995.

DISCLOSURE OF THE INVENTION

Problems to be Solved by the Invention

An object of the present invention is to provide a humanized anti-CD47 antibody with reduced antigenicity. Another object of the present invention is to provide a small antibody fragment of the humanized anti-CD47 antibody obtained as above. Still another object of the present invention is to provide a stabilized version of the small humanized antibody fragment obtained as above.

Means for Solving the Problems

As a result of careful studies to attain the above objects, we found humanized anti-CD47 antibodies with reduced antigenicity retaining the CD47-binding activity and apoptosis-inducing activity, and therefore useful as therapeutic agents for hematological disorders.

Accordingly, the present invention provides the following:
  [1] A humanized antibody binding to CD47.
  [2] The humanized antibody as defined in [1] above, wherein CD47 is human CD47.
  [3] The humanized antibody as defined in [1] or [2] above, wherein the CDRs of the humanized antibody are derived from a mouse antibody.
  [4] The humanized antibody as defined in any one of [1] to [3] above, comprising any one of the sequence sets below:
    (1) the sequence of aa 31-35 (CDR1), the sequence of aa 50-66 (CDR2), and the sequence of aa 99-106 (CDR3) of SEQ ID NO: 93;
    (2) the sequence of aa 31-35 (CDR1), the sequence of aa 50-66 (CDR2), and the sequence of aa 99-106 (CDR3) of SEQ ID NO: 94;
    (3) the sequence of aa 31-35 (CDR1), the sequence of aa 50-66 (CDR2), and the sequence of aa 99-106 (CDR3) of SEQ ID NO: 95;
    (4) the sequence of aa 31-35 (CDR1), the sequence of aa 50-66 (CDR2), and the sequence of aa 99-106 (CDR3) of SEQ ID NO: 96;
    (5) the sequence of aa 31-35 (CDR1), the sequence of aa 50-66 (CDR2), and the sequence of aa 99-106 (CDR3) of SEQ ID NO: 97
    (6) the sequence of aa 31-35 (CDR1), the sequence of aa 50-66 (CDR2), and the sequence of aa 99-106 (CDR3) of SEQ ID NO: 98;
    (7) the sequence of aa 31-35 (CDR1), the sequence of aa 50-66 (CDR2), and the sequence of aa 99-106 (CDR3) of SEQ ID NO: 99;
    (8) the sequence of aa 24-39 (CDR1), the sequence of aa 55-61 (CDR2), and the sequence of aa 94-102 (CDR3) of SEQ ID NO: 100;
    (9) the sequence of aa 24-39 (CDR1), the sequence of aa 55-61 (CDR2), and the sequence of aa 94-102 (CDR3) of SEQ ID NO: 101;
    (10) the sequence of aa 24-39 (CDR1), the sequence of aa 55-61 (CDR2), and the sequence of aa 94-102 (CDR3) of SEQ ID NO: 102;
    (11) the sequence of aa 24-39 (CDR1), the sequence of aa 55-61 (CDR2), and the sequence of aa 94-102 (CDR3) of SEQ ID NO: 103;
    (12) the sequence of aa 24-39 (CDR1), the sequence of aa 55-61 (CDR2), and the sequence of aa 94-102 (CDR3) of SEQ ID NO: 104;

(13) the sequence of aa 24-39 (CDR1), the sequence of aa 55-61 (CDR2), and the sequence of aa 94-102 (CDR3) of SEQ ID NO: 105;

(14) the sequence of aa 24-39 (CDR1), the sequence of aa 55-61 (CDR2), and the sequence of aa 94-102 (CDR3) of SEQ ID NO: 106;

(15) the sequence of aa 31-35 (CDR1), the sequence of aa 50-66 (CDR2), and the sequence of aa 99-106 (CDR3) of SEQ ID NO: 107; and

(16) the sequence of aa 24-39 (CDR1), the sequence of aa 55-61 (CDR2), and the sequence of aa 94-102 (CDR3) of SEQ ID NO: 108.

[5] The humanized antibody as defined in any one of [1] to [3] above, comprising any one of the sequence sets below:

(1) the sequence of aa 1-30 (FR1), the sequence of aa 36-49 (FR2), the sequence of aa 67-98 (FR3), and the sequence of aa 107-117 (FR4) of SEQ ID NO: 93;

(2) the sequence of aa 1-30 (FR1), the sequence of aa 36-49 (FR2), the sequence of aa 67-98 (FR3), and the sequence of aa 107-117 (FR4) of SEQ ID NO: 94;

(3) the sequence of aa 1-30 (FR1), the sequence of aa 36-49 (FR2), the sequence of aa 67-98 (FR3), and the sequence of aa 107-117 (FR4) of SEQ ID NO: 95;

(4) the sequence of aa 1-30 (FR1), the sequence of aa 36-49 (FR2), the sequence of aa 67-98 (FR3), and the sequence of aa 107-117 (FR4) of SEQ ID NO: 96;

(5) the sequence of aa 1-30 (FR1), the sequence of aa 36-49 (FR2), the sequence of aa 67-98 (FR3), and the sequence of aa 107-117 (FR4) of SEQ ID NO: 97;

(6) the sequence of aa 1-30 (FR1), the sequence of aa 36-49 (FR2), the sequence of aa 67-98 (FR3), and the sequence of aa 107-117 (FR4) of SEQ ID NO: 98;

(7) the sequence of aa 1-30 (FR1), the sequence of aa 36-49 (FR2), the sequence of aa 67-98 (FR3), and the sequence of aa 107-117 (FR4) of SEQ ID NO: 99;

(8) the sequence of aa 1-23 (FR1), the sequence of aa 40-54 (FR2), the sequence of aa 62-93 (FR3), and the sequence of aa 103-112 (FR4) of SEQ ID NO: 100;

(9) the sequence of aa 1-23 (FR1), the sequence of aa 40-54 (FR2), the sequence of aa 62-93 (FR3), and the sequence of aa 103-112 (FR4) of SEQ ID NO: 101;

(10) the sequence of aa 1-23 (FR1), the sequence of aa 40-54 (FR2), the sequence of aa 62-93 (FR3), and the sequence of aa 103-112 (FR4) of SEQ ID NO: 102;

(11) the sequence of aa 1-23 (FR1), the sequence of aa 40-54 (FR2), the sequence of aa 62-93 (FR3), and the sequence of aa 103-112 (FR4) of SEQ ID NO: 103;

(12) the sequence of aa 1-23 (FR1), the sequence of aa 40-54 (FR2), the sequence of aa 62-93 (FR3), and the sequence of aa 103-112 (FR4) of SEQ ID NO: 104;

(13) the sequence of aa 1-23 (FR1), the sequence of aa 40-54 (FR2), the sequence of aa 62-93 (FR3), and the sequence of aa 103-112 (FR4) of SEQ ID NO: 105;

(14) the sequence of aa 1-23 (FR1), the sequence of aa 40-54 (FR2), the sequence of aa 62-93 (FR3), and the sequence of aa 103-112 (FR4) of SEQ ID NO: 106;

(15) the sequence of aa 1-30 (FR1), the sequence of aa 36-49 (FR2), the sequence of aa 67-98 (FR3), and the sequence of aa 107-117 (FR4) of SEQ ID NO: 107; and

(16) the sequence of aa 1-23 (FR1), the sequence of aa 40-54 (FR2), the sequence of aa 62-93 (FR3), and the sequence of aa 103-112 (FR4) of SEQ ID NO: 108.

[6] The humanized antibody as defined in any one of [1]-[5] above, which is a small antibody fragment.

[7] The humanized antibody as defined in [6] above, which is a diabody.

[8] The humanized antibody as defined in [7] above, which is a single-chain diabody.

[9] The humanized antibody as defined in [7] or [8] above, characterized in that a disulfide bond exists between diabody-forming fragments.

[10] The humanized antibody as defined in [9] above characterized by:

(1) an antibody having the amino acid sequence of SEQ ID NO: 90; or (2) an antibody having an amino acid sequence containing a deletion, addition or substitution of one or several amino acid(s) in the amino acid sequence of (1) and having CD47-binding activity.

[11] The humanized antibody as defined in [9] above characterized by:

(1) an antibody having the amino acid sequence of SEQ ID NO: 92; or (2) an antibody having an amino acid sequence containing a deletion, addition or substitution of one or several amino acid(s) in the amino acid sequence of (1) and having CD47-binding activity.

[12] A diabody antibody binding to human CD47, characterized in that a disulfide bond exists between diabody-forming fragments.

[13] The diabody antibody as defined in [12] above comprising any one of the sequence sets below:

(1) the sequence of aa 31-35 (CDR1), the sequence of aa 50-66 (CDR2), and the sequence of aa 99-106 (CDR3) of SEQ ID NO: 93;

(2) the sequence of aa 31-35 (CDR1), the sequence of aa 50-66 (CDR2), and the sequence of aa 99-106 (CDR3) of SEQ ID NO: 94;

(3) the sequence of aa 31-35 (CDR1), the sequence of aa 50-66 (CDR2), and the sequence of aa 99-106 (CDR3) of SEQ ID NO: 95;

(4) the sequence of aa 31-35 (CDR1), the sequence of aa 50-66 (CDR2), and the sequence of aa 99-106 (CDR3) of SEQ ID NO: 96;

(5) the sequence of aa 31-35 (CDR1), the sequence of aa 50-66 (CDR2), and the sequence of aa 99-106 (CDR3) of SEQ ID NO: 97

(6) the sequence of aa 31-35 (CDR1), the sequence of aa 50-66 (CDR2), and the sequence of aa 99-106 (CDR3) of SEQ ID NO: 98;

(7) the sequence of aa 31-35 (CDR1), the sequence of aa 50-66 (CDR2), and the sequence of aa 99-106 (CDR3) of SEQ ID NO: 99;

(8) the sequence of aa 24-39 (CDR1), the sequence of aa 55-61 (CDR2), and the sequence of aa 94-102 (CDR3) of SEQ ID NO: 100;

(9) the sequence of aa 24-39 (CDR1), the sequence of aa 55-61 (CDR2), and the sequence of aa 94-102 (CDR3) of SEQ ID NO: 101;

(10) the sequence of aa 24-39 (CDR1), the sequence of aa 55-61 (CDR2), and the sequence of aa 94-102 (CDR3) of SEQ ID NO: 102;

(11) the sequence of aa 24-39 (CDR1), the sequence of aa 55-61 (CDR2), and the sequence of aa 94-102 (CDR3) of SEQ ID NO: 103;

(12) the sequence of aa 24-39 (CDR1), the sequence of aa 55-61 (CDR2), and the sequence of aa 94-102 (CDR3) of SEQ ID NO: 104;

(13) the sequence of aa 24-39 (CDR1), the sequence of aa 55-61 (CDR2), and the sequence of aa 94-102 (CDR3) of SEQ ID NO: 105;

(14) the sequence of aa 24-39 (CDR1), the sequence of aa 55-61 (CDR2), and the sequence of aa 94-102 (CDR3) of SEQ ID NO: 106;

(15) the sequence of aa 31-35 (CDR1), the sequence of aa 50-66 (CDR2), and the sequence of aa 99-106 (CDR3) of SEQ ID NO: 107; and

(16) the sequence of aa 24-39 (CDR1), the sequence of aa 55-61 (CDR2), and the sequence of aa 94-102 (CDR3) of SEQ ID NO: 108.

[14] A humanized antibody binding to CD47 comprising:
(1) a heavy chain variable region containing the sequence of aa 1-117 of SEQ ID NO: 99: and
(2) a light chain variable region containing the sequence of aa 1-112 of SEQ ID NO: 106.

[15] A humanized antibody binding to CD47 comprising:
(1) a heavy chain variable region containing the sequence of aa 1-117 of SEQ ID NO: 107: and
(2) a light chain variable region containing the sequence of aa 1-112 of SEQ ID NO: 108.

[16] An antibody binding to CD47 comprising any one of:
(1) the sequence of aa 1-234 of SEQ ID NO: 110;
(2) the sequence of aa 1-234 of SEQ ID NO: 111;
(3) the sequence of aa 1-483 of SEQ ID NO: 113; and
(4) the sequence of aa 1-483 of SEQ ID NO: 114.

[17] A gene encoding the antibody as defined in any one of [1]-[16] above.

[18] A vector containing the gene as defined in [17] above.

[19] A host cell containing the vector as defined in [18] above.

[20] A process for preparing an antibody, comprising the step of culturing the host cell as defined in [19] above.

[21] A therapeutic agent for hematological disorder, comprising the antibody as defined in any one of [1]-[16] above.

[22] The therapeutic agent as defined in [21] above, wherein the hematological disorder is selected from leukemias such as acute myelocytic leukemia, chronic myelocytic leukemia, acute lymphocytic leukemia, chronic lymphocytic leukemia, adult T-cell leukemia, multiple myeloma, mixed leukemia, and hairy cell leukemia; malignant lymphoma (Hodgkin's disease, non-Hodgkin's lymphoma), aplastic anemia, myelodysplastic syndromes, and polycythemia vera.

THE MOST PREFERRED EMBODIMENTS OF THE INVENTION

CD47

Figure 1:
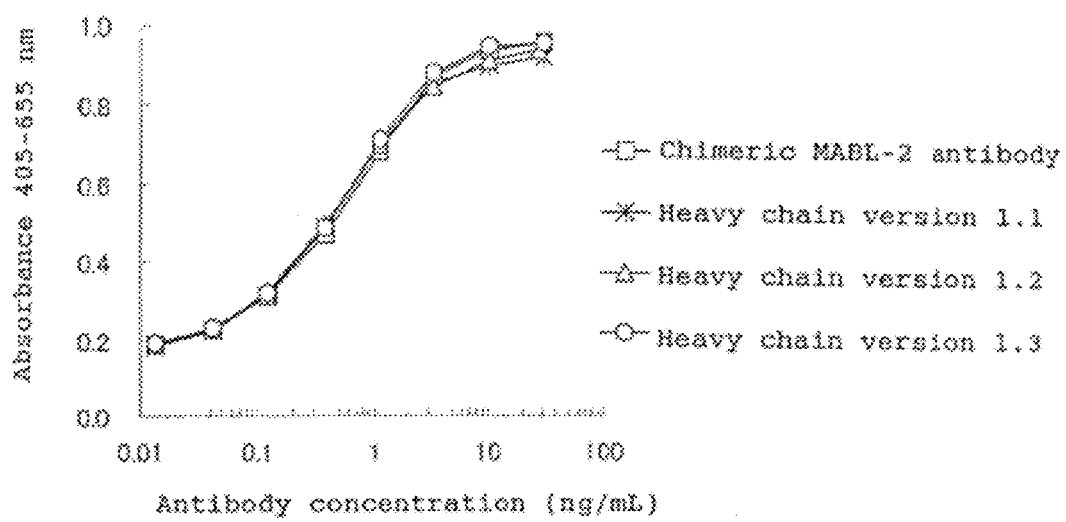
FIG. 1 is a graph showing that the antibodies combining humanized H chain versions 1.1, 1.2 and 1.3 with a chimeric L chain have human IAP-binding activities comparable to that of the chimeric antibody.

The CD47 used in the present invention is not specifically limited and may be derived from any animal, but preferably derived from mammals, more preferably human CD47. The amino acid sequence and nucleotide sequence of human CD47 have already been known (J. Cell. Biol., 123, 485-496, (1993), Journal of Cell Science, 108, 3419-3425, (1995), GenBank: Z25521).

In the present invention, anti-CD47 antibodies are not specifically limited so far as they have the ability to bind CD47, and mouse antibodies, human antibodies, rabbit antibodies, sheep antibodies and the like can be used as appropriate. Recombinant antibodies, i.e. antibodies artificially modified to reduce antigenicity in humans or for other purposes, such as chimeric antibodies and humanized antibodies can also be used. Moreover, anti-CD47 antibodies of the present invention preferably have the property of inducing apoptosis in cells expressing CD47 (e.g., myeloid cells, lymphocytes, etc.).

Humanized Antibodies

The present invention relates to humanized anti-CD47 antibodies.

The variable domains (V domains) of each pair of light and heavy chains of antibodies form the antigen-binding site, and the variable domains on the light and heavy chains each comprises four relatively conserved framework regions (FRs) having a commonality connected by three hypervariable or complementarity determining regions (CDRs) (Kabat, E. A. et al., "Sequences of Proteins of Immunological Interest" US Dept. Health and Human Services, 1983).

The four framework regions (FRs) largely adopt a β-sheet conformation, whereby the three CDRs form loops connecting, and in some cases forming part of the β-sheet structure. The three CDRs are sterically held in close proximity by the FRs and with the three CDRs from the other domain contribute to the formation of the antigen binding site.

These CDRs can be found by comparing the amino acid sequence of the variable domains of a given antibody with the known amino acid sequence of the variable domain of a known antibody according to the empirical rule described in Kabat, E. A. et al., "Sequences of Proteins of Immunological Interest".

Humanized antibodies are also called reshaped human antibodies and obtained by grafting the complementarity-determining regions (CDRs) of an antibody from a non-human animal such as a mouse antibody into the complementarity-determining regions of a human antibody and typical gene recombination techniques for preparing them are also known (see European Patent Publication EP 125023, WO 96/02576).

Specifically, when the non-human animal is a mouse, DNA sequences designed to link the CDRs of a mouse antibody to the framework regions of a human antibody are synthesized by PCR using several oligonucleotides prepared to have terminal overlapping regions of both CDRs and FRs as primers (see the method described in WO 98/13388).

The framework regions of the human antibody linked by the CDRs are selected in such a manner that the complementarity-determining regions form an appropriate antigen-binding site. If necessary, reshaped humanized antibodies may have some amino acid changes in the framework regions of the variable regions of the antibodies so that the complementarity-determining regions form an appropriate antigen-binding site (Sato, K. et al., Cancer Res. (1993) 53, 851-856).

The light chain variable regions of a humanized antibody contain the framework regions (FRs) of the light chain variable region of a human-derived antibody and the CDRs of the light chain variable regions of a non-human animal-derived antibody; and the heavy chain variable regions of a humanized antibody contain the framework regions (FRs) of the heavy chain variable region of the human-derived antibody and the CDRs of the heavy chain variable regions of the non-human animal-derived antibody.

The constant regions of the humanized antibody typically consist of those of the human antibody, e.g. Cγ1, Cγ2, Cγ3 and Cγ4 in the heavy chain and Cκ and Cλ in the light chain. The constant regions of the human antibody can be modified to improve the stability of the antibody or production thereof.

The non-human animal-derived antibodies are not limited, specifically limited, and include antibodies derived from any non-human animals such as mice, rats, hamsters, dogs and monkeys, but preferably non-human mammal-derived antibodies, more preferably rodent-derived antibodies, especially mouse antibodies.

The amino acid sequences of the FRs from humans and the CDRs from non-human animals may be partially modified (e.g., deleted, substituted or added).

The amino acid sequences of the CDRs and FRs of humanized anti-CD47 antibodies of the present invention are not specifically limited so far as CD47-binding activity is retained, and any sequence can be used. The CDRs preferably have any one of the amino acid sequence sets below:

(1) the sequence of aa 31-35 (CDR1), the sequence of aa 50-66 (CDR2), and the sequence of aa 99-106 (CDR3) of SEQ ID NO: 93;

(2) the sequence of aa 31-35 (CDR1), the sequence of aa 50-66 (CDR2), and the sequence of aa 99-106 (CDR3) of SEQ ID NO: 94;

(3) the sequence of aa 31-35 (CDR1), the sequence of aa 50-66 (CDR2), and the sequence of aa 99-106 (CDR3) of SEQ ID NO: 95;

(4) the sequence of aa 31-35 (CDR1), the sequence of aa 50-66 (CDR2), and the sequence of aa 99-106 (CDR3) of SEQ ID NO: 96;

(5) the sequence of aa 31-35 (CDR1), the sequence of aa 50-66 (CDR2), and the sequence of aa 99-106 (CDR3) of SEQ ID NO: 97
(6) the sequence of aa 31-35 (CDR1), the sequence of aa 50-66 (CDR2), and the sequence of aa 99-106 (CDR3) of SEQ ID NO: 98;
(7) the sequence of aa 31-35 (CDR1), the sequence of aa 50-66 (CDR2), and the sequence of aa 99-106 (CDR3) of SEQ ID NO: 99;
(8) the sequence of aa 24-39 (CDR1), the sequence of aa 55-61 (CDR2), and the sequence of aa 94-102 (CDR3) of SEQ ID NO: 100;
(9) the sequence of aa 24-39 (CDR1), the sequence of aa 55-61 (CDR2), and the sequence of aa 94-102 (CDR3) of SEQ ID NO: 101;
(10) the sequence of aa 24-39 (CDR1), the sequence of aa 55-61 (CDR2), and the sequence of aa 94-102 (CDR3) of SEQ ID NO: 102;
(11) the sequence of aa 24-39 (CDR1), the sequence of aa 55-61 (CDR2), and the sequence of aa 94-102 (CDR3) of SEQ ID NO: 103;
(12) the sequence of aa 24-39 (CDR1), the sequence of aa 55-61 (CDR2), and the sequence of aa 94-102 (CDR3) of SEQ ID NO: 104;
(13) the sequence of aa 24-39 (CDR1), the sequence of aa 55-61 (CDR2), and the sequence of aa 94-102 (CDR3) of SEQ ID NO: 105;
(14) the sequence of aa 24-39 (CDR1), the sequence of aa 55-61 (CDR2), and the sequence of aa 94-102 (CDR3) of SEQ ID NO: 106;
(15) the sequence of aa 31-35 (CDR1), the sequence of aa 50-66 (CDR2), and the sequence of aa 99-106 (CDR3) of SEQ ID NO: 107; and
(16) the sequence of aa 24-39 (CDR1), the sequence of aa 55-61 (CDR2), and the sequence of aa 94-102 (CDR3) of SEQ ID NO: 108.

The FRs preferably have any one of the amino acid sequence sets below:
(1) the sequence of aa 1-30 (FR1), the sequence of aa 36-49 (FR2), the sequence of aa 67-98 (FR3), and the sequence of aa 107-117 (FR4) of SEQ ID NO: 93;
(2) the sequence of aa 1-30 (FR1), the sequence of aa 36-49 (FR2), the sequence of aa 67-98 (FR3), and the sequence of aa 107-117 (FR4) of SEQ ID NO: 94;
(3) the sequence of aa 1-30 (FR1), the sequence of aa 36-49 (FR2), the sequence of aa 67-98 (FR3), and the sequence of aa 107-117 (FR4) of SEQ ID NO: 95;
(4) the sequence of aa 1-30 (FR1), the sequence of aa 36-49 (FR2), the sequence of aa 67-98 (FR3), and the sequence of aa 107-117 (FR4) of SEQ ID NO: 96;
(5) the sequence of aa 1-30 (FR1), the sequence of aa 36-49 (FR2), the sequence of aa 67-98 (FR3), and the sequence of aa 107-117 (FR4) of SEQ ID NO: 97;
(6) the sequence of aa 1-30 (FR1), the sequence of aa 36-49 (FR2), the sequence of aa 67-98 (FR3), and the sequence of aa 107-117 (FR4) of SEQ ID NO: 98;
(7) the sequence of aa 1-30 (FR1), the sequence of aa 36-49 (FR2), the sequence of aa 67-98 (FR3), and the sequence of aa 107-117 (FR4) of SEQ ID NO: 99;
(8) the sequence of aa 1-23 (FR1), the sequence of aa 40-54 (FR2), the sequence of aa 62-93 (FR3), and the sequence of aa 103-112 (FR4) of SEQ ID NO: 100;
(9) the sequence of aa 1-23 (FR1), the sequence of aa 40-54 (FR2), the sequence of aa 62-93 (FR3), and the sequence of aa 103-112 (FR4) of SEQ ID NO: 101;
(10) the sequence of aa 1-23 (FR1), the sequence of aa 40-54 (FR2), the sequence of aa 62-93 (FR3), and the sequence of aa 103-112 (FR4) of SEQ ID NO: 102;
(11) the sequence of aa 1-23 (FR1), the sequence of aa 40-54 (FR2), the sequence of aa 62-93 (FR3), and the sequence of aa 103-112 (FR4) of SEQ ID NO: 103;
(12) the sequence of aa 1-23 (FR1), the sequence of aa 40-54 (FR2), the sequence of aa 62-93 (FR3), and the sequence of aa 103-112 (FR4) of SEQ ID NO: 104;
(13) the sequence of aa 1-23 (FR1), the sequence of aa 40-54 (FR2), the sequence of aa 62-93 (FR3), and the sequence of aa 103-112 (FR4) of SEQ ID NO: 105;
(14) the sequence of aa 1-23 (FR1), the sequence of aa 40-54 (FR2), the sequence of aa 62-93 (FR3), and the sequence of aa 103-112 (FR4) of SEQ ID NO: 106;
(15) the sequence of aa 1-30 (FR1), the sequence of aa 36-49 (FR2), the sequence of aa 67-98 (FR3), and the sequence of aa 107-117 (FR4) of SEQ ID NO: 107; and
(16) the sequence of aa 1-23 (FR1), the sequence of aa 40-54 (FR2), the sequence of aa 62-93 (FR3), and the sequence of aa 103-112 (FR4) of SEQ ID NO: 108.

Preparation of Anti-CD47 Antibodies and CDR Sequences

The CDR sequences of antibodies derived from non-human animals can be obtained by methods known to those skilled in the art.

First, an anti-CD47 antibody is prepared by a method known to those skilled in the art. For example, the CD47 protein or a partial peptide is used as an immunizing antigen to immunize host cells according to a standard immunization technique, and the resulting immunized cells are fused to known parent cells by a standard cell fusion technique, and then the fused cells are screened for monoclonal antibody-producing cells by a standard screening method. Specifically, monoclonal antibodies can be prepared as follows.

First, the CD47 protein used as an immunizing antigen is expressed with reference to the gene/amino acid sequence of CD47 disclosed in GenBank: Z25521 or the like. That is, the gene sequence encoding CD47 is inserted into a known expression vector system to transform suitable host cells, and then the desired CD47 protein is purified from the host cells or culture supernatants by a known method.

Then, this purified CD47 protein is used as an immunizing antigen. Alternatively, a partial peptide of CD47 can also be used as an immunizing antigen. Such a partial peptide can be chemically synthesized from the amino acid sequence of CD47.

The epitope on the CD47 molecule recognized by anti-CD47 antibodies is not specifically limited, but any epitope present on the CD47 molecule may be recognized. Thus, any fragment containing an epitope present on the CD47 molecule can be used as an antigen for preparing an anti-CD47 antibody.

Non-human animals immunized with the immunizing antigen are not specifically limited, but preferably selected considering the compatibility with parent cells used for cell fusion, and rodents such as mice, rats and hamsters or rabbits or monkeys or the like are typically used.

Animals are immunized with the immunizing antigen according to known methods. For example, a typical method is intraperitoneal or subcutaneous injection of an immunizing antigen into a non-human animal. Specifically, an immunizing antigen is diluted or suspended to an appropriate volume in PBS (Phosphate-Buffered Saline) or physiological saline and, if desired, mixed with an appropriate amount of a conventional adjuvant such as Freund's complete adjuvant, and emulsified and then administered to a mammal several times every 4-21 days. A suitable carrier can be used during immunization with the immunizing antigen.

After immunizing the non-human animal in this manner and confirming an increase in the serum level of a desired antibody, immunized cells, preferably spleen cells are collected from the non-human animal and used for cell fusion.

Myeloma cells from mammals are used as parent cells to which the immunized cells are fused. Suitable myeloma cells include those derived from various known cell lines such as P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323) and R210 (Galfre, G. et al., Nature (1979) 277, 131-133).

Cell fusion of the immunized cells to myeloma cells can be performed basically according to known methods, such as the method of Kohler and Milstein et al. (Kohler. G. and Milstein, C., Methods Enzymol. (1981) 73: 3-46).

More specifically, the cell fusion is performed in a conventional nutrient culture medium in the presence of for e.g. a cell fusion promoter such as polyethylene glycol (PEG) or Sendai virus (HVJ) and, if desired, an additive for improving the fusion efficiency such as dimethyl sulfoxide.

Immunized cells and myeloma cells can be used in any ratio. For example, the ratio of immunized cells to myeloma cells is preferably 1-10. Suitable culture media for the cell fusion include, for example, RPMI1640 and MEM well-suitable for culturing the myeloma cell lines mentioned above and other conventional culture media used for this type of cell culture, optionally in combination with serum supplements such as fetal calf serum (FCS).

Cell fusion is performed by thoroughly mixing given amounts of the immunized cells and myeloma cells in the culture medium, adding a PEG solution (e.g. average molecular weight of about 1000-6000) pre-heated normally at about 37° C. at a concentration of 30-60% (w/v) to the mixture and mixing the cell solution to form desired fused cells (hybridomas). Subsequently, cell fusion promoters or the like that are undesirable for the growth of hybridomas are removed by repeating the steps of gradually adding a suitable culture medium and centrifuging the mixture to remove supernatants.

Thus obtained hybridomas are selected by incubation in a conventional selective culture medium such as a HAT (a culture medium comprising hypoxanthine, aminopterin and thymidine). The incubation in the HAT medium is continued for a sufficient period to kill cells other than desired hybridomas (non-fused cells) (typically, several days to several weeks). Then, hybridomas producing a desired antibody are screened by conventional limiting dilution and single copies are cloned.

Hybridomas producing monoclonal antibodies prepared in this manner can be subcultured in conventional culture media and stored for a long period in liquid nitrogen.

Monoclonal antibodies can be obtained from said hybridomas as culture supernatants by culturing said hybridomas according to conventional methods or as ascites by growing said hybridomas in a mammal compatible with them. The former method is suitable for obtaining high-purity antibodies while the latter method is suitable for mass production of antibodies.

Then, the mRNA sequences encoding the variable regions (V regions) of an anti-CD47 antibody are isolated from hybridomas producing the anti-CD47 antibody. The mRNA is isolated by known methods such as guanidine ultracentrifugation (Chirgwin, J. M. et al., Biochemistry (1979) 18, 5294-5299), guanidine thiocyanate-hot phenol method, guanidine thiocyanate-guanidine hydrochloride method, guanidine thiocyanate-cesium chloride method, alkaline sucrose density gradient centrifugation, AGPC method (Chomczynski, P. et al., Anal. Biochem. (1987) 162, 156-159) to prepare total RNA, from which a desired mRNA is prepared using an mRNA Purification Kit (Pharmacia) or other means. The mRNA can also be directly prepared by using a QuickPrep mRNA Purification Kit (Pharmacia).

The cDNA sequences for the antibody V regions are synthesized from the mRNA obtained above using a reverse transcriptase. The cDNA is synthesized using an AMV Reverse Transcriptase First-strand cDNA Synthesis Kit (Seikagaku) or the like. The cDNA can be synthesized and amplified by 5'-RACE (Frohman, M. A. et al., Proc. Natl. Acad. Sci. USA (1988) 85, 8998-9002, Belyaysky, A. et al., Nucleic Acids Res. (1989) 17, 2919-2932) using a 5'-Ampli FINDER RACE Kit (Clontech) and PCR or the like.

A desired DNA fragment is purified from the resulting PCR product and fused to a vector DNA. Then, a recombinant vector is prepared from the fused system and transferred into *E. coli* or the like and colonies are selected to prepare a desired recombinant vector. Then, the nucleotide sequence of a desired DNA is confirmed by known methods such as dideoxynucleotide chain termination.

FR Sequences

As human-derived FR sequences, known human antibodies having already explained amino acid sequences can be used. For example, the sequences of natural human antibodies deposited in the Protein Data Bank can be used.

FR sequences used can be selected by any method such as separately selecting the sequences of heavy and light chains having the highest homology to those of the FR sequences of the antibody from which the CDR sequences are derived, or directly selecting the combination of the heavy and light chains of a single human antibody, or separately selecting heavy and light chains from the same subgroup.

Modified Antibodies

Antibodies of the present invention also include modified antibodies obtained by conjugating antibodies with various molecules. The modified antibodies include antibodies conjugated with various molecules such as cytotoxic agents or polyethylene glycol (PEG). Cytotoxic agents include, e.g., radioisotopes, chemotherapeutic agents, cellular toxins, etc. Modified antibodies conjugated with such other agents are also included in the "antibodies" of the present invention. Such modified antibodies can be obtained by chemically modifying the antibodies produced as above. Methods for modifying antibodies have already been established in this field of art.

Bispecific antibody may also be included. Bispecific antibodies may have antigen-binding sites recognizing different epitopes on the CD47 molecule or may have one antigen-binding site recognizing CD47 and another antigen-binding site recognizing another agent such as a cytotoxic agent. Bispecific antibodies can be prepared by genetic engineering techniques.

Techniques for modifying oligosaccharides on antibodies for the purpose of increasing cytotoxicity are also known (see e.g., WO00/61739, WO02/31140, etc.).

Small Antibody Fragments

Antibodies of the present invention are preferably small antibody fragments.

As used herein, the small antibody fragments include antibody fragments obtained by removing a part of whole antibodies (e.g., whole IgG, etc.) and are not specifically limited so far as they retain antigen-binding ability. Antibody fragments of the present invention are not specifically limited so far as they form a part of whole antibodies, but preferably contain a heavy chain variable region (VH) or a light chain variable region (VL), especially both VH and VL. Specific examples of antibody fragments include, e.g., Fab, Fab', F(ab')2, Fv, scFv (single-chain Fv), etc., preferably scFv (Huston, J. S. et al., Proc. Natl. Acad. Sci. U.S.A. (1988) 85, 5879-5883, Plickthun "The Pharmacology of Monoclonal Antibodies" Vol. 113, Resenburg and Moore (ed), Springer Verlag, New York, pp. 269-315, (1994)). Such antibody fragments can be obtained by treating antibodies with an enzyme such as papain or pepsin to produce antibody fragments or by constructing genes encoding these antibody fragments and introducing them into an expression vector and then expressing them in a suitable host cell (e.g., see Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Preferred small antibody fragments in the present invention are diabodies. Diabody is a dimer consisting of two fragments, each having variable regions joined together via a linker or the like (e.g., scFv, etc.) (hereinafter referred to as diabody-forming fragments), and typically contain two VLs and two VHs (P. Holliger et al., Proc. Natl. Acad. Sci. USA, 90, 6444-6448 (1993), EP404097, WO93/11161, Johnson et al., Method in Enzymology, 203, 88-98, (1991), Holliger et al., Protein Engineering, 9, 299-305, (1996), Perisic et al., Structure, 2, 1217-1226, (1994), John et al., Protein Engineering, 12(7), 597-604, (1999), Holliger et al., Proc. Natl. Acad. Sci. USA., 90, 6444-6448, (1993), Atwell et al., Mol. Immunol. 33, 1301-1312, (1996)).

Diabody-forming fragments include those consisting of VL and VH, VL and VL, VH and VH, etc., preferably VH and VL. In diabody-forming fragments, the linker joining variable regions is not specifically limited, but preferably enough short to avoid noncovalent bonds between variable regions in the same fragment. The length of such a linker can be determined as appropriate by those skilled in the art, but typically 2-14 amino acids, preferably 3-9 amino acids, especially 4-6 amino acids. In this case, the VL and VH encoded on the same fragment are joined via a linker short enough to avoid noncovalent bonds between the VL and VH on the same chain and to avoid the formation of single-chain variable region fragments so that dimers with another fragment can be formed. The dimers can be formed via either covalent or noncovalent bonds or both between diabody-forming fragments. Covalent bonds refer to bonds stabilized by sharing outer shell electrons (e.g., disulfide bonds, etc.). Noncovalent bonds refer to interactions between atoms or molecules except for covalent bonds and include hydrogen bonds, electrostatic interactions and Van der Waals' forces.

Moreover, diabody-forming fragments can be joined via a linker or the like to form single-chain diabodies (sc(Fv)$_2$). By joining diabody-forming fragments using a long linker of about 15-20 amino acids, noncovalent bonds can be formed between diabody-forming fragments existing on the same chain to form dimers. Examples of the arrangements of single-chain diabodies include the following.

[VH] linker (5) [VL] linker (15) [VH] linker (5) [VL]
[VL] linker (5) [VH] linker (15) [VH] linker (5) [VL]
[VH] linker (5) [VL] linker (15) [VL] linker (5) [VH]
[VH] linker (5) [VH] linker (15) [VL] linker (5) [VL].

Based on the same principle as for preparing diabodies, polymerized antibodies such as trimers or tetramers can also be prepared by joining three or more diabody-forming fragments.

Stabilized Diabodies

The present invention also provides stabilized diabodies. As used herein, the stabilized diabodies refer to diabodies in which covalent bonds exist between diabody-forming fragments. The covalent bonds existing between diabody-forming fragments are not specifically limited and include any covalent bond, but disulfide bonds can be preferably used in the present invention. Disulfide bonds can be introduced into diabodies by methods known to those skilled in the art such as the method of International Publication WO94/29350, for example.

Disulfide bonds are normally introduced into diabodies by replacing a selected amino acid in the diabodies by cysteine, but can also be introduced by other methods. The number of disulfide bonds introduced into diabodies is not limited, but preferably two disulfide bonds are introduced into diabodies. In this case, a first disulfide bond is formed by a cysteine introduced into the VH of a first diabody-forming fragment and a cysteine introduced into the VL of a second diabody-forming fragment, and a second disulfide bond is formed by a cysteine introduced into the VL of the first diabody-forming fragment and a cysteine introduced into the VH of the second diabody-forming fragment.

Disulfide bonds can be introduced at any position selected as appropriate and not specifically limited, but typically disulfide bonds are introduced into the FRs because the binding activity of diabodies may be affected if disulfide bonds are introduced into the CDRs.

International Publication WO94/29350 contains a list of preferred positions for introducing disulfide bond as follows.

VH44-VL100
VH105-VL43
VH105-VL42
VH44-VL101
VH106-VL43
VH104-VL43
VH44-VL99
VH45-VL98
VH46-VL98
VH103-VL43
VH103-VL44
VH103-VL45

The aa positions indicated above are the positions in the numbering system used by Kabat and Wu. In the present invention, preferred positions include VH44-VL100 and VH105-VL43.

Linkers

In the present invention, suitable linkers joining the H chain V region and the L chain V region or linkers joining diabody-forming fragments to form single-chain diabodies include any peptide linkers that can be introduced by genetic engineering or synthetic linkers, such as linkers disclosed in Protein Engineering, 9(3), 299-305, 1996. For example, peptide linkers include:

Ser

Gly·Ser

Gly·Gly·Ser

Ser·Gly·Gly

Gly·Gly·Gly·Ser         (SEQ ID NO: 115)

Ser·Gly·Gly·Gly         (SEQ ID NO: 116)

| | |
|---|---|
| Gly·Gly·Gly·Gly·Ser | (SEQ ID NO: 109) |
| Ser·Gly·Gly·Gly·Gly | (SEQ ID NO: 117) |
| Gly·Gly·Gly·Gly·Gly·Ser | (SEQ ID NO: 118) |
| Ser·Gly·Gly·Gly·Gly·Gly | (SEQ ID NO: 119) |
| Gly·Gly·Gly·Gly·Gly·Gly·Ser | (SEQ ID NO: 120) |
| Ser·Gly·Gly·Gly·Gly·Gly·Gly | (SEQ ID NO: 121) |
| (Gly·Gly·Gly·Gly·Ser)n | (SEQ ID NO: 109) |
| (Ser·Gly·Gly·Gly·Gly)n | (SEQ ID NO: 117) | wherein n is an integer of 1 or more. The length of linker peptides can be selected as appropriate by those skilled in the art depending on the purpose.

Synthetic linkers (chemical crosslinkers) in the present invention include crosslinkers normally used for crosslinking peptides such as N-hydroxysuccinimide (NHS), disuccinimidyl suberate (DSS), bis(sulfosuccinimidyl) suberate ($BS^3$), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimide oxycarbonyloxy)ethyl]sulfone (BSOCOES), bis[2-(sulfosuccinimide oxycarbonyloxy)ethyl]sulfone (sulfo-BSOCOES), and these crosslinkers are commercially available.

Especially, when a diabody is to be prepared it is preferable to select a linker suitable for dimerizing diabody-forming fragments produced in host cells upto a dimerization degree of 20% or more, preferably 50% or more, more preferably 80% or more, most preferably 90% or more in a solution such as a medium.

Preparation of Antibodies

The genes encoding the antibodies of the present invention obtained above can be expressed by known methods. In mammalian cells, expression can be accomplished by operably linking conventional useful promoters, a gene to be expressed and a polyA signal downstream of the 3' end. For example, promoters/enhancers include human cytomegalovirus immediate early promoters/enhancers.

Other promoters/enhancers that can be used for the antibody expression in the present invention include viral promoters/enhancers derived from retroviruses, polyomaviruses, adenoviruses, simian virus 40 (SV40) or the like or promoters/enhancers derived from mammalian cells such as human elongation factor 1α (HEF1α).

Gene expression can be readily performed by the method of Mulligan et al. (Nature (1979) 277, 108) using SV40 promoters/enhancers or by the method of Mizushima et al. (Nucleic Acids Res. (1990) 18, 5322) using HEF1α promoters/enhancers.

In E. coli, the gene can be expressed by operably linking conventional useful promoters, a signal sequence for secreting the antibody and the gene to be expressed. Promoters include e.g. lacz promoter and araB promoter. It can be expressed by the method of Ward et al. (Nature (1098) 341, 544-546; FASEB J. (1992) 6, 2422-2427) using lacz promoter or the method of Better et al. (Science (1988) 240, 1041-1043) using araB promoter.

When the antibody is to be produced in periplasms of E. coli, the pelB signal sequence (Lei, S. P. et al., J. Bacteriol. (1987) 169, 4379) can be used as a signal sequence for secreting the antibody. The antibody produced in periplasms is isolated and then used by suitably refolding the structure of the antibody.

Suitable origins of replication include those derived from SV40, polyomaviruses, adenoviruses, bovine papilloma virus (BPV), etc., and expression vectors can contain selectable markers such as the genes for aminoglycoside transferase (APH), thymidine kinase (TK), E. coli xanthine-guanine phosphoribosyl transferase (Ecogpt) and dihydrofolate reductase (dhfr) to increase the copy number of the gene in the host cell system.

Any expression system such as a eukaryotic or a prokaryotic system can be used to prepare antibodies used in the present invention. Suitable eukaryotic cells include animal cells such as established mammalian cell lines, insect cell lines, fungal cell lines and yeast cell lines, and prokaryotic cells include, e.g., bacterial cells such as E. coli cells.

Preferably, antibodies used in the present invention are expressed in mammalian cells such as CHO, COS, myeloma, BHK, Vero and HeLa cells.

Then, transformed host cells are cultured in vitro or in vivo to produce a desired antibody. The host cells are cultured by known methods. For example, DMEM, MEM, PRMI1640 and IMDM can be used as culture media optionally in combination with serum supplements such as fetal calf serum (FCS).

Antibodies expressed and produced as above can be isolated from cells or host animals and purified to homogenicity. Isolation and purification of antibodies used in the present invention can be performed on an affinity column. For example, columns using a protein A column include Hyper D, POROS and Sepharose F.F. (Pharmacia). Any other isolation and purification method conventionally used for proteins can be used without limitation. For example, antibodies can be isolated/purified by appropriately selecting and combining chromatography columns other than affinity columns above, filtration, ultrafiltration, salting, dialysis, etc. (Antibodies A Laboratory Manual. Ed Harlow, David Lane, Cold Spring Harbor Laboratory, 1988).

Evaluation of Antibody Activity

The antigen-binding activity of antibodies can be determined by known means (Antibodies A Laboratory Manual. Ed Harlow, David Lane, Cold Spring Harbor Laboratory, 1988).

Suitable methods for determining antigen-binding activity include ELISA (Enzyme-Linked Immunosorbent Assay), EIA (Enzyme Immunoassay), RIA (Radioimmunoassay) or Fluorescent Antibody Assay. When an enzyme immunoassay is used, for example, a sample containing an anti-CD47 antibody such as the culture supernatants of anti-CD47 antibody-producing cells or a purified antibody is added to a plate coated with CD47. The antigen-binding activity can be evaluated by incubating the plate with a secondary antibody labeled with an enzyme such as an alkaline phosphatase and washing it and then adding an enzyme substrate such as p-nitrophenyl phosphate and measuring the absorbance.

Evaluation of Apoptosis-inducing Activity

Whether or not apoptosis is induced can be evaluated by methods known to those skilled in the art (e.g., JPA HEI 9-295999, etc.). Specifically, evaluation can be made by the methods described in the examples below or by culturing CD47-expressing cells such as human leukemia cells or Jurkat cells, L1210 cells or JOK-1 cells containing the CD47 gene in the presence of a test antibody and detecting apoptosis by MTS or flow cytometry.

Therapeutic Agent for Hematological Disorders

The present invention also relates to therapeutic agents for hematological disorders comprising an antibody of the present invention as an active ingredient. The therapeutic agents for hematological disorders of the present invention are useful for treating hematological disorders including, e.g., leukemias such as acute myelocytic leukemia, chronic myelocytic leukemia, acute lymphocytic leukemia, chronic lymphocytic leukemia, adult T-cell leukemia, multiple myeloma, mixed leukemia, and hairy cell leukemia; malignant lymphoma (Hodgkin's disease, non-Hodgkin's lymphoma), aplastic anemia, myelodysplastic syndromes, and polycythemia vera.

When antibodies of the present invention are used as therapeutic agents for hematological disorders, effective doses are selected in the range of 0.001 mg to 1000 mg/kg body weight. Alternatively, doses can be selected at 0.01 to 100000 mg/body per patient. However, therapeutic agents containing a humanized anti-CD47 antibody of the present invention are not limited to these doses.

The therapeutic agents of the present invention can be administered before or after clinical conditions/symptoms appear.

The therapeutic agents of the present invention can be administered 1-3 times per day for 1-7 days per week. They can also be continuously administered by drip infusion or the like for e.g., 1-3 days.

Therapeutic agents of the present invention are typically administered via parenteral routes such as injection (e.g. subcutaneous, intravenous, intramuscular or intraperitoneal injection) or percutaneous, mucosal, nasal or pulmonary administration, but may also be orally administered.

However, the therapeutic agents of the present invention are not limited to the doses, ways of administration and the like described above.

Therapeutic agents containing an antibody as an active ingredient of the present invention can be routinely formulated (Remington's Pharmaceutical Science, latest edition, Mark Publishing Company, Easton, USA) optionally in combination with pharmaceutically acceptable carriers and additives.

Examples of such carriers and pharmaceutical additives include water, pharmaceutically acceptable organic solvents, collagen, polyvinyl alcohol, polyvinyl pyrrolidone, carboxy vinyl polymers, sodium carboxymethyl cellulose, sodium polyacrylate, sodium alginate, water-soluble dextran, sodium carboxymethyl starch, pectin, methyl cellulose, ethyl cellulose, xanthan gum, arabic gum, casein, agar, polyethylene glycol, diglycerin, glycerin, propylene glycol, vaseline, paraffin, stearyl alcohol, stearic acid, human serum albumin (HSA), mannitol, sorbitol, lactose, pharmaceutically acceptable surfactants, etc.

Practically used additives are selected from, but not limited to, the list above, alone or in combination as appropriate depending on the dosage form of the therapeutic agent of the present invention. For use as injection formulations, for example, a purified antibody can be dissolved in a solvent such as physiological saline, buffer, glucose solution or the like containing an adsorption inhibitor such as Tween 80, Tween 20, gelatin, human serum albumin, etc. Alternatively, freeze-dried formulations to be dissolved/reconstituted before use can contain sugar alcohols or sugars such as mannitol or glucose as excipients for freeze-drying.

Humanized anti-CD47 antibodies of the present invention induced significant cell death in L1210 cells, MOLT4 cells and JOK-1 cells containing the human CD47 gene. As a result of a test using a mouse model of human leukemia, humanized anti-CD47 antibodies of the present invention were found to show antitumor effect.

Humanized anti-CD47 antibodies of the present invention are more effectively transported to tissues or tumors than whole IgG and eliminate or remarkably reduce the side effect of hemagglutination, so that they are expected for use as therapeutic drugs for hematological disorders including, for e.g., leukemias such as acute myelocytic leukemia, chronic myelocytic leukemia, acute lymphocytic leukemia, chronic lymphocytic leukemia, adult T-cell leukemia, multiple myeloma, mixed leukemia, and hairy cell leukemia; malignant lymphoma (Hodgkin's disease, non-Hodgkin's lymphoma), aplastic anemia, myelodysplastic syndromes, and polycythemia vera. They are also expected for use as contrast agents by radioisotope labeling and their efficacy can be increased by conjugating them with radioisotope compounds or toxins.

The following examples further illustrate the present invention without, however, limiting the scope of the invention thereto. Various changes and modifications can be made by those skilled in the art on the basis of the description herein, and such changes and modifications are also included in the present invention.

EXAMPLES

Example 1

Construction of a Humanized MABL-2 Antibody

To prepare a reshaped human antibody having the CDRs of a mouse monoclonal antibody grafted to a human antibody, a high homology should desirably exist between the FRs of the mouse monoclonal antibody and the FRs of the human antibody. Thus, the L chain and H chain V regions of a mouse MABL-2 antibody (WO00/53634) were compared with the V regions of known natural human antibodies having explained structures using the Protein Data Bank.

(1) Construction of a Humanized Antibody H Chain
(i) Primary Design

Four clones showed 75.9% homology to the H chain V region of the mouse MABL-2 antibody. Among them, the human antibody AF216824 conserved at position 30 immediately upstream of CDR1 (Miklos J. A. et al., Blood, 95, 3878-3884, 2000) was selected to use the FRs therefrom because amino acids in proximity to the CDRs may be greatly involved in binding to antigens. In a humanized MABL-2 antibody H chain (version "1.1"), FR1-FR4 were identical with FR1-FR4 of the human antibody AF216824, and the CDRs were identical with the CDRs in the H chain V region of the mouse MABL-2 antibody. For lack of information of the leader sequence of AF216824, the leader sequence of the mouse MABL-2 $V_H$ was used.

The humanized MABL-2 antibody H chain (version "1.1") was prepared by CDR grafting using PCR. For preparing the humanized MABL-2 antibody H chain (version "1.1"), four synthetic oligo DNAs were used. Among the synthetic oligo DNAs, HuMHa1S (SEQ ID NO: 1) and HuMHa3S (SEQ ID NO: 2) have sense DNA sequences, while HuMHa2AS (SEQ ID NO: 3) and HuMHa4AS (SEQ ID NO: 4) have antisense DNA sequence. External primers HuMHS (SEQ ID NO: 5) and HuMHAS (SEQ ID NO: 6) have homology to the synthetic oligo DNAs HuMHa1S and HuMHa4AS.

PCR was performed using 100 μL of a reaction mixture containing 5 pmol each of the synthetic oligo DNAs HuMHa1S, HuMHa2AS, HuMHa3S and HuMHa4AS, 0.2 mmol/L dNTP and 2 U KOD -Plus- (Toyobo Ltd.) in the supplied buffer for 5 cycles of 94° C. for 15 seconds, 50° C. for 30 seconds, and 68° C. for 1 minute. Further 35 cycles were performed under the same conditions in the presence of 40 pmol of the external primers HuMHS and HuMHAS. The DNA fragments amplified by PCR were separated by agarose gel electrophoresis using 1.2% agarose.

An agarose slice containing a DNA fragment of 438 bp length was excised and the DNA fragment was purified using QIAquick PCR Purification Kit (QIAGEN) following the instruction included in the kit. The purified DNA was precipitated with ethanol and then dissolved in 50 µL of a solution containing 10 mmol/L Tris-HCl (pH 7.4), 1 mmol/L EDTA. The resulting PCR reaction mixture was subcloned into the HEF expression vector HEF-VH-gγ1 prepared by digestion with BamHI and HindIII, and the nucleotide sequence was determined. A plasmid containing a DNA fragment having the amino acid sequence of the correct H chain V region was designated HEF-huM2H1.1#1. The amino acid sequence and nucleotide sequence of the H chain V region contained in this plasmid HEF-huM2H1.1#1 are shown in SEQ ID NO: 7.

Humanized MABL-2 antibody H chain V region versions 1.2, 1.3, 1.4, 1.5 were prepared as follows.

Version 1.2 was prepared by amplifying the plasmid HEF-huM2H1.1#1 as template DNA by PCR using HuMHbS (SEQ ID NO: 8) and HuMHbAS (SEQ ID NO: 9) designed to change arginine at position 72 to serine as mutagenic primers, thereby giving a plasmid HEF-huM2H1.2#1. The amino acid sequence and nucleotide sequence of the H chain V region contained in this plasmid HEF-huM2H1.2#1 are shown in SEQ ID NO: 10.

Version 1.3 was prepared by amplifying the plasmid HEF-huM2H1.2#1 as template DNA by PCR using HuMHcS (SEQ ID NO: 11) and HuMHcAS (SEQ ID NO: 12) designed to change alanine at position 30 to threonine as mutagenic primers, thereby giving a plasmid HEF-huM2H1.3#2. The amino acid sequence and nucleotide sequence of the H chain V region contained in this plasmid HEF-huM2H1.3#2 are shown in SEQ ID NO: 13.

Version 1.4 was prepared by amplifying the plasmid HEF-huM2H1.2#1 as template DNA by PCR using HuMHdS (SEQ ID NO: 14) and HuMHdAS (SEQ ID NO: 15) designed to change arginine at position 67 to lysine as mutagenic primers, thereby giving a plasmid HEF-huM2H1.4#1. The amino acid sequence and nucleotide sequence of the H chain V region contained in this plasmid HEF-huM2H1.4#1 are shown in SEQ ID NO: 16.

Version 1.5 was prepared by amplifying the plasmid HEF-huM2H1.2#1 as template DNA by PCR using HuMHeS (SEQ ID NO: 17) and HuMHeAS (SEQ ID NO: 18) designed to change methionine at position 70 to leucine as mutagenic primers, thereby giving a plasmid HEF-huM2H1.5#1. The amino acid sequence and nucleotide sequence of the H chain V region contained in this plasmid HEF-huM2H1.5#1 are shown in SEQ ID NO: 19.

(ii) Secondary Design

Considering the conservation of the amino acid at position 72 and the highest possible conservation of FR2, homology searches were performed again for humanized MABL-2 antibody H chain version "1.3". As a result, the human antibody HUMIGHDJCD conserved at position 72 (Chai S. K. et al., Unpublished 1994) was selected to use the FRs therefrom. In humanized MABL-2 antibody H chain version "2.1", FR1-FR4 were identical with FR1-FR4 of the human antibody HUMIGHDJCD, and the CDRs were identical with the CDRs in the H chain V region of the mouse MABL-2 antibody. Also for lack of information of the leader sequence of HUMIGH-DJCD, the leader sequence of the mouse MABL-2 $V_H$ was used.

Humanized MABL-2 antibody H chain version "2.1" was prepared using version 2.0 obtained by changing aspartate at position 89 to asparagine in version "1.3" as template DNA.

First, version 2.0 was prepared by amplifying the plasmid HEF-huM2H1.3#2 as template DNA by PCR using HuMHgS (SEQ ID NO: 20) and HuMHgAS (SEQ ID NO: 21) designed to change glutamate at position 89 to aspartate in version "1.3", thereby giving a plasmid HEF-huM2H2.0#1. The amino acid sequence and nucleotide sequence of the H chain V region contained in this plasmid HEF-huM2H2.0#1 are shown in SEQ ID NO: 22.

The humanized MABL-2 antibody H chain (version "2.1") was prepared by CDR grafting using PCR. For preparing the humanized MABL-2 antibody H chain (version "2.1"), eight synthetic oligo DNAs (PCR primers) were used. Among the synthetic oligo DNAs, HuMHS (SEQ ID NO: 5), HuMHfS1 (SEQ ID NO: 23), HuMHfS (SEQ ID NO: 24), and HuMHfS3 (SEQ ID NO: 25) have sense DNA sequences, while HuMHfAS1 (SEQ ID NO: 26), HuMHfAS2 (SEQ ID NO: 27), HuMHfAS3 (SEQ ID NO: 28), and HuMHfAS (SEQ ID NO: 29) have antisense DNA sequences.

In the first PCR, HEF-huM2H2.0#1 was used as template DNA together with the following PCR primer sets. Four reactions HuMHS/HuMHfAS1, HuMHfS1/HuMHfAS2, HuMHfS2/HuMHfAS, and HuMHfS3/HuMHfAS3 were performed, and the PCR products were purified. The products huM2H2.1-1, huM2H2.1-2, huM2H2.1-3, and huM2H2.1-4 were mixed as huM2H2.1-1/huM2H2.1-2 and huM2H2.1-3/huM2H2.1-4 sets and assembled by their own complementarity and the second PCR was performed. PCR primers HuMHS/HuMHfAS2 and HuMHfS2/HuMHfAS3 were used, and the PCR products were purified. The two PCR products from the second PCR were further assembled by their own complementarity and PCR primers HuMHS and HuMHfAS3 were added to amplify the full-length DNA encoding the humanized MABL-2 antibody H chain (version "2.1") (third PCR).

The first PCR was performed using 50 µL of a reaction mixture containing 20 pmol each of the PCR primers, 0.2 mmol/L dNTP, 1 mmol/L $MgSO_4$, 5 ng of the template DNA and 1 U KOD -Plus- in the supplied buffer for 35 cycles of 94° C. for 15 seconds, 50° C. for 30 seconds, and 68° C. for 1 minute, followed by incubation at 68° C. for 7 minutes. The PCR products were purified using QIAquick PCR Purification Kit (QIAGEN) following the instructions included in the kit to give pure DNA fragments. In the second PCR, 100 µL of a reaction mixture containing 1 µL each of the first PCR products and 2 U KOD -Plus- was incubated for 5 cycles of 94° C. for 15 seconds, 50° C. for 30 seconds, and 68° C. for 1 minute, followed by incubation at 68° C. for 5 minutes, and then 40 pmol each of the PCR primers were added. Subsequently, 35 rounds of PCR were performed under the same conditions as those of the first PCR, and the PCR products were separated by electrophoresis on a 1.2% agarose gel and purified. The third PCR was performed using the second PCR product with the PCR primers in the same manner as the second PCR.

The DNA fragment of 438 bp produced by the third PCR was separated by electrophoresis on a 1.2% agarose gel and purified. The purified DNA was subcloned into the HEF expression vector HEF-VH-gγ1 prepared by digestion with BamHI and HindIII, and the nucleotide sequence was determined. A plasmid containing a DNA fragment having the amino acid sequence of the correct H chain V region was designated HEF-huM2H2.1#3. The amino acid sequence and nucleotide sequence of the H chain V region contained in this plasmid HEF-huM2H2.1#3 are shown in SEQ ID NO: 30.

(2) Construction of a Humanized MABL-2 Antibody L Chain (i) Primary Design

Two clones showed 83.8% homology to the L chain V region of the mouse MABL-2 antibody. Of these clones, the human antibody HSJC11VJ having CDR3 of the same size (Kennedy M. A., J. Exp. Med, 173(4), 1033-1036, 1991) was selected to use the FRs therefrom. In a humanized MABL-2 antibody L chain (version "1.1"), FR1-FR4 were identical with FR1-FR4 of the human antibody HSJC11VJ, and the CDRs were identical with the CDRs in the L chain V region of the mouse MABL-2 antibody. The leader sequence of the human antibody HSJC11VJ was used.

The humanized MABL-2 antibody L chain (version "1.1") was prepared by CDR grafting using PCR. For preparing the humanized MABL-2 antibody L chain (version "1.1"), four synthetic oligo DNAs were used. Among the synthetic oligo DNAs, HuMLa1S (SEQ ID NO: 31) and HuMLa3S (SEQ ID NO: 32) have sense DNA sequences, while HuMLa2AS (SEQ ID NO: 33) and HuMLa4AS (SEQ ID NO: 34) have antisense DNA sequences. External primers HuMLS (SEQ ID NO: 35) and HuMLAS (SEQ ID NO: 36) have homology to the synthetic oligo DNAs HuMLa1S and HuMLa4AS.

PCR was performed using 100 μL of a reaction mixture containing 5 pmol each of the synthetic oligo DNAs HuMLa1S, HuMLa2AS, HuMLa3S and HuMLa4AS, 0.2 mmol/L dNTP and 2 U KOD -Plus- (Toyobo Ltd.) in the supplied buffer for 5 cycles of 94° C. for 15 seconds, 50° C. for 30 seconds, and 68° C. for 1 minute. Further, 35 cycles were performed under the same conditions in the presence of 40 pmol of the external primers HuMLS and HuMLAS. The DNA fragments amplified by PCR were separated by agarose gel electrophoresis using 1.2% agarose.

An agarose slice containing a DNA fragment of 426 bp length was excised and the DNA fragment was purified using QIAquick PCR Purification Kit (QIAGEN) following the instructions included in the kit. The purified DNA was precipitated with ethanol and then dissolved in 50 μL of a solution containing 10 mmol/L Tris-HCl (pH 7.4), 1 mmol/L EDTA. The resulting PCR reaction mixture was subcloned into the HEF expression vector HEF-VL-gκ1 (WO92/19759) prepared by digestion with BamHI and HindIII, and the nucleotide sequence was determined. A plasmid containing a DNA fragment having the amino acid sequence of the correct L chain V region was designated HEF-huM2L1.1#3. The amino acid sequence and nucleotide sequence of the L chain V region contained in this plasmid HEF-huM2L1.1#3 are shown in SEQ ID NO: 37.

Humanized MABL-2 antibody L chain V region versions 1.2, 1.3, 1.4, 1.5 were prepared as follows.

Version 1.2 was prepared by amplifying the plasmid HEF-huM2L1.1#3 as template DNA by PCR using HuMLbS (SEQ ID NO: 38) and HuMLbAS (SEQ ID NO: 39) designed to change arginine at position 51 to leucine as mutagenic primers, thereby giving a plasmid HEF-huM2L1.2#1. The amino acid sequence and nucleotide sequence of the L chain V region contained in this plasmid HEF-huM2L1.2#1 are shown in SEQ ID NO: 40.

Version 1.3 was prepared by amplifying the plasmid HEF-huM2L1.1#3 as template DNA by PCR using HuMLcS (SEQ ID NO: 41) and HuMLcAS (SEQ ID NO: 42) designed to change tyrosine at position 92 to phenylalanine as mutagenic primers, thereby giving a plasmid HEF-huM2L1.3#1. The amino acid sequence and nucleotide sequence of the L chain V region contained in this plasmid HEF-huM2L1.3#1 are shown in SEQ ID NO: 43.

Version 1.4 was prepared by amplifying the plasmid HEF-huM2L1.1#3 as template DNA by PCR using HuMLdS (SEQ ID NO: 44) and HuMLdAS (SEQ ID NO: 45) designed to change phenylalanine at position 41 to tyrosine as mutagenic primers, thereby giving a plasmid HEF-huM2L1.4#1. The amino acid sequence and nucleotide sequence of the L chain V region contained in this plasmid HEF-huM2L1.4#1 are shown in SEQ ID NO: 46.

Version 1.5 was prepared by amplifying the plasmid HEF-huM2L1.1#3 as template DNA by PCR using HuMLeS (SEQ ID NO: 47) and HuMLeAS (SEQ ID NO: 48) designed to change glutamine at position 42 to leucine as mutagenic primers, thereby giving a plasmid HEF-huM2L1.5#1. The amino acid sequence and nucleotide sequence of the L chain V region contained in this plasmid HEF-huM2L1.5#1 are shown in SEQ ID NO: 49.

(ii) Secondary Design

Considering the conservation of the sequence WYLQ-PGQSP-LIY [SEQ ID NO:122] of FR2, homology searches were performed again for the humanized MABL-2 antibody L chains. As a result, the human antibody 1802359A showing the highest homology (Pascual V. et al., J. Immunol., 146(12), 4385-4391, 1991) was selected to use the FRs therefrom. In humanized huM2 antibody L chain version "2.1", FR1-FR4 were identical with FR1-FR4 of the human antibody 1802359A, and the CDRs were identical with the CDRs in the L chain V region of the mouse MABL-2 antibody. For lack of information of the leader sequence of 1802359A, the leader sequence of the human antibody HSJC11VJ used in the primary design was used.

Humanized MABL-2 antibody L chain version "2.1" was prepared using version 2.0 obtained by replacing only FR2 of version "1.1" by FR2 of the human antibody 1802359A as template DNA.

First, version 2.0 was prepared by amplifying the plasmid HEF-huM2L1.1#3 as template DNA by PCR using HuMLfS (SEQ ID NO: 50) and HuMLfAS (SEQ ID NO: 51) designed to change FR2 of humanized MABL-2 antibody L chain version "1.1" to FR2 of the human antibody 1802359A as mutagenic primers, thereby giving a plasmid HEF-huM2L2.0#1. The amino acid sequence and nucleotide sequence of the L chain V region contained in this plasmid HEF-huM2L2.0#1 are shown in SEQ ID NO: 52.

Then, humanized MABL-2 antibody L chain version "2.1" was prepared by CDR grafting using PCR. For preparing the humanized MABL-2 antibody L chain (version "2.1"), six synthetic oligo DNAs (PCR primers) were used. Among the synthetic oligo DNAs, HuMLS (SEQ ID NO: 35), HuMLgS0 (SEQ ID NO: 53), and HuMLgS (SEQ ID NO: 54) have sense DNA sequences, while HuMLAS (SEQ ID NO: 36), HuM-LgAS0 (SEQ ID NO: 55), and HuMLgAS (SEQ ID NO: 56) have antisense DNA sequences.

In the first PCR, HEF-huM2L2.0#1 was used as template DNA together with the following PCR primer sets. PCR was performed using HuMLS/HuMLgAS0, HuMLgS0/HuML-gAS, and HuMLgS/HuMLAS, and the PCR products were purified. The products huM2L2.1-1, huM2L2.1-2, and huM2L2.1-3 were assembled by their own complementarity, and PCR primers HuMLS and HuMLAS were added to amplify the full-length DNA encoding the humanized MABL-2 antibody L chain (version "2.1") (second PCR).

The first PCR was performed using 50 μL of a reaction mixture containing 20 pmol each of the PCR primers, 0.2 mmol/L dNTP, 1 mmol/L MgSO$_4$, 5 ng of the template DNA and 1 U KOD -Plus- in the supplied buffer for 35 cycles of 94° C. for 15 seconds, 50° C. for 30 seconds, and 68° C. for 1 minute, followed by incubation at 68° C. for 7 minutes. The PCR products were purified using QIAquick PCR Purification Kit (QIAGEN) following the instructions included in the kit to give pure DNA fragments. In the second PCR, 100 µL of a reaction mixture containing 1 µL each of the first PCR products and 2 U KOD -Plus- was incubated for 5 cycles of 94° C. for 15 seconds, 50° C. for 30 seconds, and 68° C. for 1 minute, followed by incubation at 68° C. for 5 minutes, and then 40 pmol each of the PCR primers were added. Subsequently, 35 rounds of PCR were performed under the same conditions as those of the first PCR, and the PCR product (426 bp) was separated by electrophoresis on a 1.2% agarose gel and purified.

The purified DNA was subcloned into the HEF expression vector HEF-VL-gκ1 prepared by digestion with BamHI and HindIII, and the nucleotide sequence was determined. A plasmid containing a DNA fragment having the amino acid sequence of the correct L chain V region was designated HEF-huM2L2.1#1. The amino acid sequence and nucleotide sequence of the L chain V region contained in this plasmid HEF-huM2L2.1#1 are shown in SEQ ID NO: 57.

(3) Transfection into COS-7 Cells

In order to evaluate the antigen-binding activity of each chain of the humanized antibody, the expression plasmids described above and a chimeric MABL-2 antibody as a positive control were transiently expressed in COS-7 cells. Specifically, a combination of each of the humanized MABL-2 antibody H chain expression vectors (HEF-huM2H1.1#1, HEF-huM2H1.2#1, HEF-huM2H1.3#2, HEF-huM2H1.4#1, HEF-huM2H1.5#1, HEF-huM2H2.1#3) and a chimeric L chain expression vector HEF-M2L3 (WO00/53634) for transient expression of the H chains and a combination of each of the humanized MABL-2 antibody L chain expression vectors (HEF-huM2L1.1#3, HEF-huM2L1.2#1, HEF-huM2L1.3#1, HEF-huM2L1.4#1, HEF-huM2L1.5#1, HEF-huM2L2.1#1) and a chimeric H chain HEF-M2H3 (WO00/53634) for transient expression of the L chains were cotransduced into COS-7 cells using Fugene 6 Transfection Reagent (Roche Diagnostics). In 2 mL of DMEM medium (GIBCO) containing 10% fetal calf serum (GIBCO) were cultured $1.5 \times 10^5$ cells overnight. A total volume of 100 µL of DMEM medium containing 2 µg of each plasmid and 6 µL of Fugene 6 Transfection Reagent was reacted for 1 hour at room temperature and added to the cultures. After incubation at 37° C. under 5% $CO_2$ overnight, the medium was exchanged for 2 mL of CHO-S-SFMII medium (GIBCO) containing 1% HT supplement (GIBCO). After incubation at 37° C. under 5% $CO_2$ for 72 hours, the culture supernatants were collected and used as samples for ELISA after removal of cell debris by centrifugation.

For transient expression of the chimeric MABL-2 antibody, the chimeric H chain HEF-M2H3 and chimeric L chain HEF-M2L3 were transfected into COS-7 cells in the same manner as described above, and the resulting culture supernatants were assayed by ELISA.

In order to evaluate the humanized MABL-2 antibody, a combination of humanized huM2 antibody H chain expression vector HEF-huM2H2.1#3 and humanized MABL-2 antibody L chain expression vector HEF-huM2L 2.1#1 was transfected into COS-7 cells in the same manner as described above, and the resulting culture supernatants were assayed by ELISA.

(4) Determination of Antibody Concentrations

The concentrations of the antibodies obtained were determined by ELISA. In the wells of 96-well plates for ELISA (Maxsorp, NUNC) was immobilized 100 µL of mouse anti-human Kappa Light Chain (Zymed) prepared at a concentration of 2 µg/mL in an immobilizing buffer (0.1 mol/L $NaHCO_3$, 0.02% $NaN_3$), and the plates were blocked with 300 µL of a diluting buffer (50 mmol/L Tris-HCl, 1 mmol/L $MgCl_2$, 0.15 mol/L NaCl, 0.05% Tween 20, 0.02% $NaN_3$, 1% bovine serum albumin (BSA), pH 8.1), and then 100 µL/well of serial dilutions of the culture supernatants of COS-7 cells in which the chimeric antibody or humanized antibody had been expressed were added to the wells. After incubation for 1 hour at room temperature and washing, 100 µL of alkaline phosphatase-labeled goat anti-human IgG antibody (Zymed) was added. After incubation at room temperature and washing, 1 mg/mL of a substrate solution (Sigma 104, p-nitrophenyl phosphate, SIGMA) was added and then the absorbance at 405 nm was measured using a microplate reader (Bio-Rad). As a standard for concentration determination, human IgG1, kappa (SIGMA) was used.

(5) Determination of Activities of the Humanized Antibody

The humanized antibody was evaluated for antigen-binding activity and binding inhibitory activity as follows.

(i) Determination of Antigen-Binding Activity

ELISA plates for the determination of antigen-binding activity were prepared as follows. In the wells of 96-well plates for ELISA was immobilized 100 µL of an anti-FLAG antibody (SIGMA) prepared at a concentration of 3 µg/mL in an immobilizing buffer. The plates were blocked with 300 µL of a diluting buffer and then incubated at room temperature for 1 hour with 100 µL of FLAG-labeled soluble human CD47 (WO00/53634) prepared at a concentration of 1 µg/mL. After washing, serial dilutions of the culture supernatants of COS-7 cells in which the chimeric antibody or humanized antibody had been expressed were added to the wells. After incubation at room temperature and washing, 100 µL of alkaline phosphatase-labeled goat anti-human IgG antibody (Zymed) was added. After incubation at room temperature and washing, 1 mg/mL of a substrate solution (Sigma 104, p-nitrophenyl phosphate, SIGMA) was added and then the absorbance at 405 nm was measured using a microplate reader (Bio-Rad).

(ii) Determination of Binding Inhibitory Activity

Plates for the determination of binding inhibitory activity were prepared as follows. In the wells of 96-well plates for ELISA was immobilized 100 µL of an anti-FLAG antibody (SIGMA) prepared at a concentration of 3 µg/mL in an immobilizing buffer, in the same manner as described for antigen-binding activity. The plates were blocked with 300 µL of a diluting buffer and then incubated at room temperature for 1 hour with 100 µL of FLAG-labeled soluble human CD47 (WO00/53634) prepared at a concentration of 1 µg/mL. After washing, 100 µL of a 1:1 mixture of each of serial dilutions of the culture supernatants of COS-7 cells in which the chimeric antibody or humanized antibody had been expressed and 0.6 µg/mL of biotin-labeled MABL-2. After incubation at room temperature and washing, 100 µL of alkaline phosphatase-labeled streptavidin (Zymed) was added. After incubation at room temperature and washing, 1 mg/mL of a substrate solution (Sigma 104, p-nitrophenyl phosphate, SIGMA) was added and then the absorbance at 405 nm was measured using a microplate reader (Bio-Rad).

(6) Evaluation of Activities (i) Evaluation of Humanized H Chains

Figure 2:
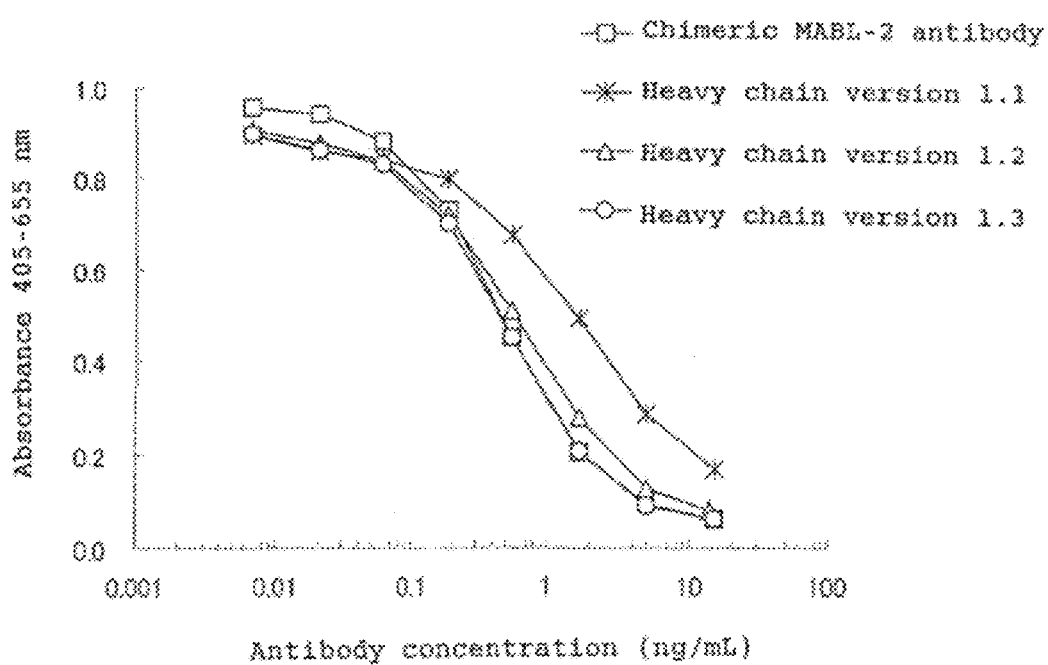
FIG. 2 is a graph showing that versions 1.2 and 1.3 among the antibodies combining humanized H chain versions 1.1, 1.2 and 1.3 with a chimeric L chain have binding inhibitory activities by MABL-2 nearly comparable to that of the chimeric antibody.

The antibodies combining humanized H chain versions 1.1, 1.2 and 1.3 with a chimeric L chain showed human CD47-binding activities comparable to that of the chimeric antibody (FIG. 1). However, version 1.1 showed a weaker binding inhibitory activity by MABL-2 than those of versions 1.2 and 1.3. Version 1.3 had an inhibitory activity nearly comparable to that of the chimeric antibody and showed an inhibitory activity comparable to or slightly higher than that of version 1.2 (FIG. 2). This result shows that the conservation of the amino acid residue at position 72 is important and that the amino acid residue at position 30 may be changed to threonine (version 1.3).

Figure 3:
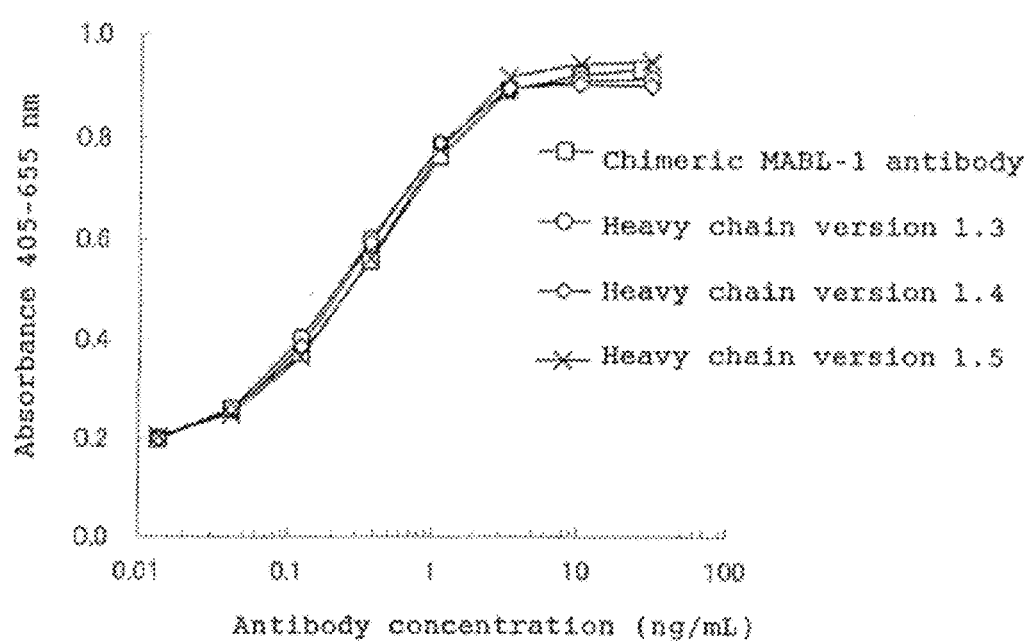
FIG. 3 is a graph showing that the antibodies combining humanized H chain versions 1.4 and 1.5 with a chimeric L chain have binding activities comparable to those of the chimeric antibody and version 1.3.
Figure 4:
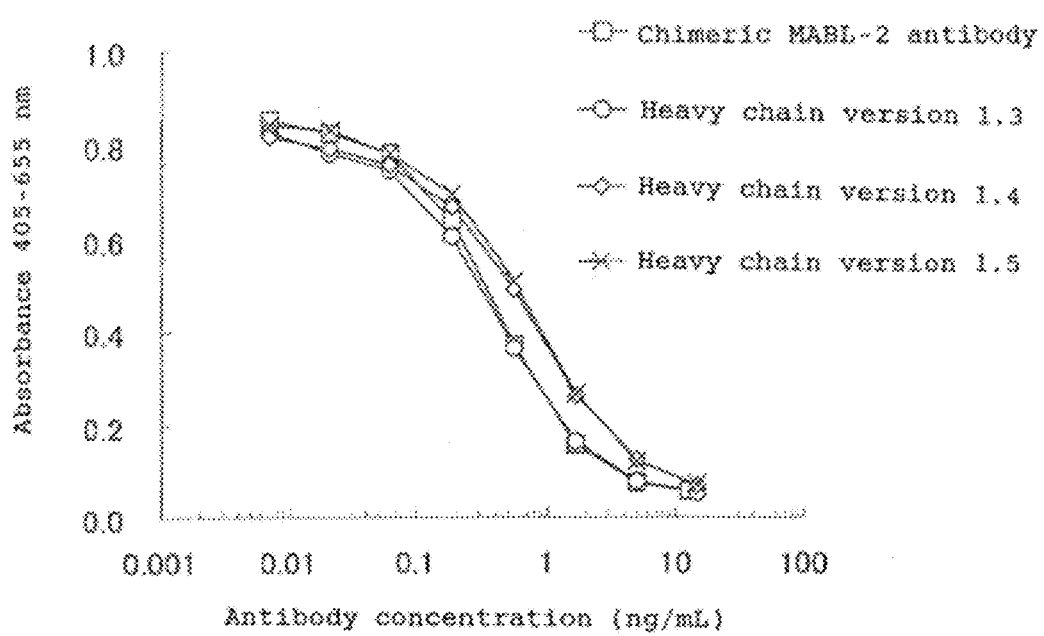
FIG. 4 is a graph showing that the antibodies combining humanized H chain versions 1.4 and 1.5 with a chimeric L chain have binding inhibitory activities weaker than those of the chimeric antibody and version 1.3.

In expectation of further increase in activities, H chain versions 1.4 and 1.5 were newly prepared. The antibodies combining H chain versions 1.4 and 1.5 with a chimeric L chain showed binding activities comparable to those of the chimeric antibody and version 1.3 (FIG. 3) and lower inhibitory activities (FIG. 4). This result suggests that the amino acid residues at positions 67 and 70 should be conserved.

Figure 5:
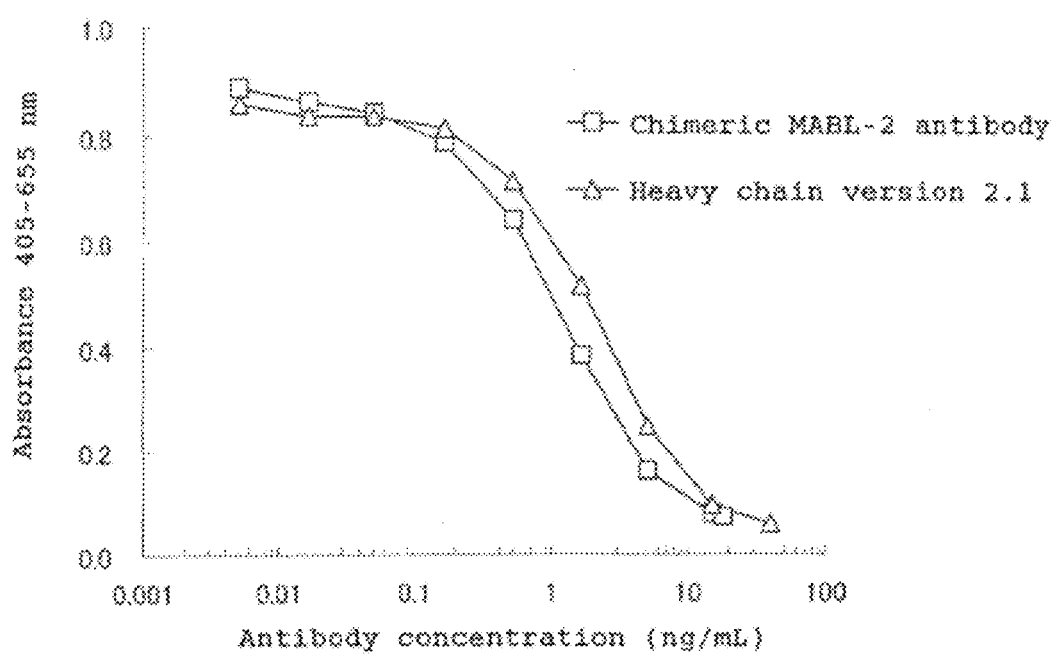
FIG. 5 is a graph showing that humanized H chain version 2.1 has a binding inhibitory activity by MABL-2 nearly comparable to that of the chimeric antibody.

Based on the results of versions 1.1-1.5, a secondary design was performed to prepare version 2.1. Version 2.1 showed a binding inhibitory activity by MABL-2 comparable to that of the chimeric antibody (FIG. 5). This result suggests that version 2.1 suffices as a humanized H chain.

(ii) Evaluation of Humanized L Chains

Figure 6:
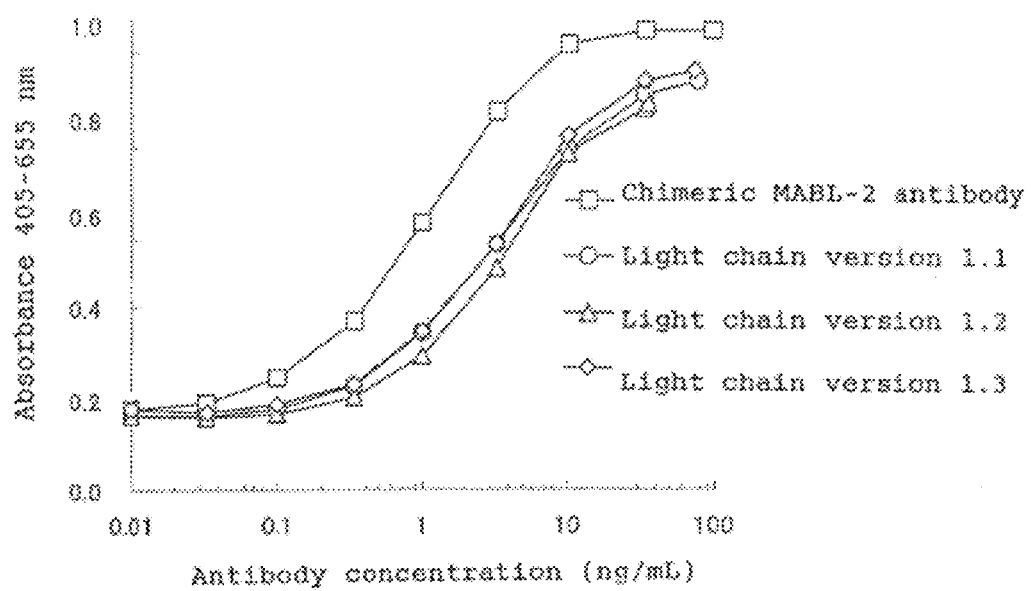
FIG. 6 is a graph showing that all of the three antibodies combining humanized L chain version 1.1, 1.2 and 1.3 with a chimeric H chain have binding activities to human IAP weaker than that of the chimeric antibody.
Figure 7:
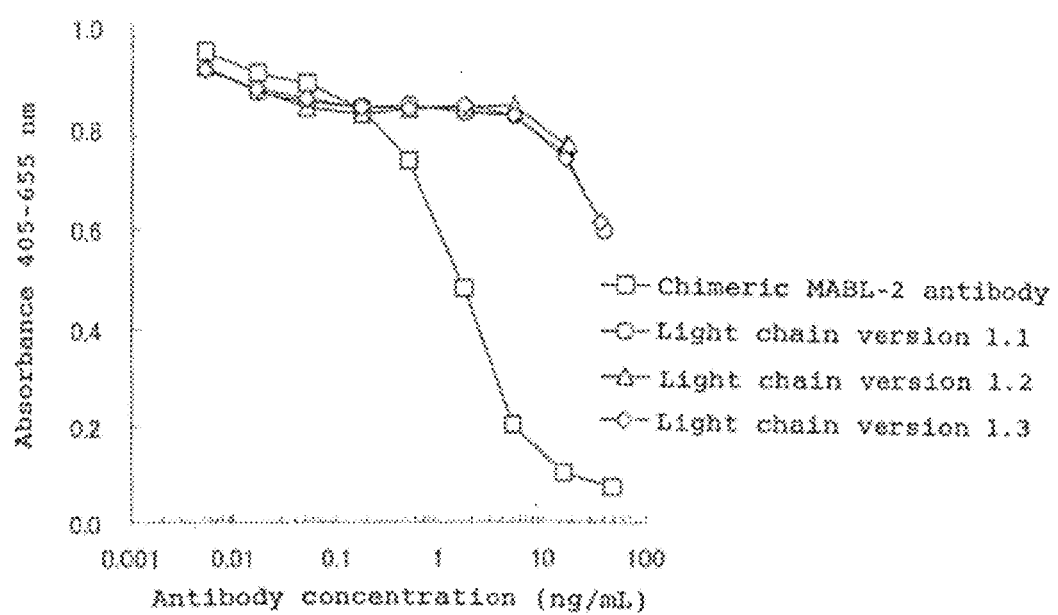
FIG. 7 is a graph showing that all of the antibodies combining humanized L chain version 1.1, 1.2 and 1.3 with a chimeric H chain have binding inhibitory activities by MABL-2 weaker than that of the chimeric antibody.

All of the three antibodies combining humanized L chain versions 1.1, 1.2 and 1.3 with a chimeric H chain showed nearly comparable human CD47-binding activities, but lower than that of the chimeric antibody (FIG. 6). Moreover, all of the three antibodies showed a weaker binding inhibitory activity by MABL-2 than that of the chimeric antibody (FIG. 7). This result suggests that the amino acid residues at positions 51 and 92 are not especially important and may be replaced by other amino acid residues.

Figure 8:
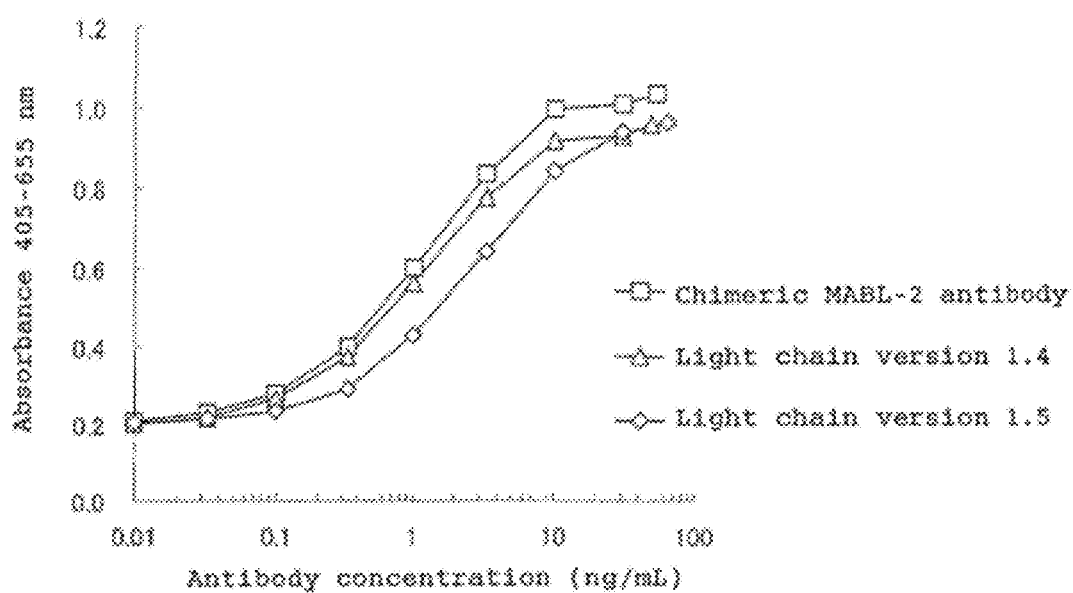
FIG. 8 is a graph showing that version 1.4 of the antibodies combining humanized L chain version 1.4 and 1.5 with a chimeric H chain has a binding activity comparable to that of the chimeric antibody.
Figure 9:
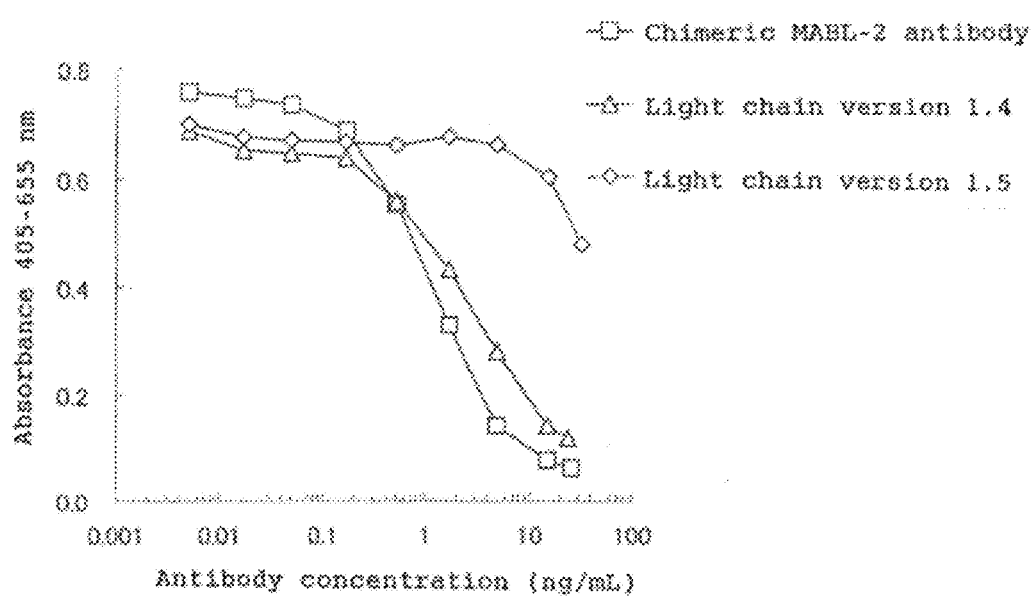
FIG. 9 is a graph showing that version 1.4 of the antibodies combining humanized L chain version 1.4 and 1.5 with a chimeric H chain also has a binding inhibitory activity approaching that of the chimeric antibody.

Amino acids of FR2 in proximity to the CDRs were examined because FR2 of the L chain forms an interface with the H chain (Chothia C. et al., J. Mol. Biol. 186, 651-663, 1985). Version 1.4 showed a binding activity nearly similar to that of the chimeric antibody. The binding activity of version 1.5 was lower than that of version 1.4, but higher than that of version 1.1 (FIG. 8). Version 1.4 also greatly improved in binding inhibitory activity over version 1.1, and approached the chimeric antibody in inhibitory activity (FIG. 9). The inhibitory activity of version 1.5 is visibly lower than that of the chimeric antibody, but slightly improved over version 1.1 (FIG. 9). This result suggests again that FR2 is important and especially, amino acid residues near positions 41 and 42 are essential for the improvement in activity.

Figure 10:
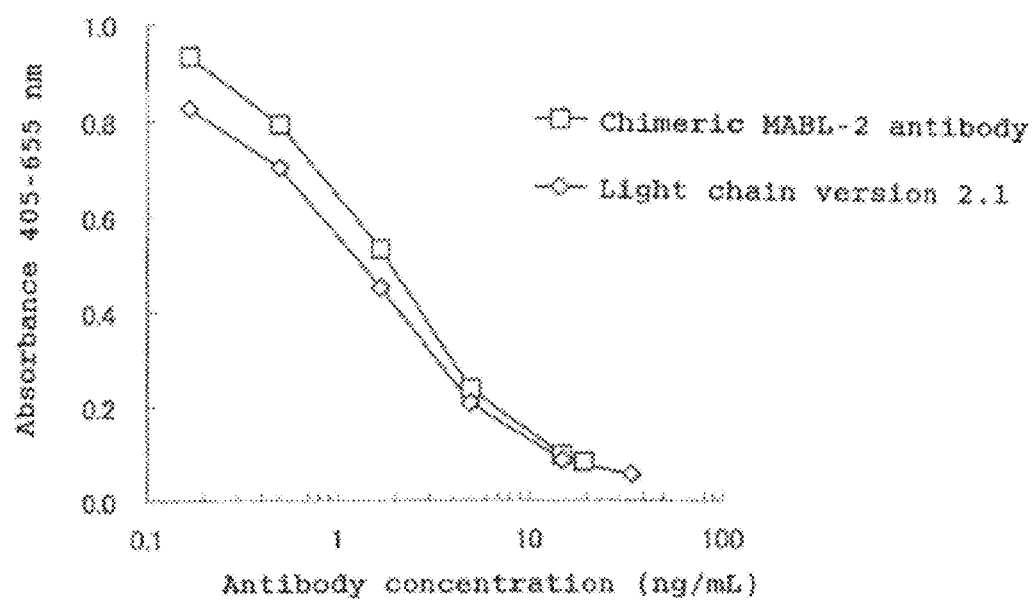
FIG. 10 is a graph showing that the antibody combining humanized L chain version 2.1 with a chimeric H chain has a binding inhibitory activity by MABL-2 comparable to that of the chimeric antibody.

Based on the results of versions 1.1-1.5, a secondary design was performed to prepare version 2.1. The antibody combining humanized L chain version 2.1 and the chimeric H chain showed a binding inhibitory activity by MABL-2 comparable to that of the chimeric antibody (FIG. 10). This result suggests that version 2.1 suffices as a humanized L chain.

(iii) Evaluation of the Humanized MABL-2 Antibody

Figure 11:
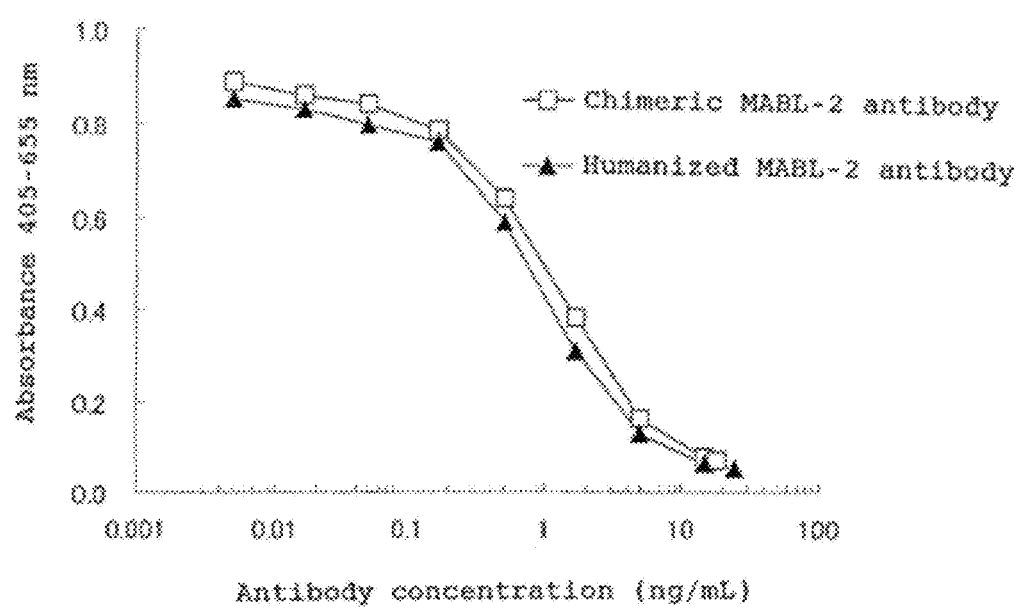
FIG. 11 is a graph showing that the humanized MABL-2 antibody combining humanized H chain version 2.1 with humanized L chain version 2.1 has a binding inhibitory activity by MABL-2 comparable to that of the chimeric antibody.

The antibody combining humanized H chain version 2.1 and humanized L chain version 2.1 showed a binding inhibitory activity by MABL-2, i.e., affinity for hCD47 comparable to or higher than that of the chimeric antibody (FIG. 11). Thus, a humanized MABL-2 antibody having the sequences of the FRs of a single natural human antibody in both H chain and L chain was successfully constructed.

Example 2

Construction of a Humanized MABL-1 Antibody

A mouse MABL-1 antibody (WO00/53634) was also humanized. The amino acid sequences of the CDRs in the mouse MABL-1 antibody and the mouse MABL-2 antibody differ by only 3 residues in the H chain and 4 residues in the L chain. Thus, we decided to construct a humanized antibody of the mouse MABL-1 antibody on the basis of the secondary design from the mouse MABL-2 antibody shown in Example 1 (huM2H version 2.1, huM2L version 2.1).

(1) Construction of a Humanized MABL-1 Antibody H Chain

For preparing humanized MABL-1 antibody H chain version "2.1", eight synthetic oligo DNAs were used. Among the synthetic oligo DNAs, HuMHS (SEQ ID NO: 5), M1CH1MS (SEQ ID NO: 58), M1CH2GS (SEQ ID NO: 59), and M1CH3SS (SEQ ID NO: 60) have sense DNA sequences, while M1CH1MAS (SEQ ID NO: 61), M1CH2GAS (SEQ ID NO: 62), M1CH3SAS (SEQ ID NO: 63), and HuMHAS (SEQ ID NO: 6) have antisense DNA sequences.

In the first PCR, HEF-huM2H2.1#3 was used as template DNA together with the following PCR primer sets. Four reactions HuMHS/M1CH1MAS, M1CH1MS/M1CH2GAS, M1CH2GS/M1CH3SAS, and M1CH3SS/HuMHAS were performed, and the PCR products were purified. The products were assembled by their own complementarity and PCR primers HuMHS and HuMHAS were added to amplify the full-length DNA encoding humanized MABL-1 antibody H chain version "2.1" (second PCR). In the same way as in Example 1, the DNA was subcloned into the HEF expression vector HEF-VL-gg1, and the nucleotide sequence was determined. A plasmid containing a DNA fragment having the amino acid sequence of the correct H chain V region was designated HEF-huM1H2.1#1. The amino acid sequence and nucleotide sequence of the H chain V region contained in this plasmid HEF-huM1H2.1#1 are shown in SEQ ID NO: 64.

(2) Construction of a Humanized MABL-1 Antibody L chain

For preparing humanized MABL-1 antibody L chain version "2.1", four synthetic oligo DNAs were used. Among the synthetic oligo DNAs, HuMLS (SEQ ID NO: 5) and M1CL1aS (SEQ ID NO: 65) have sense DNA sequences, while M1CL1aAS (SEQ ID NO: 66) and HuMLAS (SEQ ID NO: 6) have antisense DNA sequences.

In the first PCR, HEF-huM2L2.1#1 was used as template DNA together with the following PCR primer sets. PCR was performed using HuMHS/M1CL1aAS and M1CL1aS/HuMLAS, and the PCR products were purified. The products were assembled by their own complementarity and PCR primers HuMLS and HuMLAS were added to amplify the full-length DNA encoding humanized MABL-1 antibody L chain version "2.1" (second PCR). In the same way as in Example 1, the DNA was subcloned into the HEF expression vector HEF-VL-gκ1, and the nucleotide sequence was determined. A plasmid containing a DNA fragment having the amino acid sequence of the correct L chain V region was designated HEF-huM1L2.1#1. The amino acid sequence and nucleotide sequence of the L chain V region contained in this plasmid HEF-huM1L2.1#1 are shown in SEQ ID NO: 67.

(3) Expression of a Humanized MABL-1 Antibody

The humanized MABL-1 antibody H chain expression vector HEF-huM1L2.1#1 and humanized MABL-1 antibody L chain expression vector HEF-huM1L2.1#1 were used to prepare a humanized MABL-1 antibody according to the transfection method into COS-7 cells described above. The determination of antibody concentrations and the determination of activities of the antibody were also performed by the methods shown in Example 1.

(4) Evaluation of Activities of the Humanized MABL-1 Antibody

Figure 12:
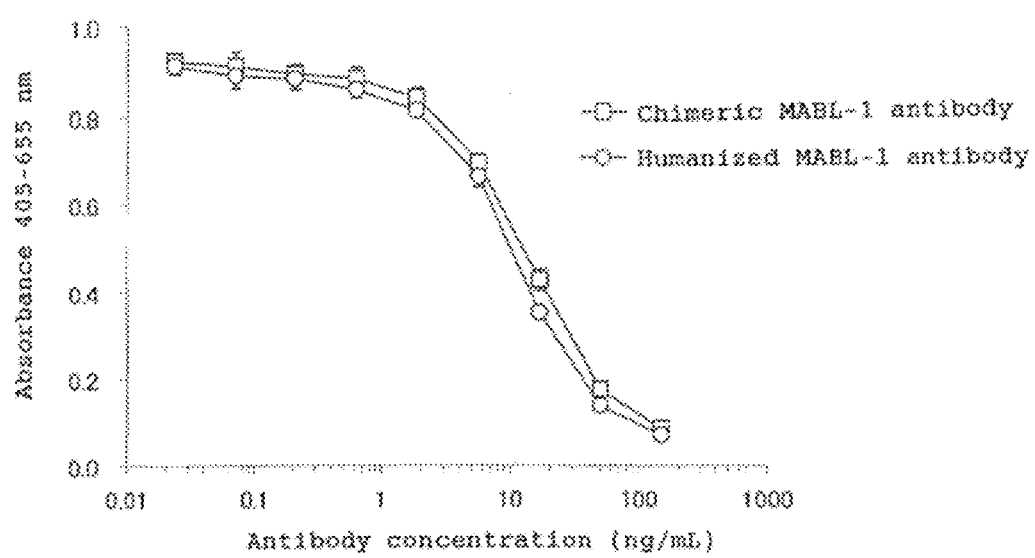
FIG. 12 is a graph showing that the humanized MABL-1 antibody combining humanized H chain version 2.1 with humanized L chain version 2.1 has a binding inhibitory activity by MABL-1 comparable to that of the chimeric antibody.

The antibody combining humanized H chain version 2.1 and humanized L chain version 2.1 showed a binding inhibitory activity by MABL-1, i.e., affinity for hCD47 comparable to or higher than that of the chimeric antibody (FIG. 12). Thus, a humanized MABL-1 antibody having the sequences of FRs of a single natural human antibody in both H chain and L chain was successfully constructed.

Example 3

Apoptosis-inducing Effects of the Humanized MABL-1 and MABL-2 Antibodies

Figure 13:
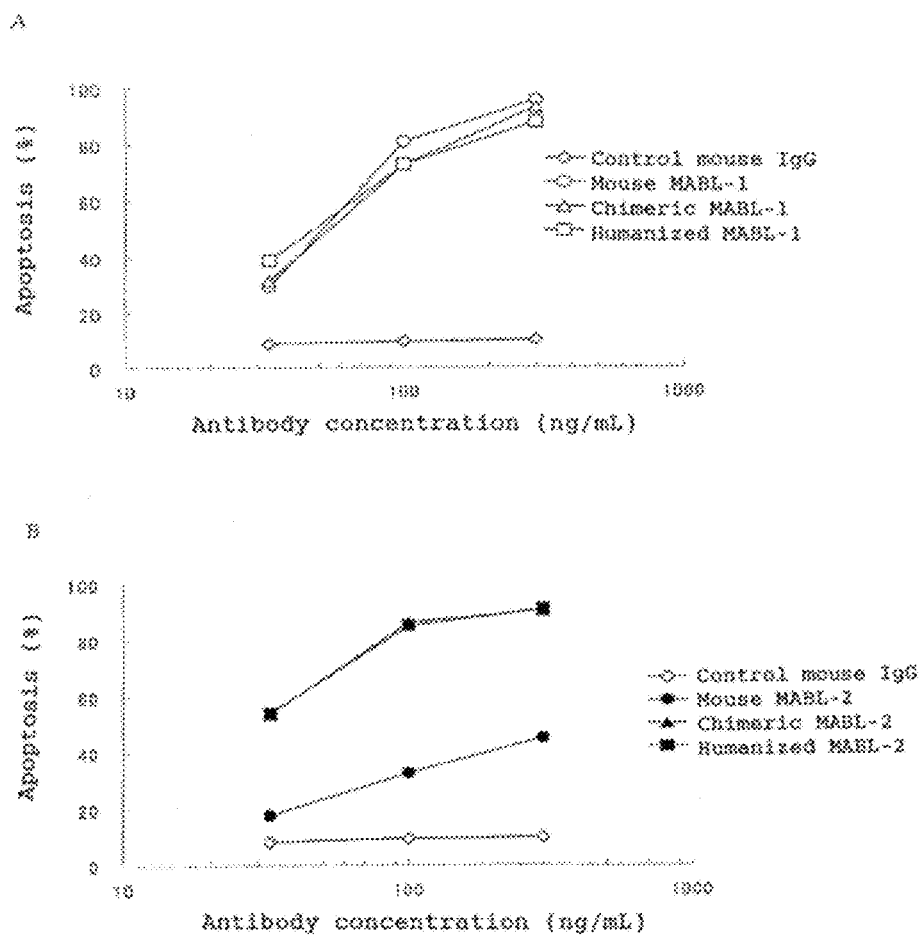
FIGS. 13A and 13B are graphs showing that the humanized MABL-1 antibody and the humanized MABL-2 antibody induce cell death in L1210 cells containing the human IAP gene, respectively.

L1210 cells containing the human CD47 gene were used to evaluate the apoptosis-inducing effects of humanized MABL-1 and MABL-2 antibodies by Annexin-V staining (Roche Diagnostics). The culture supernatants of COS-7 cells expressing each of the humanized antibodies were added at antibody concentrations of 300 ng/mL, 100 ng/mL, and 33.3 ng/mL to $1 \times 10^5$ cells, and incubated for 24 hours. Then, Annexin-V staining was performed, and fluorescence intensity was determined by FACScan system (BECTON DICKINSON). As a result, significant cell death was induced in L1210 cells containing the human CD47 gene (FIG. 13).

Example 4

Preparation of Single Chain Fvs from the Humanized MABL-1 and MABL-2 Antibodies (1) Preparation of a Humanized MABL-2 Antibody Single-Chain Fv (HL5)

A humanized MABL-2 antibody single-chain Fv (HL5) consisting of variable regions joined by a 5 mer peptide linker in the order of [H chain]-[L chain] from the N-terminus was prepared as follows. The humanized MABL-2 antibody HL5 was prepared by amplifying the humanized MABL-2 antibody H chain V region and humanized MABL-2 antibody L chain V region by PCR and joining them. For preparing the humanized MABL-2 antibody HL5, four PCR primers (A-D) were used. Primers A and C have sense sequences, while primers B and D have antisense sequences.

The forward primer Sal-huHS (primer A, SEQ ID NO: 68) for the H chain V region was designed to hybridize to the DNA encoding the N-terminus of the H chain V region and to have an SalI restriction endonuclease site. The reverse primer huMHAS-A (primer B, SEQ ID NO: 69) for the H chain V region was designed to hybridize to the DNA encoding the C-terminus of the H chain V region and to overlap the linker.

The forward primer X5-huLgS (primer C, SEQ ID NO: 70) for the L chain V region was designed to hybridize to the DNA encoding the C-terminus of the H chain V region, to contain the DNA sequence encoding the 5mer linker region consisting of Gly Gly Gly Gly Ser (SEQ ID NO: 109) and to overlap the DNA encoding the N-terminus of the L chain V region. The reverse primer NothuLAS (primer D, SEQ ID NO: 71) for the L chain V region was designed to hybridize to the DNA encoding the C-terminus of the L chain V region and to have two transcription termination codons and an NotI restriction endonuclease site.

In the first PCR, two reactions were performed using primer sets A/B and C/D, and the PCR products (huM2 Db-1 and huM2 Db-2) were purified. The two PCR products obtained from the first PCR were assembled by their own complementarity, and primers A and D were added to amplify the full-length DNA encoding the humanized MABL-2 antibody HL5 (second PCR). In the first PCR, the plasmid HEF-huM2H2.1#3 encoding the humanized MABL-2 antibody H chain V region (see Example 1) and the plasmid HEF-huM2L2.1#1 encoding the humanized MABL-2 antibody L chain V region (see Example 1) were used as templates.

The first PCR was performed using 50 μL of a reaction mixture containing 20 pmol each of the PCR primers, 0.2 mmol/L dNTP, 1 mmol/L MgSO$_4$, 5 ng of each template DNA and 1 U KOD -Plus- in the supplied buffer for 35 cycles of 94° C. for 15 seconds, 50° C. for 30 seconds, and 68° C. for 1 minute, followed by incubation at 68° C. for 7 minutes.

The PCR products A-B (huM2 Db-1) and C-D (huM2 Db-2) were separated by electrophoresis on a 1.2% agarose gel and purified, and assembled in second PCR. In the second PCR, 100 μL of a reaction mixture containing 1 μL of huM2 Db-1 and 1 μL of huM2 Db-2 as templates and 2 U KOD-Plus-was incubated for 5 cycles of 94° C. for 15 seconds, 50° C. for 30 seconds, and 68° C. for 1 minute, followed by incubation at 68° C. for 5 minutes, and then 40 pmol each of the PCR primers were added. Subsequently, 35 rounds of PCR were performed under the same conditions as those of the first PCR, and the PCR product was purified using QIAquick PCR Purification Kit (QIAGEN), and digested with SalI and NotI, and the resulting DNA fragment was cloned into the vector pCHO1-Igs (WO00/53634). This expression vector pCHO1-Igs contains a mouse IgG1 signal sequence suitable for mammal secretory cell expression systems (Nature, 332, 323-327, 1988). After DNA sequencing, a plasmid containing a DNA fragment encoding the correct amino acid sequence of the humanized MABL-2 antibody HL5 was designated pCHOhuM2 Db.

The nucleotide sequence and amino acid sequence of the humanized MABL-2 antibody HL5 contained in this plasmid pCHOhuM2 Db are shown in SEQ ID NOS: 73 and 110, respectively.

(2) Preparation of a Humanized MABL-1 Antibody Single-chain Fv (HL5)

A humanized MABL-1 antibody HL5 was prepared in the same manner as described for the preparation of the humanized MABL-2 antibody single-chain Fv (HL5) above. In the first PCR, the plasmid HEF-huM1H2.1#1 encoding the humanized MABL-1 antibody H chain V region (see Example 2) was used in place of HEF-huM2H2.1#3, and the plasmid HEF-huM1L2.1#1 encoding the humanized MABL-1 antibody L chain V region (see Example 2) was used in place of HEF-huM2L2.1#1 to give PCR products huM1 Db-1 and huM1 Db-2. The second PCR using them gave a plasmid pCHOhuM1 Db containing a DNA fragment encoding the correct amino acid sequence of the humanized MABL-1 antibody HL5. The nucleotide sequence and amino acid sequence of the humanized MABL-1 antibody HL5 contained in this plasmid pCHOhuM1 Db are shown in SEQ ID NOs: 74 and 111, respectively.

Example 5

Preparation of sc(Fv)$_2$ Containing Two H Chain V Regions and Two L Chain V Regions (1) Construction of a Humanized MABL-2 Antibody sc(Fv)$_2$ Expression Plasmid In order to prepare a plasmid expressing a humanized MABL-2 antibody sc(Fv)$_2$ consisting of variable regions joined by 5 mer, 15 mer and 5 mer peptide linkers in the order of [H chain]-[L chain]-[H chain]-[L chain] from the N-terminus, the PCR products described above huM2 Db-1 and huM2 Db-2 were further modified by PCR as shown below, and the resulting DNA fragment was introduced into the pCHO1-Igs vector.

For preparing the humanized MABL-2 antibody sc(Fv)$_2$, two PCR primers E, F were used in addition to the PCR primers A-D described above. Primer E has a sense sequence, while primer F has an antisense sequence.

The forward primer X15huHS (primer E, SEQ ID NO: 75) for the H chain V region was designed to overlap a part of the 15mer linker described below and to hybridize to the DNA encoding the N-terminus of the H chain V region. The reverse primer X15huLAS (primer F, SEQ ID NO: 76) for the L chain V region was designed to hybridize to the DNA encoding the C-terminus of the L chain V region and to hybridize to the DNA sequence encoding the 15mer linker region consisting of Gly Gly Gly Gly Ser Gly Gly Gly Gly Ser Gly Gly Gly Gly Ser (SEQ ID NO: 111).

In the first PCR, two reactions were performed using C/F and E/B primer sets, and the PCR products (huM2 Db-3 and huM2 Db-4) were purified. In the first PCR, the PCR product huM2 Db-2 encoding the humanized MABL-2 antibody L chain V region (see Example 4) and the PCR product huM2 Db-1 encoding the humanized MABL-2 antibody H chain V region (see Example 4) were used as templates. In the second PCR, a set of huM2 Db-1 and huM2 Db-3 and a set of huM2 Db-2 and huM2 Db-4 were assembled by their own complementarity. Then, primers A and F, and E and D were added to the respective sets to amplify two fragment DNAs (huM2 Db-13 and huM2 Db-24) encoding the humanized MABL-2 antibody sc(Fv)$_2$ (second PCR).

The first PCR was performed using 50 µL of a reaction mixture containing 20 pmol each of the PCR primers, 0.2 mmol/L dNTP, 1 mmol/L MgSO$_4$, 1 µL each of template DNAs and 1 U KOD -Plus- in the supplied buffer for 35 cycles of 94° C. for 15 seconds, 50° C. for 30 seconds, and 68° C. for 1 minute, followed by incubation at 68° C. for 7 minutes.

The PCR products C-F (huM2 Db-3) and E-B (huM2 Db-4) were separated by electrophoresis on a 1.2% agarose gel and purified, and used for assembling with huM2 Db-1 and huM2 Db-2 in the second PCR. In the second PCR, 100 µL of a reaction mixture containing 1 µL each of huM2 Db-1 and huM2 Db-3 or 1 µL each of huM2 Db-2 and huM2 Db-4 as templates and 2 U KOD-Plus-was incubated for 5 cycles of 94° C. for 15 seconds, 50° C. for 30 seconds, and 68° C. for 1 minute, followed by incubation at 68° C. for 5 minutes, and then 40 pmol each of the PCR primers were added. Subsequently, 35 rounds of PCR were performed under the same conditions as those of the first PCR, and the PCR products were purified using QIAquick PCR Purification Kit (QIAGEN), and huM2 Db-13 was digested with SalI and BamHI and huM2 Db-24 was digested with BamHI and NotI, and the resulting DNA fragments were cloned into the pCHO1-Igs vector. After DNA sequencing, a plasmid containing a DNA fragment encoding the correct amino acid sequence of the humanized MABL-2 antibody sc(Fv)$_2$ was designated pCHOhuM2scDb. The nucleotide sequence and amino acid sequence of the humanized MABL-2 antibody sc(Fv)$_2$ contained in this plasmid pCHOhuM2scDb are shown in SEQ ID NOs: 78 and 113, respectively.

(3) Construction of a Humanized MABL-1 Antibody sc(Fv)$_2$ Expression Plasmid

In order to prepare a plasmid expressing a humanized MABL-1 antibody sc(Fv)$_2$ consisting of variable regions joined by 5 mer, 15 mer and 5 mer peptide linkers in the order of [H chain]-[L chain]-[H chain]-[L chain] from the N-terminus, the procedure described above for the construction of the humanized MABL-2 antibody sc(Fv)2 expression plasmid was followed.

In the first PCR, the PCR product huM1 Db-2 encoding the humanized MABL-1 antibody L chain V region was used in place of the PCR product huM2 Db-2, and the PCR product huM1 Db-1 encoding the humanized MABL-1 antibody H chain V region was used in place of the PCR product huM2 Db-1 to give a plasmid pCHOhuM1scDb containing a DNA fragment encoding the correct amino acid sequence of the humanized MABL-1 antibody sc(Fv)$_2$. The nucleotide sequence and amino acid sequence of the humanized MABL-1 antibody sc(Fv)2 contained in this plasmid pCHOhuM1scDb are shown in SEQ ID NOs: 79 and 114, respectively.

(4) Establishment of a Stable Producing CHO Cell Line

In order to establish a CHO cell line permanently expressing the MABL-2 antibody HL5 and sc(Fv)$_2$, and MABL-1 antibody HL5 and sc(Fv)$_2$, the vectors pCHOhuM1 Db, pCHOhuM1scDb, pCHOhuM2 Db and pCHOhuM2scDb were transferred into CHO cells.

Each vector was transformed into CHO cells by electroporation using Gene Pulser (BioRad). A mixture of DNA (10 µg) and 0.75 mL of CHO cells (1×10$^7$ cells/mL) suspended in PBS was added to a cuvette, and pulsed at 1.5 kV, 25 µF. After a recovery period of 10 minutes at room temperature, electroporated cells were added to a nucleic acid-containing α-MEM medium (GIBCO BRL) containing 10% fetal calf serum and cultured. After overnight incubation, the culture supernatants were removed and the cells were rinsed with PBS and then incubated with a nucleic acid-free α-MEM medium (GIBCO BRL) containing 10% fetal calf serum. The binding target soluble human CD47 was immobilized on a BIACORE sensor chip CM5 (Biacore AB) by amine coupling, and the culture supernatants recovered from clones obtained by selective culture were injected into this sensor chip. The expression levels were assayed from the bound amount, and highly expressing clones were selected as cell lines producing the HL5 and sc(Fv)$_2$ from the humanized MABL-1 and -2 antibody. After culture in a cell-free medium CHO-S-SFM II (GIBCO BRL) containing 10 nM methotrexate (SIGMA), the culture supernatants were collected and cell debris were removed by centrifugation to give recovered culture supernatants.

(5) Purification of the HL5 and sc(Fv)$_2$ of the Humanized MABL-1 and Humanized MABL-2

The HL5 and sc(Fv)$_2$ of the humanized MABL-1 and humanized MABL-2 (a total of 4 antibodies) were purified from the culture supernatants obtained in (4) above by three steps consisting of ion exchange chromatography, hydroxyapatite chromatography, and gel filtration chromatography. All of the four antibodies were purified by exactly the same procedure. There was practically no difference in purification results between the humanized MABL-1 and the humanized MABL-2 and between the HL5 and the sc(Fv)$_2$. For this reason, the purification procedure is described generically. Only examples of the purification results of the humanized MABL-1 antibody HL5 are shown in the figures.

Figure 14:
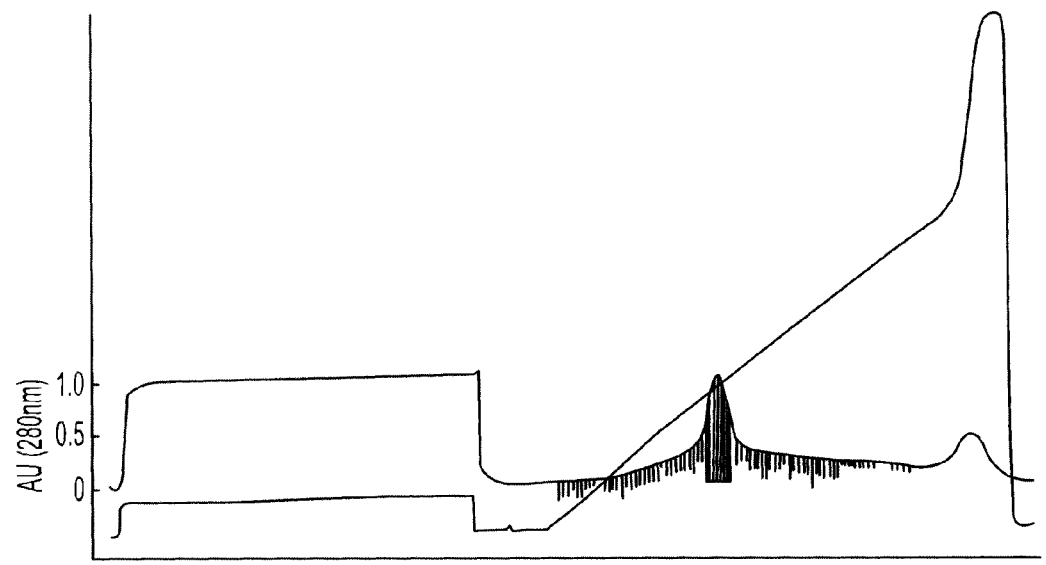
FIG. 14 is a chromatogram of the culture supernatants of humanized MABL-1 antibody HL5-producing CHO cells purified on an SP-Sepharose F.F. column. The hatched area shows a purified fraction used in the subsequent step.

The culture supernatants were diluted with the same volume of 20 mM sodium acetate buffer, pH 5.5 containing 0.02% Tween 20, and then adjusted to pH 5.5 with 1 M acetic acid. Then, the solutions were applied to SP Sepharose Fast Flow columns (Amersham Bioscience) equilibrated with 20 mM sodium acetate buffer, pH 5.5 containing 0.02% Tween 20, and the columns were washed with the same buffer and then polypeptides adsorbed to the columns were eluted with a linear concentration gradient of 0 M to 0.6 M NaCl in the same buffer. Thus obtained fractions were analyzed by SDS-PAGE, and fractions containing the HL5 and sc(Fv)$_2$ were collected (FIG. 14).

Figure 15:
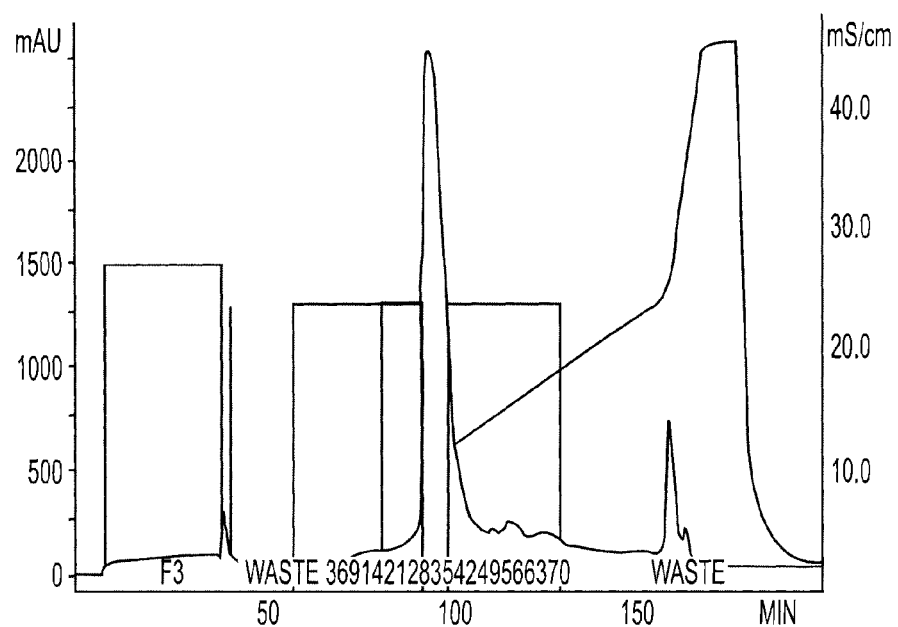
FIG. 15 is a chromatogram of a fraction obtained from the SP-Sepharose F.F. column and further purified on a Hydroxyapatite column in the purification process of the humanized MABL-1 antibody HL5. The hatched area shows a purified fraction used in the subsequent step.

The HL5 and sc(Fv)$_2$ fractions obtained in the first step were adjusted to a pH range of 6.0-6.5 with 0.1 M NaOH, and then applied to hydroxyapatite columns (BIO-RAD, type I, 20 mm) equilibrated with 10 mM phosphate buffer, pH 7.0 containing 0.02% Tween 20, and the columns were washed with the same buffer and then the phosphate buffer concentration was linearly increased to 200 mM to elute polypeptides adsorbed to the columns. Thus obtained fractions were analyzed by SDS-PAGE, and fractions containing a desired polypeptide were collected (FIG. 15).

Figure 16:
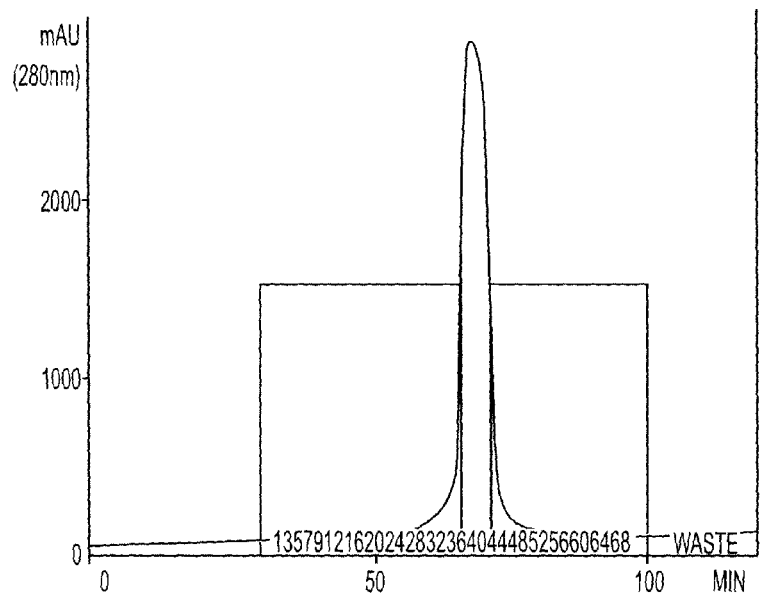
FIG. 16 is a chromatogram of a fraction obtained from the Hydroxyapatite column and further purified on a Superdex200 column in the purification process of the humanized MABL-1 antibody HL5. The hatched area shows a final purified specimen recovered.

The fractions obtained in the second step were concentrated on Centriprep YM-10 (Millipore), and applied to HiLoad 26/60 Superdex 200 pg columns (Amersham Bioscience) equilibrated with 20 mM acetate buffer, pH 6.0 containing 0.02% Tween 20 and 0.15 M NaCl. Fractions eluted as main peaks were regarded as purified fractions (FIG. 16). The HL5 eluted at nearly the same position as that of the sc(Fv)$_2$, and no molecule assumed to correspond to the HL5 monomer was observed.

Figure 17:
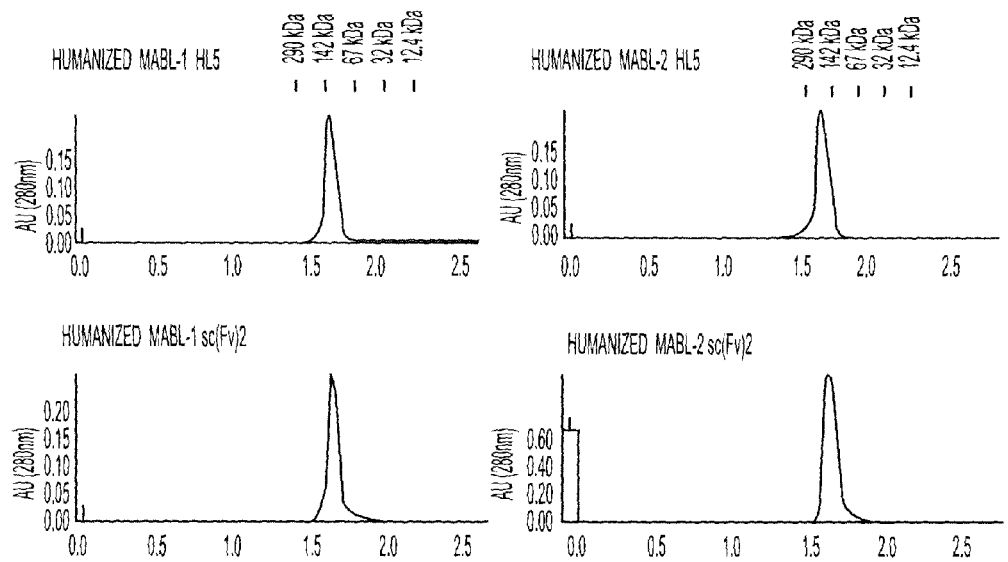
FIG. 17 shows the results of analytic gel filtration of four purified fractions of the humanized MABL-1 antibody HL5 and sc(Fv)$_2$ and the humanized MABL-2 antibody HL5 and sc(Fv)$_2$ on a Superdex 200 column. The humanized MABL-1 antibody HL5 and sc(Fv)$_2$ showed an apparent molecular weight of about 42 kDa and the humanized MABL-2 antibody HL5 and sc(Fv)$_2$ showed an apparent molecular weight of about 40 kDa, all as single peaks.

The four purified fractions of the humanized MABL-1 antibody HL5 and sc(Fv)$_2$ and the humanized MABL-2 antibody HL5 and sc(Fv)$_2$ were assayed by analytical gel filtration using Superdex 200 PC 3.2/30 columns (Amersham Bioscience). The humanized MABL-1 antibody HL5 and sc(Fv)$_2$ showed an apparent molecular weight of about 42 kDa, and the humanized MABL-2 antibody HL5 and sc(Fv)$_2$ showed an apparent molecular weight of about 40 kDa, all as single peaks (FIG. 17). These results showed that the HL5s of the humanized MABL-1,2 antibodies are dimers consisting of two single-chain Fv molecules and that the humanized MABL-1,2 antibody sc(Fv)$_2$s are single-chain Fv monomers.

Figure 18:
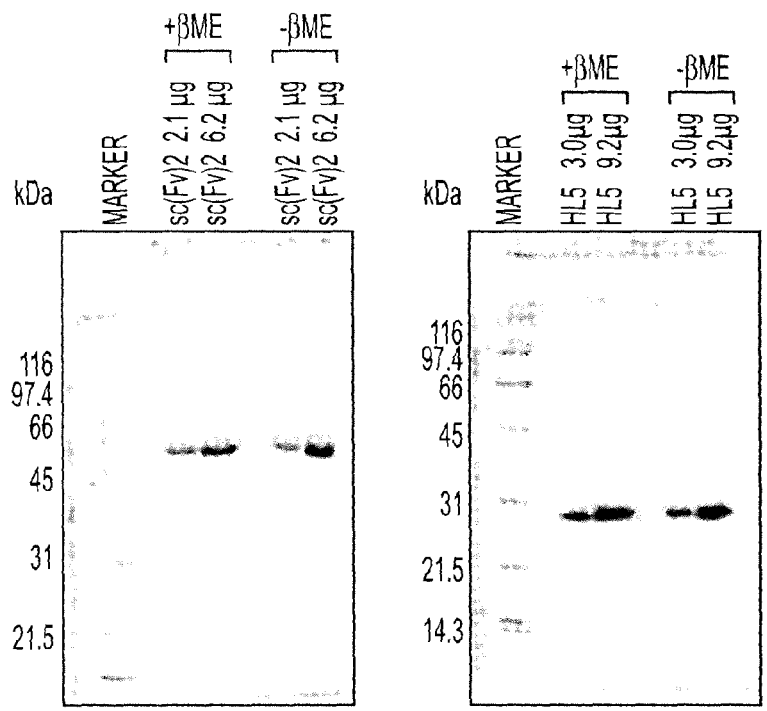
FIG. 18 shows the results of reducing and non-reducing SDS-PAGE analyses of purified humanized MABL-1 antibody HL5 and sc(Fv)$_2$. HL5 showed a single band at a position of the molecular weight of a monomer (about 30 kDa) under both conditions, and sc(Fv)$_2$ showed a single band at a position of the molecular weight of a monomer (about 55 kDa) under both conditions.
Figure 19:
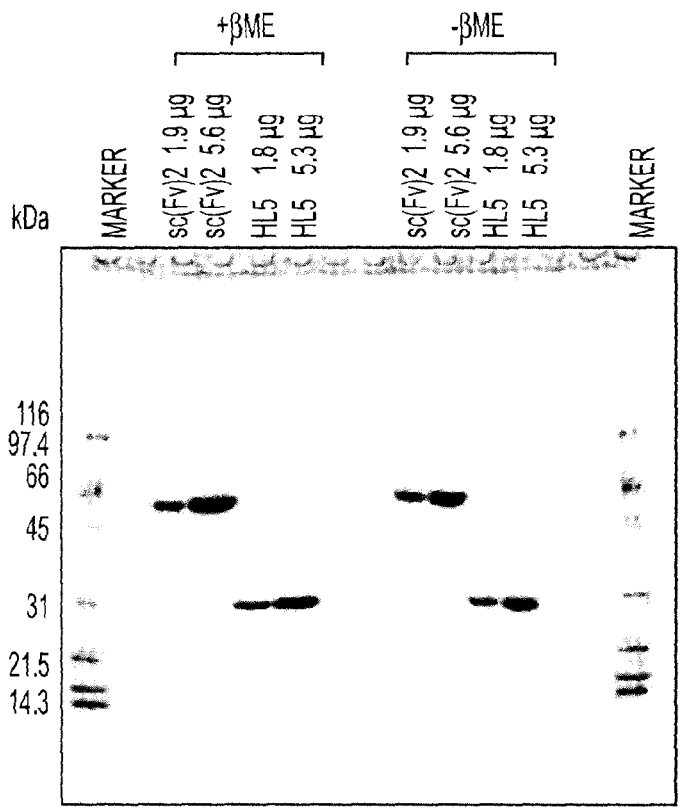
FIG. 19 shows the results of reducing and non-reducing SDS-PAGE analyses of purified humanized MABL-2 antibody HL5 and sc(Fv)$_2$. HL5 showed a single band at a position of the molecular weight of a monomer (about 30 kDa) under both conditions, and sc(Fv)$_2$ showed a single band at a position of the molecular weight of a monomer (about 55 kDa) under both conditions.

As a result of SDS-PAGE analysis under reducing and non-reducing conditions, the humanized MABL-1 antibody HL5 showed a single band at a position of the molecular weight of a monomer (about 30 kDa) under both conditions. The humanized MABL-1 antibody sc(Fv)$_2$ showed a single band at a position of the molecular weight of a monomer (about 55 kDa) under both reducing and non-reducing conditions (FIG. 18). SDS-PAGE analysis of the humanized MABL-2 antibody HL5 and sc(Fv)$_2$ under reducing and non-reducing conditions also gave exactly the same results as those of the humanized MABL-1 antibody (FIG. 19). These results showed that the humanized MABL-1,2 antibody HL5s contain no S—S bridge between molecules and form noncovalent dimers.

Example 6

Figure 20:
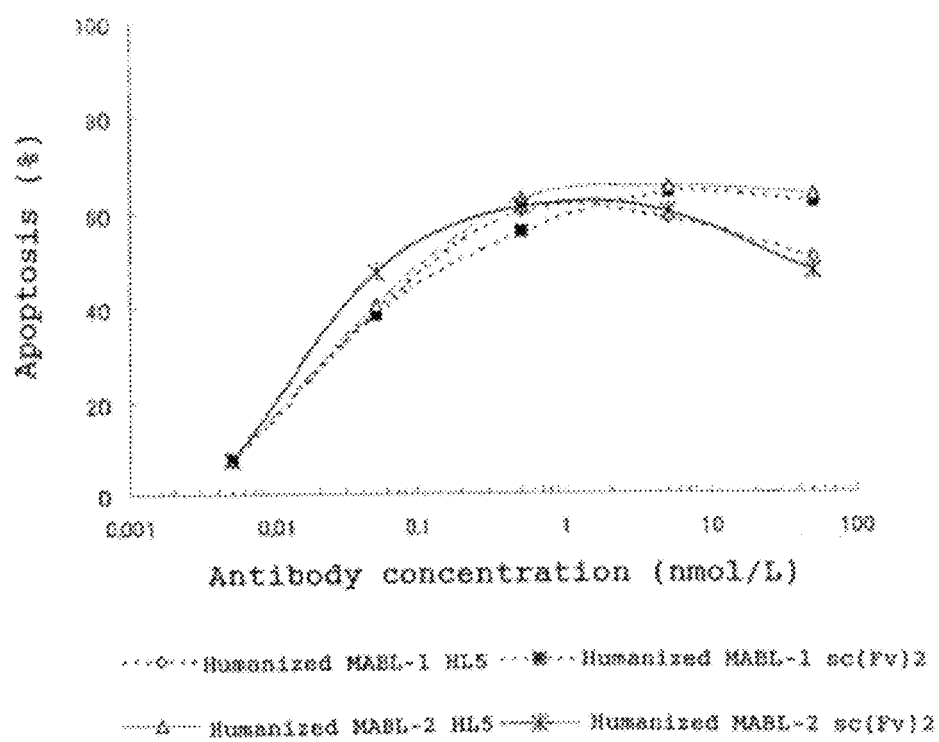
FIG. 20 is a graph showing that the humanized MABL-2 antibody HL5 and sc(Fv)$_2$ and the humanized MABL-1 antibody HL5 and sc(Fv)$_2$ induce cell death in MOLT4 cells.

In Vitro Apoptosis-inducing Effects of the Humanized MABL-1 Antibody HL5 and sc(Fv)$_2$, and the Humanized MABL-2 Antibody HL5 and sc(Fv)$_2$ L1210 cells, MOLT4 cells (ATCC), and JOK-1 cells (Fujisaki Cell Center, Hayashibara Biochemical Labs. Inc.) containing the human CD47 gene were used to evaluate the apoptosis-inducing effects of the humanized MABL-1 antibody HL5 and sc(Fv)$_2$, and the humanized MABL-2 antibody HL5 and sc(Fv)$_2$ by Annexin-V staining (Roche Diagnostics). Ten-fold serial dilutions of each antibody from 50 nmol/L to 0.005 nmol/L or PBS(−) instead of the antibody were added to $1\times10^5$ cells and cultured for 24 hours. Then, Annexin-V staining was performed, and fluorescence intensity was determined by FACSCalibur system (BECTON DICKINSON). As a result, cell death was induced in the all cells. FIG. 20 shows results in MOLT4 cells.

Example 7

Efficacy Test of the Humanized MABL-1 Antibody sc(Fv)$_2$ on Leukemia Model Animals (1) Preparation of a Mouse Model of Human Leukemia A mouse model of human leukemia was prepared as follows. SCID mice (CLEA Japan, Inc.) were used and JOK-1 cells (Fujisaki Cell Center, Hayashibara Biochemical Labs. Inc.) were prepared at $2.5\times10^7$ cells/mL in RPMI1640 medium (GIBCO BRL). SCID mice (male, 6 weeks of age) (CLEA Japan, Inc.) preliminarily treated with 100 μL of an anti-asialo GM1 antibody (Wako Pure Chemical Industries, Ltd., 1 vial dissolved in 5 mL) subcutaneously on the previous day was injected with 200 μL of the suspension of JOK-1 cells ($5\times10^6$ cells/mouse) via the tail vein.

(2) Preparation of an Antibody Sample for Administration

On the day of administration, the humanized MABL-1 antibody sc(Fv)$_2$ was prepared at 1 mg/mL in sterile-filtered PBS(−) to give a sample for administration.

(3) Antibody Administration

The mouse model of human leukemia prepared in (1) was treated with 10 mL/kg of the sample for administration prepared in (2) above via the tail vein twice a day for 5 days starting from 3 days after implantation of JOK-1 cells. As a negative control, autoclaved PBS(−) was similarly administered at 10 mL/kg via tail vein twice a day for 5 days. Both group consisted of 7 animals per group.

(4) Evaluation of Antitumor Effect

Figure 21:
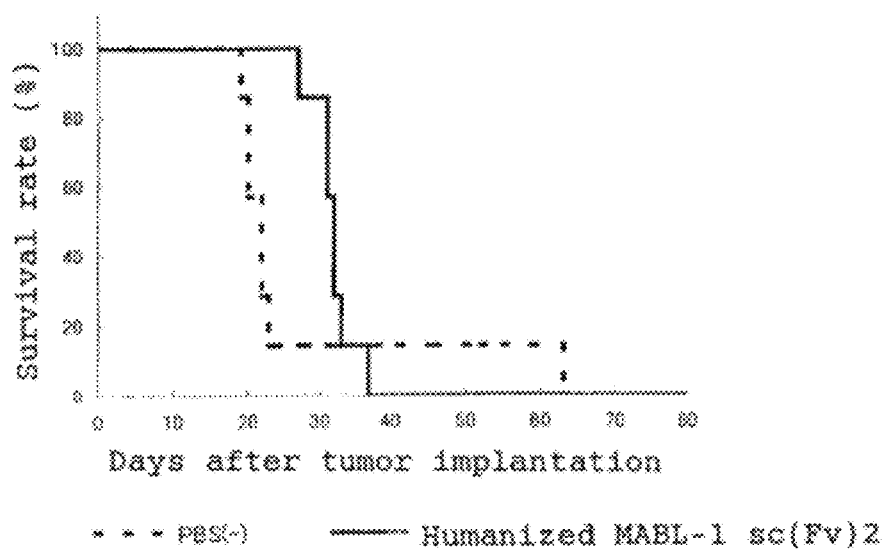
FIG. 21 is a diagram showing that the humanized MABL-1 antibody sc(Fv)$_2$ has a life-extending effect in a mouse model of human leukemia.

Antitumor effect of the humanized MABL-1 antibody sc(Fv)$_2$ in the mouse model of human leukemia was evaluated by survival period. As a result, the group treated with the humanized MABL-1 antibody sc(Fv)$_2$ showed a prolonged survival period as compared with the PBS(−) group, as shown in FIG. 21.

These result showed that the humanized MABL-1 antibody sc(Fv)$_2$ has antitumor effect on the mouse model of human leukemia. This antitumor effect is assumed to be based on the apoptosis-inducing effect of the humanized antibody.

Example 8

Preparation of Humanized MABL-2 HL5s Containing S—S Bonds (1) Introduction of Sequences of S—S Bonds into the Humanized MABL-2 Antibody HL5

Figure 22:
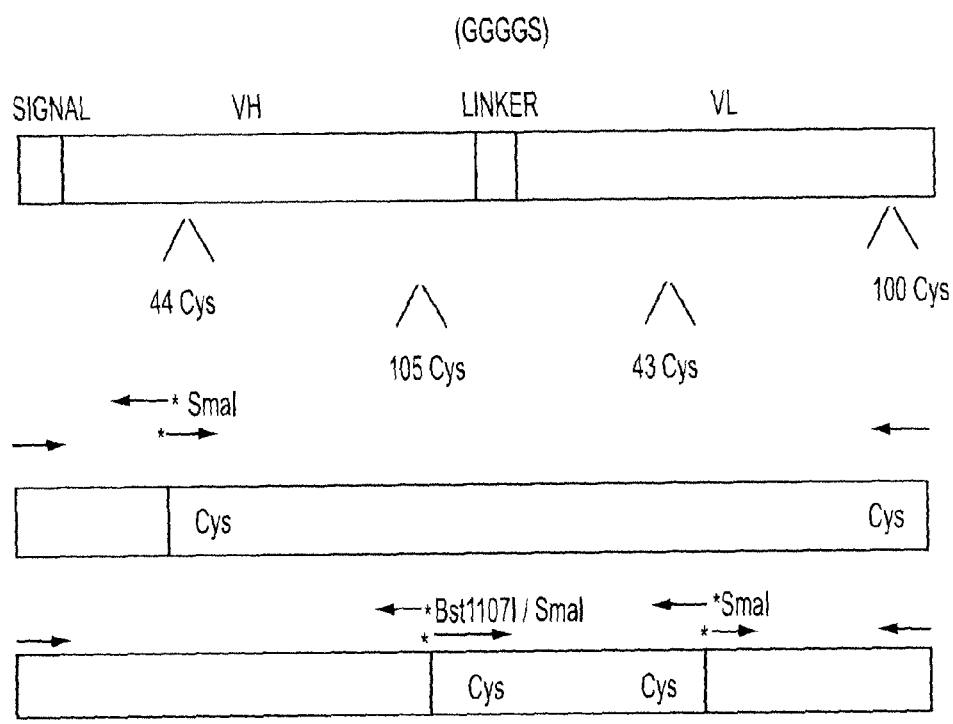
FIG. 22 is a schematic diagram showing the preparation of humanized MABL-2 HL5s containing S—S bonds (GGGGS linker peptide disclosed as SEQ ID NO:109).

An experience for stabilizing diabodies by S—S bonds was performed by replacing two amino acids of the humanized MABL-2 antibody HL5 constructed in Example 4 by cysteine residues (FIG. 22).

The primer sequences for constructing two variants containing S—S bonds by combinations of (i) Cys44(VH)/Cys100(VL), and (ii) Cys105(VH)/Cys43(VL) are shown below.

```
5F44-100 (common)                          (SEQ ID NO: 80)
ctcgaggaattcccaccatgggatggagctgtatcatcc 5R44-100                                   (SEQ ID NO: 81)
gggggcctgtcgcagccagtgaataac 5R105-43                                   (SEQ ID NO: 82)
gggcagtcagtgtatacggccgtgtcgtcagatctgagactgctc 3F44-100                                   (SEQ ID NO: 83)
gggcaatgccttgagtggatgggatatatttatcc 3R44-100                                   (SEQ ID NO: 84)
tcattatttgatctcaagcttggtcccgcagccaaacgtgtacggaacat
gtgt MF105-43                                   (SEQ ID NO: 85)
tactattgtgctagaggggggttactatacttacgacgactggggctgcgc
aaccctggtcacagtctc MR105-43                                   (SEQ ID NO: 86)
gggcttctgcagataccaatgtaaataggtctttc 3F105-43                                   (SEQ ID NO: 87)
gggcagtgcccaagactcctgatctacaaagtttcc 3R105-43                                   (SEQ ID NO: 88)
tcattatttgatctcaagcttggtccctggccaaac
```

PCR reaction was performed using KOD polymerase (Toyobo Ltd.) with pCHOhuM2 Db as template by denaturation at 94° C. for 1 minute followed by 30 cycles of 98° C. for 30 seconds, 65° C. for 2 seconds, and 74° C. for 30 seconds.

A variation for (i) Cys44(VH)/Cys100(VL) was introduced by performing PCR reaction with primer sets 5F44-100/5R44-100 and 3F44-100/3R44-100 and successively ligating the 3' fragment and 5' fragment into the SmaI site of pBluescript SK+ (Stratagene) using Rapid DNA ligation kit (Roche).

A variation for (ii) Cys105(VH)/Cys43(VL) was introduced by performing PCR reaction with primer sets 5F44-100/5R105-43, MF105-43/MR105-43, and 3F105-43/3R105-43, and successively ligating the PCR fragments obtained from 5F44-100/5R105-43 and 3F105-43/3R105-43 into the SmaI site of pBluescript SK+, and then ligating the MF105-43/MR105-43 fragment using the BsT107I site designed by preliminarily introducing a conservative variation into 5R105-43 and MF105-43 and the SmaI site. Thus constructed plasmids were introduced into an *E. coli* DH5a strain (Toyobo Ltd.), and the plasmids were purified (QIAGEN) from the recombinant *E. coli* and analyzed by ABI3100 Genetic Analyzer.

The resulting variants Cys44(VH)/Cys100(VL) and Cys105(VH)/Cys43(VL) are hereinafter referred to as humanized MABL-2 HL5 SS44 and MABL-2 HL5 SS105. The nucleotide sequence and amino acid sequence of MABL-2 HL5 SS44 are shown by SEQ ID NO: 89 and SEQ ID NO: 90, and the nucleotide sequence and amino acid sequence of MABL-2 HL5 SS105 are shown by SEQ ID NO: 91 and SEQ ID NO: 92.

For expression in animal cells, the SS44 and SS105 genes were excised from pBluescript SK+ at BamHI and XhoI and ligated to the same sites of the expression vector pcDNA3.1 (Hygro-) (Invitrogen). These are designated phMABL2 (SS44) and phMABL2 (SS105).

(2) Preparation of Cells Producing the Humanized MABL-2 HL5 Containing S—S Bonds Using CHO (DXB11) Cells Ten micrograms each of phMABL2(SS44) and phMABL2 (SS105) were transferred into $4 \times 10^6$ CHO cells (DXB11) by electroporation [Cytotechnology, 3, 133 (1990)]. After transfer, the cells were suspended in 50 mL of α-MEM-FBS, and a 100 μL aliquot was added to each well of five 96-well plates (Corning). After incubation in a 5% $CO_2$ incubator at 37° C. for 24 hours, the medium was exchanged for α-MEM-FBS containing 100 μg/mL Hygromycin B, and the cells were selected by stepwise increasing the concentration of Hygromycin B to 200 μg/mL and 400 μg/mL.

Thus obtained resistant strains were cultured in α-MEM-FBS containing 10 nM MTX (SIGMA) and 400 μg/mL Hygromycin B for 2 weeks using a DHFR gene amplification system for the purpose of increasing the amount of antibody produced, thereby giving transformants showing resistance to 10 nM MTX. Transformant strains in the well showing growth were further cultured in α-MEM-FBS medium containing 400 μg/mL Hygromycin B and MTX at a concentration increased to 50 nM, 100 nM, 200 nM and finally 400 nM. The binding target soluble human CD47 was immobilized on a BIACORE sensor chip CM5 (Biacore AB) by amine coupling, and the culture supernatants recovered from clones obtained by selective culture were injected into this sensor chip. The expression levels were assayed from the bound amount, and highly expressing clones were selected as cell lines producing the humanized MABL-2 HL5 SS44 and SS105.

3) Culture of the Cells Producing the Humanized MABL-2 HL5 Containing S—S Bonds

The cell lines producing the humanized MABL-2 HL5 SS44 and SS105 obtained in (2) above were adapted in a cell-free medium CHO-S-SFII (GIBCO BRL) containing 100 nM MTX and 400 μg/mL Hygromycin B in a 100 mL spinner flask for 2 weeks. The adapted cells ($1 \times 10^7$ and $1 \times 10^8$ cells, respectively) were inoculated into a 1 L (700 mL medium) or 8 L (6 L medium) spinner flask for cell culture scale up and cultured for 3 or 7 days, and the culture supernatants were recovered.

(4) Purification of the Humanized MABL-2 HL5 Containing S—S Bonds

The humanized MABL-2HL5 SS44 and SS105 (2 types) were purified from the culture supernatants obtained in (3) above by three steps consisting of ion exchange chromatography, hydroxyapatite chromatography, and gel filtration chromatography. Both antibodies were purified by exactly the same procedure, but practically no difference was found in purification results, and therefore, the purification procedure is described generically.

The culture supernatants were diluted with the same volume of 20 mM sodium acetate buffer, pH 5.5 containing 0.02% Tween 20, and then adjusted to pH 5.5 with 1 M acetic acid. Then, the solutions were applied to SP Sepharose Fast Flow columns (Amersham Bioscience) equilibrated with 20 mM sodium acetate buffer, pH 5.5 containing 0.02% Tween 20, and the columns were washed with the same buffer and then polypeptides adsorbed to the columns were eluted with a linear concentration gradient of 0 M to 0.6 M NaCl in the same buffer. Thus obtained fractions were analyzed by SDS-PAGE, and fractions containing the humanized MABL-2HL5 SS44 and SS105 were collected.

The humanized MABL-2HL5 SS44 and SS105 fractions obtained in the first step were adjusted to a pH range of 6.0-6.5 with 0.1 M NaOH, and then applied to hydroxyapatite columns (BIO-RAD, type I, 20 mm) equilibrated with 10 mM phosphate buffer, pH 7.0 containing 0.02% Tween 20, and the columns were washed with the same buffer and then the phosphate buffer concentration was linearly increased to 200 mM to elute polypeptides adsorbed to the columns. Thus obtained fractions were analyzed by SDS-PAGE, and fractions containing desired polypeptides were collected.

The fractions obtained in the second step were concentrated on Centricon YM-10 (Millipore), and applied to HiLoad 16/60 Superdex 200 pg columns (Amersham Bioscience) equilibrated with 20 mM acetate buffer, pH 6.0 containing 0.02% Tween 20 and 0.15 M NaCl. Thus obtained fractions were analyzed by SDS-PAGE, and main peaks containing desired polypeptides were regarded as purified fractions.

Figure 23:
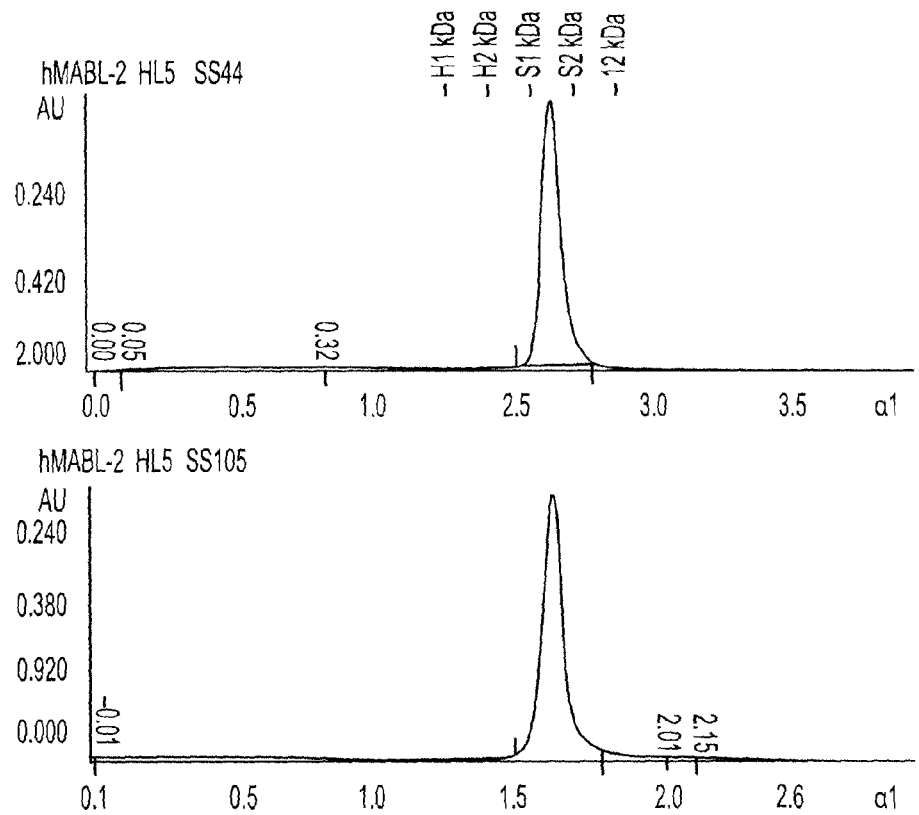
FIG. 23 shows the results of analytic gel filtration of purified humanized MABL-2 antibodies HL5 SS44 and SS105 on a Superdex 200 column. Both showed single peaks and an apparent molecular weight of about 40 kDa.

The two purified fractions of the humanized MABL-2HL5 SS44 and SS105 were assayed by analytical gel filtration using Superdex 200 PC 3.2/30 columns (Amersham Bioscience). Both showed an apparent molecular weight of about 40 kDa as single peaks (FIG. 23).

Figure 24:
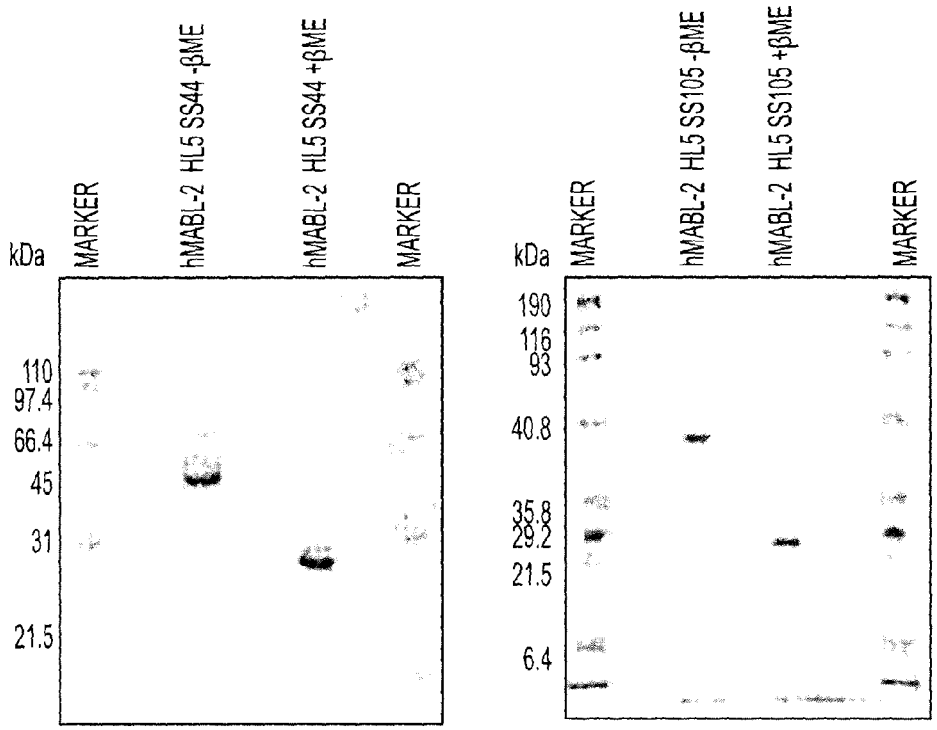
FIG. 24 shows the results of reducing and non-reducing SDS-PAGE analyses of purified humanized MABL-2 antibody HL5 SS44 and SS105. SS44 and SS105 showed a single band at a position of the molecular weight of a monomer (about 26 kDa) under reducing condition and a single band at a position of the molecular weight of a dimer (about 45 kDa) under non-reducing condition.

As a result of SDS-PAGE analysis under reducing and non-reducing conditions, the humanized MABL-2HL5 SS44 and SS105 showed a single band at the position of a molecular weight of a monomer (about 26 kDa) under reducing condition and a single band at the position of a molecular weight of a dimer (about 45 kDa) under non-reducing condition (FIG. 24). These results showed that the humanized MABL-2HL5 SS44 and SS105 are dimers consisting of two single-chain Fv molecules joined by S—S bonds.

Example 9

Figure 25:
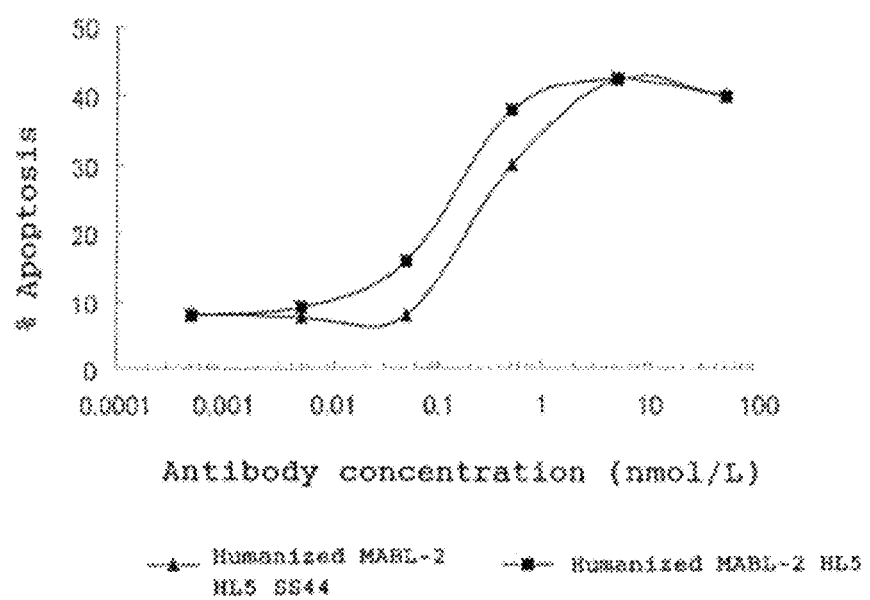
FIG. 25 is a graph showing that the humanized MABL-2 HL5 SS44 and the humanized MABL-2 HL5 induce cell death in L1210 cells containing the human IAP gene.

In vitro Apoptosis-Inducing Effects of the Humanized MABL-2 Antibody HL5s Containing S—S Bonds L1210 cells and JOK-1 cells (Fujisaki Cell Center, Hayashibara Biochemical Labs. Inc.) containing the human CD47 gene were used to evaluate the apoptosis-inducing effects of humanized MABL-2 antibody HL5s containing S—S bonds by Annexin-V staining (Roche Diagnostics). Ten-fold serial dilutions of each antibody from 50 nmol/L to 0.005 nmol/L or PBS(−) instead of the antibody were added to $1\times10^5$ cells and cultured for 24 hours. Then, Annexin-V staining was performed, and fluorescence intensity was determined by FACSCalibur system (BECTON DICKINSON). As a result, cell death was induced in the all cells. FIG. 25 shows the results of apoptosis-inducing effects of the humanized MABL-2 HL5 SS44 on L1210 cells containing the human CD47 gene.

---

The invention claimed is:

1. An isolated nucleic acid encoding a humanized antibody binding to CD47, wherein the encoded antibody comprises:
   (a) a heavy chain variable region comprising the sequence of aa 1-117 of SEQ ID NO: 99; and
   (b) a light chain variable region comprising the sequence of aa 1-112 of SEQ ID NO: 106.

2. The isolated nucleic acid of claim 1 wherein the humanized antibody is a small antibody fragment comprising an antigen-binding domain.

3. The isolated nucleic acid of claim 2, wherein the humanized antibody is a diabody.

4. The isolated nucleic acid of claim 3, wherein the diabody is a single-chain diabody.

5. The isolated nucleic acid of claim 2, wherein a disulfide bond exists between diabody-forming fragments.

6. An isolated nucleic acid encoding an antibody binding to CD47, wherein the encoded antibody comprises any one of:
   (a) the sequence of aa 1-234 of SEQ ID NO: 110; and
   (b) the sequence of aa 1-483 of SEQ ID NO: 113.

7. A vector comprising the nucleic acid of claim 1.

8. A vector comprising the nucleic acid of claim 6.

9. A host cell comprising the vector of claim 7.

10. A process for preparing an antibody, comprising culturing the host cell of claim 9.

* * * * *